(12) United States Patent
Radman

(10) Patent No.: US 11,771,105 B2
(45) Date of Patent: Oct. 3, 2023

(54) DAIRY-LIKE COMPOSITIONS AND RELATED METHODS

(71) Applicant: NEW CULTURE INC., San Leandro, CA (US)

(72) Inventor: Inja Radman, Oakland, CA (US)

(73) Assignee: NEW CULTURE INC., San Leandro, CA (US)

( * ) Notice: Subject to any disclaimer, the term of this patent is extended or adjusted under 35 U.S.C. 154(b) by 0 days.

(21) Appl. No.: 17/829,951

(22) Filed: Jun. 1, 2022

(65) Prior Publication Data

US 2023/0074278 A1 Mar. 9, 2023

Related U.S. Application Data

(60) Provisional application No. 63/234,193, filed on Aug. 17, 2021.

(51) Int. Cl.
| | |
|---|---|
| *A23C 11/00* | (2006.01) |
| *A23C 20/00* | (2006.01) |
| *A23L 9/20* | (2016.01) |
| *A23L 33/19* | (2016.01) |
| *A23C 11/10* | (2021.01) |
| *A23J 3/10* | (2006.01) |

(52) U.S. Cl.
CPC .............. *A23C 20/00* (2013.01); *A23C 11/10* (2013.01); *A23J 3/10* (2013.01); *A23L 9/20* (2016.08); *A23L 33/19* (2016.08)

(58) Field of Classification Search
CPC . A23C 20/00; A23C 11/10; A23L 9/20; A23L 33/19; A23J 3/10
USPC ........................................................ 426/582
See application file for complete search history.

(56) References Cited

U.S. PATENT DOCUMENTS

| | | |
|---|---|---|
| 5,068,118 A | 11/1991 | Strandholm |
| 5,397,577 A | 3/1995 | Le et al. |
| 8,530,423 B2 | 9/2013 | Balandras et al. |
| 8,986,773 B2 | 3/2015 | Beckhoven Van et al. |
| 9,924,728 B2 | 3/2018 | Pandya et al. |
| 10,595,545 B2 | 3/2020 | Pandya et al. |
| 10,894,812 B1 | 1/2021 | Lanquar et al. |
| 10,993,453 B2 | 5/2021 | Coker et al. |
| 11,076,611 B2 | 8/2021 | Favre et al. |
| 2010/0223682 A1 | 9/2010 | Katz et al. |
| 2017/0273328 A1 | 9/2017 | Pandya et al. |
| 2018/0271111 A1 | 9/2018 | Pandya et al. |
| 2019/0216106 A1 | 7/2019 | Geistlinger et al. |

(Continued)

FOREIGN PATENT DOCUMENTS

| | | |
|---|---|---|
| CA | 2958858 A1 | 2/2016 |
| EP | 1197152 A2 | 4/2002 |

(Continued)

OTHER PUBLICATIONS

Bönisch et al. Influence of transglutaminase protein cross-linking on the rennet coagulation of casein. Food Hydrocolloids 22 (2008) 288-297.

(Continued)

*Primary Examiner* — Brent T O'Hern
(74) *Attorney, Agent, or Firm* — MORRISON & FOERSTER LLP

(57) ABSTRACT

Provided herein are dairy-like analogue compositions and the methods of making the same using one or more recombinant proteins.

17 Claims, 8 Drawing Sheets

Specification includes a Sequence Listing.

Full length bovine alpha-S1-casein
N-terminally truncated bovine alpha-S1-casein
N-terminally truncated bovine alpha-S1-casein

PC   CL

PC – Purified recombinant bovine alpha-S1-casein
CL – Crude lysate

(56) References Cited

U.S. PATENT DOCUMENTS

| | | |
|---|---|---|
| 2020/0123556 A1 | 4/2020 | El-Richani et al. |
| 2021/0235714 A1 | 8/2021 | Geistlinger et al. |
| 2022/0169690 A1 | 6/2022 | Lanquar et al. |
| 2022/0174972 A1 | 6/2022 | Gibson et al. |
| 2022/0211061 A1* | 7/2022 | Geistlinger ........ C07K 14/4732 |
| 2023/0141532 A1 | 5/2023 | Gibson et al. |

FOREIGN PATENT DOCUMENTS

| | | |
|---|---|---|
| EP | 3182842 A1 | 6/2017 |
| JP | 2017528162 A | 9/2017 |
| WO | WO-9315196 A1 | 8/1993 |
| WO | WO-9724371 A1 | 7/1997 |
| WO | WO-2007055932 A1 | 5/2007 |
| WO | WO-2016029193 A1 | 2/2016 |
| WO | WO-2017077189 A1 | 5/2017 |
| WO | WO-2018039632 A1 | 3/2018 |
| WO | WO-2018187754 A1 | 10/2018 |
| WO | WO-2019213155 A1 | 11/2019 |
| WO | WO-2020061503 A1 | 3/2020 |
| WO | WO-2020081789 A1 | 4/2020 |
| WO | WO-2020115012 A1 | 6/2020 |
| WO | WO-2020172623 A1 | 8/2020 |
| WO | WO-2020219595 A1 | 10/2020 |
| WO | WO-2020219596 A1 | 10/2020 |
| WO | WO-2020223700 A1 | 11/2020 |
| WO | WO-2021116914 A1 | 6/2021 |
| WO | WO-2021152057 A1 | 8/2021 |
| WO | WO-2021152106 A1 | 8/2021 |
| WO | WO-2021168343 A2 | 8/2021 |
| WO | WO-2022038601 A1 | 2/2022 |
| WO | WO-2022058573 A1 | 3/2022 |
| WO | WO-2022098835 A1 | 5/2022 |
| WO | WO-2022098853 A1 | 5/2022 |

OTHER PUBLICATIONS

Loveday et al. Innovative yoghurts: Novel processing technologies for improving acid milk gel texture. Trends in Food Science & Technology, vol. 33, Issue 1, pp. 5-20 (2013). Retrieved Jun. 15, 2022 at URL: https://www.researchgate.net/profile/Simon-Loveday/publication/243963238_Innovative_yoghurts_Novel_processing_technologies_for_improving_acid_milk_gel_texture/links/5ff53430a6fdccdcb833aa16/Innovative-yoghurts-Novel-processing-technologies-for-improving-acid-milk-gel-texture.pdf.
Schmidt et al. On the formation of artificial casein micelles. Milchwissenschaft 29(8): 455-459 (1974).
Waugh et al. "Casein Micelles: Formation and Structure." Brooks et al, eds. Federation Proceedings, vol. 24, p. 418, Abstract 1601 (1965). Federation of American Societies for Experimental Biology 49th Annual Meeting, Atlantic City, NJ, Apr. 9-14, 1965.
Ali et al. Use of Mass Spectrometry to Profile Peptides in Whey Protein Isolate Medium Fermented by Lactobacillus helveticus LH-2 and Lactobacillus acidophilus La-5. Frontiers in Nutrition, vol. 6, Article 152 (Oct. 15, 2019). 19 pages.
Altschul et al. Basic local alignment search tool. J Mol Biol 215(3):403-410 (1990).
Aoki et al. Caseins are cross-linked through their ester phosphate groups by colloidal calcium phosphate. Biochim Biophys Acta. Jan. 30, 1987;911(2):238-43. doi: 10.1016/0167-4838(87)90013-6.
Aoki et al. Role of Individual Milk Salt Constituents in Cross-linking by Colloidal Calcium Phosphate in Artificial Casein Micelles, Agricultural and Biological Chemistry, 51:3, 817-821 (1987). DOI: 10.1080/00021369.1987.10868109.
Bingham et al. Properties of dephosphorylated αs1-casein. Precipitation by calcium ions and micelle formation. Biochemistry. Jun. 20, 1972;11(13):2450-4. doi: 10.1021/bi00763a010.
"Bovinae." Wikipedia. Page last edited Feb. 28, 2022. Retrieved Feb. 28, 2022 at URL: https://en.wikipedia.org/wiki/Bovinae. 3 pages.

Broyard et al. Modifications of structures and functions of caseins: a scientific and technological challenge. Dairy Science & Technology, EDP sciences/Springer, 2015, 95 (6), pp. 831-862. (10.1007/s13594-015-0220-y). (hal-01294069).
"Caprinae." Wikipedia. Page last edited Feb. 12, 2022. Retrieved Feb. 28, 2022 at URL: https://en.wikipedia.org/wiki/Caprinae. 7 pages.
De Kermadec et al. Real Vegan Cheese Progress Report (Draft), Real Vegan Cheese Project. Nov. 2018. Retrieved Jun. 13, 2022 at URL: https://static1.squarespace.com/static/5dd519035ccc387bd8010b70/t/5fd82601aa13016ef02619eb/1608001025574/Real+Vegan+Cheese+Progress+Report+-+2018+Draft.pdf. 5 pages.
Gatti et al. Effect of the anion citrate on the mineral composition of artificial casein micelles. J Agric Food Chem. Jan. 1999;47(1):141-4. doi: 10.1021/jf980402e.
Gaudin et al. Engineering of caseins and modulation of their structures and interactions. Biotechnol Adv. Nov.-Dec. 2009;27(6):1124-1131. doi: 10.1016/j.biotechadv.2009.05.011. Epub May 20, 2009.
Goda et al. Production of synthetic methionine-free and synthetic methionine-limited alpha casein: protein foodstuff for patients with homocystinuria due to cystathionine beta-synthase deficiency. Protein J. Jan. 2010;29(1):44-9. doi: 10.1007/s10930-009-9219-7.
Goda et al. Recombinant expression analysis of natural and synthetic bovine alpha-casein in *Escherichia coli*. Appl Microbiol Biotechnol. Nov. 2000;54(5):671-6. doi: 10.1007/S002530000435.
Hill. Milk Composition and Properties. Presentation. University of Guelph. Presented Aug. 6, 2011 at American Cheese Society Conference, Montréal, CA. Retrieved at URL: https://kipdf.com/download/milk-composition-and-properties_5ac5f8c41723dddc5d22ad2c.html. 33 pages.
Hiller et al. Effect of phosphatase/transglutaminase treatment on molar mass distribution and techno-functional properties of sodium caseinate. LWT—Food Science and Technology, vol. 42, Issue 1, pp. 87-92 (2009). DOI: https://doi.org/10.1016/j.lwt.2008.06.003.
Holland. Chapter 4: Post-translational modifications of caseins, pp. 107-132. In Milk Proteins: From Express to Food. Thompson, et al, eds., Elsevier, 2009. Retrieved Jun. 13, 2022 at URL: http://ubblab.weebly.com/uploads/4/7/4/6/47469791/milk_proteins_from_expression_to_food.pdf.
Holt et al. Darwinian transformation of a 'scarcely nutritious fluid' into milk. J Evol Biol 25, pp. 1253-1263 (2012).
Horne. Chapter 5: Casein micelle structure and stability, pp. 133-162. In Milk Proteins: From Express to Food. Thompson, et al, eds., Elsevier, 2009. Retrieved Jun. 13, 2022 at URL: http://ubblab.weebly.com/uploads/4/7/4/6/47469791/milk_proteins_from_expression_to_food.pdf.
Ikura et al. Crosslinking of Casein Components by Transglutaminase. Agric Biol Chem 44(7):1567-1573 (1980).
Kang et al. Molecular cloning and expression of bovine kappa-casein in *Escherichia coli*. J Dairy Sci. Jan. 1988;71(1):29-40. doi: 10.3168/jds.S0022-0302(88)79521-1.
Kindstedt. Mechanisms of Coagulation: The principles, the science and what they mean to cheesemakers. Presentation. University of Vermont. Presented Aug. 5, 2011 at American Cheese Society Conference, Montréal, CA. Retrieved at URL: https://www.cheesesociety.org/wp-content/uploads/2011/08/2011-Mechanisms-of-Coagulation-Kindstedt.pdf. 52 pages.
Knoop et al. Sub-structure of synthetic casein micelles. J Dairy Res. Apr. 1979;46(2):347-50. doi: 10.1017/s0022029900017295.
Losacco et al. Production of active angiotensin-I converting enzyme inhibitory peptides derived from bovine beta-casein by recombinant DNA technologies. Biotechnol J. Nov. 2007;2(11):1425-34. doi: 10.1002/biot.200700092.
Minkiewicz et al. The Contribution of N-Acetylneuraminic Acid in the Stabilization of Micellar Casein. Pol J Food Nutr Sci, vol. 2/43, No. 3, pp. 39-48 (Sep. 1993).
Mounsey et al. Influence of transglutaminase treatment on properties of micellar casein and products made therefrom. Lait 85 (2005) 405-418. DOI: 10.1051/lait:2005028. Published online Jul. 5, 2005.
Ono et al. Formation of Artificial Casein Micelles. Agricultural and Biological Chemistry, 47:2, 221-226 (1983). DOI: 0.1080/00021369.1983.10865628.

(56) References Cited

OTHER PUBLICATIONS

PCT/US2020/031177 International Search Report and Written Opinion dated Jul. 14, 2020.
PCT/US2021/058004 International Search Report and Written Opinion dated Feb. 3, 2022.
PCT/US2021/058029 International Search Report and Written Opinion dated Feb. 8, 2022.
Pearse et al. Effect of casein micelle composition and casein dephosphorylation on coagulation and syneresis. Journal of Dairy Research, vol. 53, Issue 3, pp. 381-390 (Aug. 1986). DOI: https://doi.org/10.1017/S0022029900025000.
Pearson. Rapid and sensitive sequence comparison with FASTP and FASTA. Methods Enzymol. 1990;183:63-98.
Pepper et al. Dephosphorylation of αS- and κ-Caseins and Its Effect on Micelle Stability in the κ-αS-Casein System. Journal of Dairy Science, vol. 46, Issue 8, pp. 764-767 (Aug. 1963). DOI: https://doi.org/10.3168/jds.S0022-0302(63)89145-6.
Phadungath, C. Casein micelle structure: a concise review. Songklanakarin J. Sci. Technol., 2005, 27(1) : 201-212.
Qi, Phoebe X. Studies of casein micelle structure: the past and the present. Le Lait, INRA Editions, 2007, 87 (4-5), pp. 363-383. (hal-00895656).
Raynes. Selecting Beneficial Protein Components From all Dairy Animals for Manufacturing Next Generation Infant Formulas. Presentation. CSIRO. Sep. 14, 2017. 20 pages.
Reid et al. Specificity of *Lactococcus lactis* subsp. cremoris SK11 Proteinase, Lactocepin III, in Low-Water-Activity, High-Salt-Concentration Humectant Systems and Its Stability Compared with That of Lactocepin I. Applied and Environmental Microbiology, vol. 65, No. 7, pp. 2947-2953 (Jul. 1999).
Schulmeister et al. Cloning, expression, and mapping of allergenic determinants of alphaS1-casein, a major cow's milk allergen. J Immunol. Jun. 1, 2009;182(11):7019-29. doi: 10.4049/jimmunol.0712366.
Sheehy, et al. Chapters: Significance, origin and function of bovine milk proteins: the biological implications of manipulation or modification, pp. 81-106. In Milk Proteins: From Express to Food. Thompson, et al, eds., Elsevier, 2009. Retrieved Jun. 13, 2022 at URL: http://ubblab.weebly.com/uploads/4/7/4/6/47469791/milk_proteins_from_expression_to_food.pdf.
Simons et al. Overproduction of bovine β-casein in *Escherichia coli* and engineering of its main chymosin cleavage site. Protein Engineering, Design and Selection, vol. 6, Issue 7, pp. 763-770 (Sep. 1, 1993). DOI: https://doi.org/10.1093/protein/6.7.763.
Smiddy et al. Stability of casein micelles cross-linked by transglutaminase. J. Dairy Sci. 89(6):1906-1914 (2006).
Waugh et al. Casein Micelles. Formation and Structure II. J Am Chem Soc May 20, 1965;87:2246-57. doi: 10.1021/ja01088a026.
Yousefi et al. Chaperone-like activities of different molecular forms of beta-casein. Importance of polarity of N-terminal hydrophilic domain. Biopolymers. Aug. 2009;91(8):623-32. doi: 10.1002/bip.21190.
Yousefi et al. Micellisation and immunoreactivities of dimeric beta-caseins. Biochim Biophys Acta. Dec. 2009;1794(12):1775-83. doi: 10.1016/j.bbapap.2009.08.015. Epub Aug. 20, 2009.
Zakharchenko et al. Chaperone-like activity of β-casein and thermal stability of alcohol dehydrogenase. Russ J Bioorg Chem 38, 192-197 (2012). DOI: https://doi.org/10.1134/S1068162012020136.
International Search Report and Written Opinion received for International Patent Application No. PCT/US2022/040658 dated Nov. 21, 2022, 16 pages.
U.S Unpublished U.S. Appl. No. 18/055,016, filed Nov. 14, 2022 titled "Cheese and Yogurt Like Compositions and Related Methods," (Copy not submitted herewith pursuant to the waiver of 37 C.F.R. § 1.98(a)(2)(iii)).
Extended European Search Report received for European Patent Application No. 20799034.2 dated Mar. 15, 2023, 11 pages.
Laible et al., (2016). "Increased gene dosage for [beta]- and [kappa]-casein in transgenic cattle improves milk composition through complex effects," Scientific Reports, 6:37607, 10 pages.
U.S Unpublished U.S. Appl. No. 18/035,263, internationally filed on Nov. 4, 2021 titled "Micelle and Micelle-Like Compositions and Related Methods," (Copy not submitted herewith pursuant to the waiver of 37 C.F.R. § 1.98(a)(2)(iii)).
U.S Unpublished U.S. Appl. No. 18/035,257, internationally filed on Nov. 4, 2021 titled "Dairy-Like Compositions and Related Methods," (Copy not submitted herewith pursuant to the waiver of 37 C.F.R. § 1.98(a)(2)(iii)).

\* cited by examiner

```
                     SEQUENCE LISTING

<160> NUMBER OF SEQ ID NOS: 56

<210> SEQ ID NO 1
<211> LENGTH: 214
<212> TYPE: PRT
<213> ORGANISM: Bos taurus

<400> SEQUENCE: 1

Met Lys Leu Leu Ile Leu Thr Cys Leu Val Ala Val Ala Leu Ala Arg
1               5                   10                  15

Pro Lys His Pro Ile Lys His Gln Gly Leu Pro Gln Glu Val Leu Asn
                20                  25                  30

Glu Asn Leu Leu Arg Phe Phe Val Ala Pro Phe Pro Glu Val Phe Gly
            35                  40                  45

Lys Glu Lys Val Asn Glu Leu Ser Lys Asp Ile Gly Ser Glu Ser Thr
        50                  55                  60

Glu Asp Gln Ala Met Glu Asp Ile Lys Gln Met Glu Ala Glu Ser Ile
65                  70                  75                  80

Ser Ser Ser Glu Glu Ile Val Pro Asn Ser Val Glu Gln Lys His Ile
                85                  90                  95

Gln Lys Glu Asp Val Pro Ser Glu Arg Tyr Leu Gly Tyr Leu Glu Gln
            100                 105                 110

Leu Leu Arg Leu Lys Lys Tyr Lys Val Pro Gln Leu Glu Ile Val Pro
        115                 120                 125

Asn Ser Ala Glu Glu Arg Leu His Ser Met Lys Glu Gly Ile His Ala
130                 135                 140

Gln Gln Lys Glu Pro Met Ile Gly Val Asn Gln Glu Leu Ala Tyr Phe
145                 150                 155                 160

Tyr Pro Glu Leu Phe Arg Gln Phe Tyr Gln Leu Asp Ala Tyr Pro Ser
                165                 170                 175

Gly Ala Trp Tyr Tyr Val Pro Leu Gly Thr Gln Tyr Thr Asp Ala Pro
            180                 185                 190

Ser Phe Ser Asp Ile Pro Asn Pro Ile Gly Ser Glu Asn Ser Glu Lys
        195                 200                 205

Thr Thr Met Pro Leu Trp
    210

<210> SEQ ID NO 2
<211> LENGTH: 199
<212> TYPE: PRT
<213> ORGANISM: Bos taurus

<400> SEQUENCE: 2

Arg Pro Lys His Pro Ile Lys His Gln Gly Leu Pro Gln Glu Val Leu
1               5                   10                  15
```

Asn Glu Asn Leu Leu Arg Phe Phe Val Ala Pro Phe Pro Glu Val Phe
             20                  25                  30

Gly Lys Glu Lys Val Asn Glu Leu Ser Lys Asp Ile Gly Ser Glu Ser
         35                  40                  45

Thr Glu Asp Gln Ala Met Glu Asp Ile Lys Gln Met Glu Ala Glu Ser
 50                  55                  60

Ile Ser Ser Ser Glu Glu Ile Val Pro Asn Ser Val Glu Gln Lys His
 65                  70                  75                  80

Ile Gln Lys Glu Asp Val Pro Ser Glu Arg Tyr Leu Gly Tyr Leu Glu
                 85                  90                  95

Gln Leu Leu Arg Leu Lys Lys Tyr Lys Val Pro Gln Leu Glu Ile Val
             100                 105                 110

Pro Asn Ser Ala Glu Glu Arg Leu His Ser Met Lys Glu Gly Ile His
         115                 120                 125

Ala Gln Gln Lys Glu Pro Met Ile Gly Val Asn Gln Glu Leu Ala Tyr
130                 135                 140

Phe Tyr Pro Glu Leu Phe Arg Gln Phe Tyr Gln Leu Asp Ala Tyr Pro
145                 150                 155                 160

Ser Gly Ala Trp Tyr Tyr Val Pro Leu Gly Thr Gln Tyr Thr Asp Ala
                 165                 170                 175

Pro Ser Phe Ser Asp Ile Pro Asn Pro Ile Gly Ser Glu Asn Ser Glu
             180                 185                 190

Lys Thr Thr Met Pro Leu Trp
         195

<210> SEQ ID NO 3
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Arg Pro Lys His Pro Ile Lys His Gln Gly Leu Pro Gln Glu Val
 1               5                  10                  15

Leu Asn Glu Asn Leu Leu Arg Phe Phe Val Ala Pro Phe Pro Glu Val
             20                  25                  30

Phe Gly Lys Glu Lys Val Asn Glu Leu Ser Lys Asp Ile Gly Ser Glu
         35                  40                  45

Ser Thr Glu Asp Gln Ala Met Glu Asp Ile Lys Gln Met Glu Ala Glu
 50                  55                  60

Ser Ile Ser Ser Ser Glu Glu Ile Val Pro Asn Ser Val Glu Gln Lys
 65                  70                  75                  80

His Ile Gln Lys Glu Asp Val Pro Ser Glu Arg Tyr Leu Gly Tyr Leu
                 85                  90                  95

Glu Gln Leu Leu Arg Leu Lys Lys Tyr Lys Val Pro Gln Leu Glu Ile
             100                 105                 110

Val Pro Asn Ser Ala Glu Glu Arg Leu His Ser Met Lys Glu Gly Ile
         115                 120                 125

His Ala Gln Gln Lys Glu Pro Met Ile Gly Val Asn Gln Glu Leu Ala
130                 135                 140

Tyr Phe Tyr Pro Glu Leu Phe Arg Gln Phe Tyr Gln Leu Asp Ala Tyr
145                 150                 155                 160

Pro Ser Gly Ala Trp Tyr Tyr Val Pro Leu Gly Thr Gln Tyr Thr Asp

```
                    165                 170                 175

Ala Pro Ser Phe Ser Asp Ile Pro Asn Pro Ile Gly Ser Glu Asn Ser
            180                 185                 190

Glu Lys Thr Thr Met Pro Leu Trp
        195                 200

<210> SEQ ID NO 4
<211> LENGTH: 177
<212> TYPE: PRT
<213> ORGANISM: Bos taurus

<400> SEQUENCE: 4

Phe Phe Val Ala Pro Phe Pro Glu Val Phe Gly Lys Glu Lys Val Asn
1               5                   10                  15

Glu Leu Ser Lys Asp Ile Gly Ser Glu Ser Thr Glu Asp Gln Ala Met
            20                  25                  30

Glu Asp Ile Lys Gln Met Glu Ala Glu Ser Ile Ser Ser Ser Glu Glu
        35                  40                  45

Ile Val Pro Asn Ser Val Glu Gln Lys His Ile Gln Lys Glu Asp Val
    50                  55                  60

Pro Ser Glu Arg Tyr Leu Gly Tyr Leu Glu Gln Leu Leu Arg Leu Lys
65                  70                  75                  80

Lys Tyr Lys Val Pro Gln Leu Glu Ile Val Pro Asn Ser Ala Glu Glu
                85                  90                  95

Arg Leu His Ser Met Lys Glu Gly Ile His Ala Gln Gln Lys Glu Pro
            100                 105                 110

Met Ile Gly Val Asn Gln Glu Leu Ala Tyr Phe Tyr Pro Glu Leu Phe
        115                 120                 125

Arg Gln Phe Tyr Gln Leu Asp Ala Tyr Pro Ser Gly Ala Trp Tyr Tyr
    130                 135                 140

Val Pro Leu Gly Thr Gln Tyr Thr Asp Ala Pro Ser Phe Ser Asp Ile
145                 150                 155                 160

Pro Asn Pro Ile Gly Ser Glu Asn Ser Gly Lys Thr Thr Met Pro Leu
                165                 170                 175

Trp

<210> SEQ ID NO 5
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Phe Phe Val Ala Pro Phe Pro Glu Val Phe Gly Lys Glu Lys Val
1               5                   10                  15

Asn Glu Leu Ser Lys Asp Ile Gly Ser Glu Ser Thr Glu Asp Gln Ala
            20                  25                  30

Met Glu Asp Ile Lys Gln Met Glu Ala Glu Ser Ile Ser Ser Ser Glu
        35                  40                  45

Glu Ile Val Pro Asn Ser Val Glu Gln Lys His Ile Gln Lys Glu Asp
    50                  55                  60

Val Pro Ser Glu Arg Tyr Leu Gly Tyr Leu Glu Gln Leu Leu Arg Leu
65                  70                  75                  80

Lys Lys Tyr Lys Val Pro Gln Leu Glu Ile Val Pro Asn Ser Ala Glu
                85                  90                  95
```

```
Glu Arg Leu His Ser Met Lys Glu Gly Ile His Ala Gln Gln Lys Glu
            100                 105                 110

Pro Met Ile Gly Val Asn Gln Glu Leu Ala Tyr Phe Tyr Pro Glu Leu
        115                 120                 125

Phe Arg Gln Phe Tyr Gln Leu Asp Ala Tyr Pro Ser Gly Ala Trp Tyr
    130                 135                 140

Tyr Val Pro Leu Gly Thr Gln Tyr Thr Asp Ala Pro Ser Phe Ser Asp
145                 150                 155                 160

Ile Pro Asn Pro Ile Gly Ser Glu Asn Ser Gly Lys Thr Thr Met Pro
                165                 170                 175

Leu Trp

<210> SEQ ID NO 6
<211> LENGTH: 176
<212> TYPE: PRT
<213> ORGANISM: Bos taurus

<400> SEQUENCE: 6

Phe Val Ala Pro Phe Pro Glu Val Phe Gly Lys Glu Lys Val Asn Glu
1               5                   10                  15

Leu Ser Lys Asp Ile Gly Ser Glu Ser Thr Glu Asp Gln Ala Met Glu
            20                  25                  30

Asp Ile Lys Gln Met Glu Ala Glu Ser Ile Ser Ser Ser Glu Glu Ile
        35                  40                  45

Val Pro Asn Ser Val Glu Gln Lys His Ile Gln Lys Glu Asp Val Pro
    50                  55                  60

Ser Glu Arg Tyr Leu Gly Tyr Leu Glu Gln Leu Leu Arg Leu Lys Lys
65                  70                  75                  80

Tyr Lys Val Pro Gln Leu Glu Ile Val Pro Asn Ser Ala Glu Glu Arg
                85                  90                  95

Leu His Ser Met Lys Glu Gly Ile His Ala Gln Gln Lys Glu Pro Met
            100                 105                 110

Ile Gly Val Asn Gln Glu Leu Ala Tyr Phe Tyr Pro Glu Leu Phe Arg
        115                 120                 125

Gln Phe Tyr Gln Leu Asp Ala Tyr Pro Ser Gly Ala Trp Tyr Tyr Val
    130                 135                 140

Pro Leu Gly Thr Gln Tyr Thr Asp Ala Pro Ser Phe Ser Asp Ile Pro
145                 150                 155                 160

Asn Pro Ile Gly Ser Glu Asn Ser Gly Lys Thr Thr Met Pro Leu Trp
                165                 170                 175

<210> SEQ ID NO 7
<211> LENGTH: 177
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Phe Val Ala Pro Phe Pro Glu Val Phe Gly Lys Glu Lys Val Asn
1               5                   10                  15

Glu Leu Ser Lys Asp Ile Gly Ser Glu Ser Thr Glu Asp Gln Ala Met
            20                  25                  30

Glu Asp Ile Lys Gln Met Glu Ala Glu Ser Ile Ser Ser Ser Glu Glu
        35                  40                  45
```

Ile Val Pro Asn Ser Val Glu Gln Lys His Ile Gln Lys Glu Asp Val
 50                  55                  60

Pro Ser Glu Arg Tyr Leu Gly Tyr Leu Glu Gln Leu Leu Arg Leu Lys
 65                  70                  75                  80

Lys Tyr Lys Val Pro Gln Leu Glu Ile Val Pro Asn Ser Ala Glu Glu
                 85                  90                  95

Arg Leu His Ser Met Lys Glu Gly Ile His Ala Gln Gln Lys Glu Pro
            100                 105                 110

Met Ile Gly Val Asn Gln Glu Leu Ala Tyr Phe Tyr Pro Glu Leu Phe
            115                 120                 125

Arg Gln Phe Tyr Gln Leu Asp Ala Tyr Pro Ser Gly Ala Trp Tyr Tyr
130                 135                 140

Val Pro Leu Gly Thr Gln Tyr Thr Asp Ala Pro Ser Phe Ser Asp Ile
145                 150                 155                 160

Pro Asn Pro Ile Gly Ser Glu Asn Ser Gly Lys Thr Thr Met Pro Leu
                165                 170                 175

Trp

<210> SEQ ID NO 8
<211> LENGTH: 175
<212> TYPE: PRT
<213> ORGANISM: Bos taurus

<400> SEQUENCE: 8

Val Ala Pro Phe Pro Glu Val Phe Gly Lys Glu Lys Val Asn Glu Leu
 1               5                  10                  15

Ser Lys Asp Ile Gly Ser Glu Ser Thr Glu Asp Gln Ala Met Glu Asp
                 20                  25                  30

Ile Lys Gln Met Glu Ala Glu Ser Ile Ser Ser Ser Glu Glu Ile Val
            35                  40                  45

Pro Asn Ser Val Glu Gln Lys His Ile Gln Lys Glu Asp Val Pro Ser
 50                  55                  60

Glu Arg Tyr Leu Gly Tyr Leu Glu Gln Leu Leu Arg Leu Lys Lys Tyr
65                  70                  75                  80

Lys Val Pro Gln Leu Glu Ile Val Pro Asn Ser Ala Glu Glu Arg Leu
                 85                  90                  95

His Ser Met Lys Glu Gly Ile His Ala Gln Gln Lys Glu Pro Met Ile
            100                 105                 110

Gly Val Asn Gln Glu Leu Ala Tyr Phe Tyr Pro Glu Leu Phe Arg Gln
        115                 120                 125

Phe Tyr Gln Leu Asp Ala Tyr Pro Ser Gly Ala Trp Tyr Tyr Val Pro
130                 135                 140

Leu Gly Thr Gln Tyr Thr Asp Ala Pro Ser Phe Ser Asp Ile Pro Asn
145                 150                 155                 160

Pro Ile Gly Ser Glu Asn Ser Gly Lys Thr Thr Met Pro Leu Trp
                165                 170                 175

<210> SEQ ID NO 9
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Val Ala Pro Phe Pro Glu Val Phe Gly Lys Glu Lys Val Asn Glu

```
            1               5                  10                 15
Leu Ser Lys Asp Ile Gly Ser Glu Ser Thr Glu Asp Gln Ala Met Glu
            20                 25                 30

Asp Ile Lys Gln Met Glu Ala Glu Ser Ile Ser Ser Ser Glu Glu Ile
            35                 40                 45

Val Pro Asn Ser Val Glu Gln Lys His Ile Gln Lys Glu Asp Val Pro
            50                 55                 60

Ser Glu Arg Tyr Leu Gly Tyr Leu Glu Gln Leu Leu Arg Leu Lys Lys
65                 70                 75                 80

Tyr Lys Val Pro Gln Leu Glu Ile Val Pro Asn Ser Ala Glu Glu Arg
            85                 90                 95

Leu His Ser Met Lys Glu Gly Ile His Ala Gln Gln Lys Glu Pro Met
            100                105                110

Ile Gly Val Asn Gln Glu Leu Ala Tyr Phe Tyr Pro Glu Leu Phe Arg
            115                120                125

Gln Phe Tyr Gln Leu Asp Ala Tyr Pro Ser Gly Ala Trp Tyr Tyr Val
            130                135                140

Pro Leu Gly Thr Gln Tyr Thr Asp Ala Pro Ser Phe Ser Asp Ile Pro
145                150                155                160

Asn Pro Ile Gly Ser Glu Asn Ser Gly Lys Thr Thr Met Pro Leu Trp
            165                170                175
```

<210> SEQ ID NO 10
<211> LENGTH: 174
<212> TYPE: PRT
<213> ORGANISM: Bos taurus

<400> SEQUENCE: 10

```
Ala Pro Phe Pro Glu Val Phe Gly Lys Glu Lys Val Asn Glu Leu Ser
1               5                  10                 15

Lys Asp Ile Gly Ser Glu Ser Thr Glu Asp Gln Ala Met Glu Asp Ile
            20                 25                 30

Lys Gln Met Glu Ala Glu Ser Ile Ser Ser Ser Glu Glu Ile Val Pro
            35                 40                 45

Asn Ser Val Glu Gln Lys His Ile Gln Lys Glu Asp Val Pro Ser Glu
            50                 55                 60

Arg Tyr Leu Gly Tyr Leu Glu Gln Leu Leu Arg Leu Lys Lys Tyr Lys
65                 70                 75                 80

Val Pro Gln Leu Glu Ile Val Pro Asn Ser Ala Glu Glu Arg Leu His
            85                 90                 95

Ser Met Lys Glu Gly Ile His Ala Gln Gln Lys Glu Pro Met Ile Gly
            100                105                110

Val Asn Gln Glu Leu Ala Tyr Phe Tyr Pro Glu Leu Phe Arg Gln Phe
            115                120                125

Tyr Gln Leu Asp Ala Tyr Pro Ser Gly Ala Trp Tyr Tyr Val Pro Leu
            130                135                140

Gly Thr Gln Tyr Thr Asp Ala Pro Ser Phe Ser Asp Ile Pro Asn Pro
145                150                155                160

Ile Gly Ser Glu Asn Ser Gly Lys Thr Thr Met Pro Leu Trp
            165                170
```

<210> SEQ ID NO 11
<211> LENGTH: 175
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 11

Met Ala Pro Phe Pro Glu Val Phe Gly Lys Glu Lys Val Asn Glu Leu
1               5                   10                  15

Ser Lys Asp Ile Gly Ser Glu Ser Thr Glu Asp Gln Ala Met Glu Asp
            20                  25                  30

Ile Lys Gln Met Glu Ala Glu Ser Ile Ser Ser Glu Glu Ile Val
        35                  40                  45

Pro Asn Ser Val Glu Gln Lys His Ile Gln Lys Glu Asp Val Pro Ser
    50                  55                  60

Glu Arg Tyr Leu Gly Tyr Leu Glu Gln Leu Leu Arg Leu Lys Lys Tyr
65                  70                  75                  80

Lys Val Pro Gln Leu Glu Ile Val Pro Asn Ser Ala Glu Glu Arg Leu
                85                  90                  95

His Ser Met Lys Glu Gly Ile His Ala Gln Gln Lys Glu Pro Met Ile
            100                 105                 110

Gly Val Asn Gln Glu Leu Ala Tyr Phe Tyr Pro Glu Leu Phe Arg Gln
        115                 120                 125

Phe Tyr Gln Leu Asp Ala Tyr Pro Ser Gly Ala Trp Tyr Tyr Val Pro
130                 135                 140

Leu Gly Thr Gln Tyr Thr Asp Ala Pro Ser Phe Ser Asp Ile Pro Asn
145                 150                 155                 160

Pro Ile Gly Ser Glu Asn Ser Gly Lys Thr Thr Met Pro Leu Trp
                165                 170                 175

<210> SEQ ID NO 12
<211> LENGTH: 140
<212> TYPE: PRT
<213> ORGANISM: Bos taurus

<400> SEQUENCE: 12

Met Glu Ala Glu Ser Ile Ser Ser Glu Glu Ile Val Pro Asn Ser
1               5                   10                  15

Val Glu Gln Lys His Ile Gln Lys Glu Asp Val Pro Ser Glu Arg Tyr
            20                  25                  30

Leu Gly Tyr Leu Glu Gln Leu Leu Arg Leu Lys Lys Tyr Lys Val Pro
        35                  40                  45

Gln Leu Glu Ile Val Pro Asn Ser Ala Glu Glu Arg Leu His Ser Met
    50                  55                  60

Lys Glu Gly Ile His Ala Gln Gln Lys Glu Pro Met Ile Gly Val Asn
65                  70                  75                  80

Gln Glu Leu Ala Tyr Phe Tyr Pro Glu Leu Phe Arg Gln Phe Tyr Gln
                85                  90                  95

Leu Asp Ala Tyr Pro Ser Gly Ala Trp Tyr Tyr Val Pro Leu Gly Thr
            100                 105                 110

Gln Tyr Thr Asp Ala Pro Ser Phe Ser Asp Ile Pro Asn Pro Ile Gly
        115                 120                 125

Ser Glu Asn Ser Gly Lys Thr Thr Met Pro Leu Trp
130                 135                 140

<210> SEQ ID NO 13
<211> LENGTH: 214
<212> TYPE: PRT
<213> ORGANISM: Ovis sp.

```
<400> SEQUENCE: 13

Met Lys Leu Leu Ile Leu Thr Cys Leu Val Ala Val Ala Leu Ala Arg
1               5                   10                  15

Pro Lys His Pro Ile Lys His Gln Gly Leu Ser Ser Glu Val Leu Asn
            20                  25                  30

Glu Asn Leu Leu Arg Phe Val Val Ala Pro Phe Pro Glu Val Phe Arg
        35                  40                  45

Lys Glu Asn Ile Asn Glu Leu Ser Lys Asp Ile Gly Ser Glu Ser Ile
    50                  55                  60

Glu Asp Gln Ala Met Glu Asp Ala Lys Gln Met Lys Ala Gly Ser Ser
65                  70                  75                  80

Ser Ser Ser Glu Glu Ile Val Pro Asn Ser Ala Glu Gln Lys Tyr Ile
                85                  90                  95

Gln Lys Glu Asp Val Pro Ser Glu Arg Tyr Leu Gly Tyr Leu Glu Gln
            100                 105                 110

Leu Leu Arg Leu Lys Lys Tyr Asn Val Pro Gln Leu Glu Ile Val Pro
        115                 120                 125

Lys Ser Ala Glu Glu Gln Leu His Ser Met Lys Glu Gly Asn Pro Ala
    130                 135                 140

His Gln Lys Gln Pro Met Ile Ala Val Asn Gln Glu Leu Ala Tyr Phe
145                 150                 155                 160

Tyr Pro Gln Leu Phe Arg Gln Phe Tyr Gln Leu Asp Ala Tyr Pro Ser
                165                 170                 175

Gly Ala Trp Tyr Tyr Leu Pro Leu Gly Thr Gln Tyr Thr Asp Ala Pro
            180                 185                 190

Ser Phe Ser Asp Ile Pro Asn Pro Ile Gly Ser Glu Asn Ser Gly Lys
        195                 200                 205

Ile Thr Met Pro Leu Trp
    210

<210> SEQ ID NO 14
<211> LENGTH: 199
<212> TYPE: PRT
<213> ORGANISM: Ovis sp.

<400> SEQUENCE: 14

Arg Pro Lys His Pro Ile Lys His Gln Gly Leu Ser Ser Glu Val Leu
1               5                   10                  15

Asn Glu Asn Leu Leu Arg Phe Val Val Ala Pro Phe Pro Glu Val Phe
            20                  25                  30

Arg Lys Glu Asn Ile Asn Glu Leu Ser Lys Asp Ile Gly Ser Glu Ser
        35                  40                  45

Ile Glu Asp Gln Ala Met Glu Asp Ala Lys Gln Met Lys Ala Gly Ser
    50                  55                  60

Ser Ser Ser Ser Glu Glu Ile Val Pro Asn Ser Ala Glu Gln Lys Tyr
65                  70                  75                  80

Ile Gln Lys Glu Asp Val Pro Ser Glu Arg Tyr Leu Gly Tyr Leu Glu
                85                  90                  95

Gln Leu Leu Arg Leu Lys Lys Tyr Asn Val Pro Gln Leu Glu Ile Val
            100                 105                 110

Pro Lys Ser Ala Glu Glu Gln Leu His Ser Met Lys Glu Gly Asn Pro
        115                 120                 125

Ala His Gln Lys Gln Pro Met Ile Ala Val Asn Gln Glu Leu Ala Tyr
    130                 135                 140
```

```
Phe Tyr Pro Gln Leu Phe Arg Gln Phe Tyr Gln Leu Asp Ala Tyr Pro
145                 150                 155                 160

Ser Gly Ala Trp Tyr Tyr Leu Pro Leu Gly Thr Gln Tyr Thr Asp Ala
                165                 170                 175

Pro Ser Phe Ser Asp Ile Pro Asn Pro Ile Gly Ser Glu Asn Ser Gly
            180                 185                 190

Lys Ile Thr Met Pro Leu Trp
        195
```

<210> SEQ ID NO 15
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Met Arg Pro Lys His Pro Ile Lys His Gln Gly Leu Ser Ser Glu Val
1               5                   10                  15

Leu Asn Glu Asn Leu Leu Arg Phe Val Val Ala Pro Phe Pro Glu Val
            20                  25                  30

Phe Arg Lys Glu Asn Ile Asn Glu Leu Ser Lys Asp Ile Gly Ser Glu
        35                  40                  45

Ser Ile Glu Asp Gln Ala Met Glu Asp Ala Lys Gln Met Lys Ala Gly
50                  55                  60

Ser Ser Ser Ser Glu Glu Ile Val Pro Asn Ser Ala Glu Gln Lys
65                  70                  75                  80

Tyr Ile Gln Lys Glu Asp Val Pro Ser Glu Arg Tyr Leu Gly Tyr Leu
                85                  90                  95

Glu Gln Leu Leu Arg Leu Lys Lys Tyr Asn Val Pro Gln Leu Glu Ile
            100                 105                 110

Val Pro Lys Ser Ala Glu Glu Gln Leu His Ser Met Lys Glu Gly Asn
        115                 120                 125

Pro Ala His Gln Lys Gln Pro Met Ile Ala Val Asn Gln Glu Leu Ala
130                 135                 140

Tyr Phe Tyr Pro Gln Leu Phe Arg Gln Phe Tyr Gln Leu Asp Ala Tyr
145                 150                 155                 160

Pro Ser Gly Ala Trp Tyr Tyr Leu Pro Leu Gly Thr Gln Tyr Thr Asp
                165                 170                 175

Ala Pro Ser Phe Ser Asp Ile Pro Asn Pro Ile Gly Ser Glu Asn Ser
            180                 185                 190

Gly Lys Ile Thr Met Pro Leu Trp
        195                 200
```

<210> SEQ ID NO 16
<211> LENGTH: 177
<212> TYPE: PRT
<213> ORGANISM: Ovis sp.

<400> SEQUENCE: 16

```
Phe Val Val Ala Pro Phe Pro Glu Val Phe Arg Lys Glu Asn Ile Asn
1               5                   10                  15

Glu Leu Ser Lys Asp Ile Gly Ser Glu Ser Ile Glu Asp Gln Ala Met
            20                  25                  30

Glu Asp Ala Lys Gln Met Lys Ala Gly Ser Ser Ser Ser Ser Glu Glu
        35                  40                  45
```

```
Ile Val Pro Asn Ser Ala Glu Gln Lys Tyr Ile Gln Lys Glu Asp Val
 50                  55                  60

Pro Ser Glu Arg Tyr Leu Gly Tyr Leu Glu Gln Leu Leu Arg Leu Lys
 65                  70                  75                  80

Lys Tyr Asn Val Pro Gln Leu Glu Ile Val Pro Lys Ser Ala Glu Glu
                 85                  90                  95

Gln Leu His Ser Met Lys Glu Gly Asn Pro Ala His Gln Lys Gln Pro
                100                 105                 110

Met Ile Ala Val Asn Gln Glu Leu Ala Tyr Phe Tyr Pro Gln Leu Phe
                115                 120                 125

Arg Gln Phe Tyr Gln Leu Asp Ala Tyr Pro Ser Gly Ala Trp Tyr Tyr
130                 135                 140

Leu Pro Leu Gly Thr Gln Tyr Thr Asp Ala Pro Ser Phe Ser Asp Ile
145                 150                 155                 160

Pro Asn Pro Ile Gly Ser Glu Asn Ser Gly Lys Ile Thr Met Pro Leu
                165                 170                 175

Trp

<210> SEQ ID NO 17
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Phe Val Val Ala Pro Phe Pro Glu Val Phe Arg Lys Glu Asn Ile
  1               5                  10                  15

Asn Glu Leu Ser Lys Asp Ile Gly Ser Glu Ser Ile Glu Asp Gln Ala
                 20                  25                  30

Met Glu Asp Ala Lys Gln Met Lys Ala Gly Ser Ser Ser Ser Ser Glu
                 35                  40                  45

Glu Ile Val Pro Asn Ser Ala Glu Gln Lys Tyr Ile Gln Lys Glu Asp
 50                  55                  60

Val Pro Ser Glu Arg Tyr Leu Gly Tyr Leu Glu Gln Leu Leu Arg Leu
 65                  70                  75                  80

Lys Lys Tyr Asn Val Pro Gln Leu Glu Ile Val Pro Lys Ser Ala Glu
                 85                  90                  95

Glu Gln Leu His Ser Met Lys Glu Gly Asn Pro Ala His Gln Lys Gln
                100                 105                 110

Pro Met Ile Ala Val Asn Gln Glu Leu Ala Tyr Phe Tyr Pro Gln Leu
                115                 120                 125

Phe Arg Gln Phe Tyr Gln Leu Asp Ala Tyr Pro Ser Gly Ala Trp Tyr
130                 135                 140

Tyr Leu Pro Leu Gly Thr Gln Tyr Thr Asp Ala Pro Ser Phe Ser Asp
145                 150                 155                 160

Ile Pro Asn Pro Ile Gly Ser Glu Asn Ser Gly Lys Ile Thr Met Pro
                165                 170                 175

Leu Trp

<210> SEQ ID NO 18
<211> LENGTH: 176
<212> TYPE: PRT
<213> ORGANISM: Ovis sp.

<400> SEQUENCE: 18
```

Val Val Ala Pro Phe Pro Glu Val Phe Arg Lys Glu Asn Ile Asn Glu
1               5                   10                  15

Leu Ser Lys Asp Ile Gly Ser Glu Ser Ile Glu Asp Gln Ala Met Glu
            20                  25                  30

Asp Ala Lys Gln Met Lys Ala Gly Ser Ser Ser Ser Glu Glu Ile
            35                  40                  45

Val Pro Asn Ser Ala Glu Gln Lys Tyr Ile Gln Lys Glu Asp Val Pro
50                  55                  60

Ser Glu Arg Tyr Leu Gly Tyr Leu Glu Gln Leu Leu Arg Leu Lys Lys
65                  70                  75                  80

Tyr Asn Val Pro Gln Leu Glu Ile Val Pro Lys Ser Ala Glu Glu Gln
                85                  90                  95

Leu His Ser Met Lys Glu Gly Asn Pro Ala His Gln Lys Gln Pro Met
            100                 105                 110

Ile Ala Val Asn Gln Glu Leu Ala Tyr Phe Tyr Pro Gln Leu Phe Arg
            115                 120                 125

Gln Phe Tyr Gln Leu Asp Ala Tyr Pro Ser Gly Ala Trp Tyr Tyr Leu
            130                 135                 140

Pro Leu Gly Thr Gln Tyr Thr Asp Ala Pro Ser Phe Ser Asp Ile Pro
145                 150                 155                 160

Asn Pro Ile Gly Ser Glu Asn Ser Gly Lys Ile Thr Met Pro Leu Trp
                165                 170                 175

<210> SEQ ID NO 19
<211> LENGTH: 177
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Val Val Ala Pro Phe Pro Glu Val Phe Arg Lys Glu Asn Ile Asn
1               5                   10                  15

Glu Leu Ser Lys Asp Ile Gly Ser Glu Ser Ile Glu Asp Gln Ala Met
            20                  25                  30

Glu Asp Ala Lys Gln Met Lys Ala Gly Ser Ser Ser Ser Glu Glu
            35                  40                  45

Ile Val Pro Asn Ser Ala Glu Gln Lys Tyr Ile Gln Lys Glu Asp Val
            50                  55                  60

Pro Ser Glu Arg Tyr Leu Gly Tyr Leu Glu Gln Leu Leu Arg Leu Lys
65                  70                  75                  80

Lys Tyr Asn Val Pro Gln Leu Glu Ile Val Pro Lys Ser Ala Glu Glu
                85                  90                  95

Gln Leu His Ser Met Lys Glu Gly Asn Pro Ala His Gln Lys Gln Pro
            100                 105                 110

Met Ile Ala Val Asn Gln Glu Leu Ala Tyr Phe Tyr Pro Gln Leu Phe
            115                 120                 125

Arg Gln Phe Tyr Gln Leu Asp Ala Tyr Pro Ser Gly Ala Trp Tyr Tyr
            130                 135                 140

Leu Pro Leu Gly Thr Gln Tyr Thr Asp Ala Pro Ser Phe Ser Asp Ile
145                 150                 155                 160

Pro Asn Pro Ile Gly Ser Glu Asn Ser Gly Lys Ile Thr Met Pro Leu
                165                 170                 175

Trp

<210> SEQ ID NO 20
<211> LENGTH: 175
<212> TYPE: PRT
<213> ORGANISM: Ovis sp.

<400> SEQUENCE: 20

```
Val Ala Pro Phe Pro Glu Val Phe Arg Lys Glu Asn Ile Asn Glu Leu
1               5                   10                  15

Ser Lys Asp Ile Gly Ser Glu Ser Ile Glu Asp Gln Ala Met Glu Asp
            20                  25                  30

Ala Lys Gln Met Lys Ala Gly Ser Ser Ser Ser Glu Glu Ile Val
        35                  40                  45

Pro Asn Ser Ala Glu Gln Lys Tyr Ile Gln Lys Glu Asp Val Pro Ser
50                  55                  60

Glu Arg Tyr Leu Gly Tyr Leu Glu Gln Leu Leu Arg Leu Lys Lys Tyr
65                  70                  75                  80

Asn Val Pro Gln Leu Glu Ile Val Pro Lys Ser Ala Glu Glu Gln Leu
                85                  90                  95

His Ser Met Lys Glu Gly Asn Pro Ala His Gln Lys Gln Pro Met Ile
            100                 105                 110

Ala Val Asn Gln Glu Leu Ala Tyr Phe Tyr Pro Gln Leu Phe Arg Gln
        115                 120                 125

Phe Tyr Gln Leu Asp Ala Tyr Pro Ser Gly Ala Trp Tyr Tyr Leu Pro
130                 135                 140

Leu Gly Thr Gln Tyr Thr Asp Ala Pro Ser Phe Ser Asp Ile Pro Asn
145                 150                 155                 160

Pro Ile Gly Ser Glu Asn Ser Gly Lys Ile Thr Met Pro Leu Trp
                165                 170                 175
```

<210> SEQ ID NO 21
<211> LENGTH: 176
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

```
Met Val Ala Pro Phe Pro Glu Val Phe Arg Lys Glu Asn Ile Asn Glu
1               5                   10                  15

Leu Ser Lys Asp Ile Gly Ser Glu Ser Ile Glu Asp Gln Ala Met Glu
            20                  25                  30

Asp Ala Lys Gln Met Lys Ala Gly Ser Ser Ser Ser Glu Glu Ile
        35                  40                  45

Val Pro Asn Ser Ala Glu Gln Lys Tyr Ile Gln Lys Glu Asp Val Pro
    50                  55                  60

Ser Glu Arg Tyr Leu Gly Tyr Leu Glu Gln Leu Leu Arg Leu Lys Lys
65                  70                  75                  80

Tyr Asn Val Pro Gln Leu Glu Ile Val Pro Lys Ser Ala Glu Glu Gln
                85                  90                  95

Leu His Ser Met Lys Glu Gly Asn Pro Ala His Gln Lys Gln Pro Met
            100                 105                 110

Ile Ala Val Asn Gln Glu Leu Ala Tyr Phe Tyr Pro Gln Leu Phe Arg
        115                 120                 125

Gln Phe Tyr Gln Leu Asp Ala Tyr Pro Ser Gly Ala Trp Tyr Tyr Leu
130                 135                 140
```

Pro Leu Gly Thr Gln Tyr Thr Asp Ala Pro Ser Phe Ser Asp Ile Pro
145                 150                 155                 160

Asn Pro Ile Gly Ser Glu Asn Ser Gly Lys Ile Thr Met Pro Leu Trp
            165                 170                 175

<210> SEQ ID NO 22
<211> LENGTH: 174
<212> TYPE: PRT
<213> ORGANISM: Ovis sp.

<400> SEQUENCE: 22

Ala Pro Phe Pro Glu Val Phe Arg Lys Glu Asn Ile Asn Glu Leu Ser
1               5                   10                  15

Lys Asp Ile Gly Ser Glu Ser Ile Glu Asp Gln Ala Met Glu Asp Ala
            20                  25                  30

Lys Gln Met Lys Ala Gly Ser Ser Ser Ser Glu Glu Ile Val Pro
        35                  40                  45

Asn Ser Ala Glu Gln Lys Tyr Ile Gln Lys Glu Asp Val Pro Ser Glu
50                  55                  60

Arg Tyr Leu Gly Tyr Leu Glu Gln Leu Leu Arg Leu Lys Lys Tyr Asn
65                  70                  75                  80

Val Pro Gln Leu Glu Ile Val Pro Lys Ser Ala Glu Glu Gln Leu His
                85                  90                  95

Ser Met Lys Glu Gly Asn Pro Ala His Gln Lys Gln Pro Met Ile Ala
            100                 105                 110

Val Asn Gln Glu Leu Ala Tyr Phe Tyr Pro Gln Leu Phe Arg Gln Phe
        115                 120                 125

Tyr Gln Leu Asp Ala Tyr Pro Ser Gly Ala Trp Tyr Tyr Leu Pro Leu
130                 135                 140

Gly Thr Gln Tyr Thr Asp Ala Pro Ser Phe Ser Asp Ile Pro Asn Pro
145                 150                 155                 160

Ile Gly Ser Glu Asn Ser Gly Lys Ile Thr Met Pro Leu Trp
            165                 170

<210> SEQ ID NO 23
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Ala Pro Phe Pro Glu Val Phe Arg Lys Glu Asn Ile Asn Glu Leu
1               5                   10                  15

Ser Lys Asp Ile Gly Ser Glu Ser Ile Glu Asp Gln Ala Met Glu Asp
            20                  25                  30

Ala Lys Gln Met Lys Ala Gly Ser Ser Ser Ser Glu Glu Ile Val
        35                  40                  45

Pro Asn Ser Ala Glu Gln Lys Tyr Ile Gln Lys Glu Asp Val Pro Ser
50                  55                  60

Glu Arg Tyr Leu Gly Tyr Leu Glu Gln Leu Leu Arg Leu Lys Lys Tyr
65                  70                  75                  80

Asn Val Pro Gln Leu Glu Ile Val Pro Lys Ser Ala Glu Glu Gln Leu
                85                  90                  95

His Ser Met Lys Glu Gly Asn Pro Ala His Gln Lys Gln Pro Met Ile
            100                 105                 110

```
Ala Val Asn Gln Glu Leu Ala Tyr Phe Tyr Pro Gln Leu Phe Arg Gln
        115                 120                 125

Phe Tyr Gln Leu Asp Ala Tyr Pro Ser Gly Ala Trp Tyr Tyr Leu Pro
    130                 135                 140

Leu Gly Thr Gln Tyr Thr Asp Ala Pro Ser Phe Ser Asp Ile Pro Asn
145                 150                 155                 160

Pro Ile Gly Ser Glu Asn Ser Gly Lys Ile Thr Met Pro Leu Trp
                165                 170                 175

<210> SEQ ID NO 24
<211> LENGTH: 140
<212> TYPE: PRT
<213> ORGANISM: Ovis sp.

<400> SEQUENCE: 24

Met Lys Ala Gly Ser Ser Ser Ser Glu Glu Ile Val Pro Asn Ser
1               5                   10                  15

Ala Glu Gln Lys Tyr Ile Gln Lys Glu Asp Val Pro Ser Glu Arg Tyr
            20                  25                  30

Leu Gly Tyr Leu Glu Gln Leu Leu Arg Leu Lys Lys Tyr Asn Val Pro
        35                  40                  45

Gln Leu Glu Ile Val Pro Lys Ser Ala Glu Gln Leu His Ser Met
    50                  55                  60

Lys Glu Gly Asn Pro Ala His Gln Lys Gln Pro Met Ile Ala Val Asn
65                  70                  75                  80

Gln Glu Leu Ala Tyr Phe Tyr Pro Gln Leu Phe Arg Gln Phe Tyr Gln
                85                  90                  95

Leu Asp Ala Tyr Pro Ser Gly Ala Trp Tyr Tyr Leu Pro Leu Gly Thr
            100                 105                 110

Gln Tyr Thr Asp Ala Pro Ser Phe Ser Asp Ile Pro Asn Pro Ile Gly
        115                 120                 125

Ser Glu Asn Ser Gly Lys Ile Thr Met Pro Leu Trp
    130                 135                 140

<210> SEQ ID NO 25
<211> LENGTH: 214
<212> TYPE: PRT
<213> ORGANISM: Capra sp.

<400> SEQUENCE: 25

Met Lys Leu Leu Ile Leu Thr Cys Leu Val Ala Val Ala Leu Ala Arg
1               5                   10                  15

Pro Lys His Pro Ile Asn His Arg Gly Leu Ser Pro Glu Val Pro Asn
            20                  25                  30

Glu Asn Leu Leu Arg Phe Val Ala Pro Phe Pro Glu Val Phe Arg
        35                  40                  45

Lys Glu Asn Ile Asn Glu Leu Ser Lys Asp Ile Gly Ser Glu Ser Thr
    50                  55                  60

Glu Asp Gln Ala Met Glu Asp Ala Lys Gln Met Lys Ala Gly Ser Ser
65                  70                  75                  80

Ser Ser Ser Glu Glu Ile Val Pro Asn Ser Ala Glu Gln Lys Tyr Ile
                85                  90                  95

Gln Lys Glu Asp Val Pro Ser Glu Arg Tyr Leu Gly Tyr Leu Glu Gln
            100                 105                 110

Leu Leu Arg Leu Lys Lys Tyr Asn Val Pro Gln Leu Glu Ile Val Pro
        115                 120                 125
```

```
Lys Ser Ala Glu Glu Gln Leu His Ser Met Lys Gly Asn Pro Ala
    130                 135                 140

His Gln Lys Gln Pro Met Ile Ala Val Asn Gln Glu Leu Ala Tyr Phe
145                 150                 155                 160

Tyr Pro Gln Leu Phe Arg Gln Phe Tyr Gln Leu Asp Ala Tyr Pro Ser
            165                 170                 175

Gly Ala Trp Tyr Tyr Leu Pro Leu Gly Thr Gln Tyr Thr Asp Ala Pro
        180                 185                 190

Ser Phe Ser Asp Ile Pro Asn Pro Ile Gly Ser Glu Asn Ser Gly Lys
    195                 200                 205

Thr Thr Met Pro Leu Trp
    210

<210> SEQ ID NO 26
<211> LENGTH: 199
<212> TYPE: PRT
<213> ORGANISM: Capra sp.

<400> SEQUENCE: 26

Arg Pro Lys His Pro Ile Asn His Arg Gly Leu Ser Pro Glu Val Pro
1               5                   10                  15

Asn Glu Asn Leu Leu Arg Phe Val Ala Pro Phe Pro Glu Val Phe
            20                  25                  30

Arg Lys Glu Asn Ile Asn Glu Leu Ser Lys Asp Ile Gly Ser Glu Ser
        35                  40                  45

Thr Glu Asp Gln Ala Met Glu Asp Ala Lys Gln Met Lys Ala Gly Ser
50                  55                  60

Ser Ser Ser Ser Glu Glu Ile Val Pro Asn Ser Ala Glu Gln Lys Tyr
65                  70                  75                  80

Ile Gln Lys Glu Asp Val Pro Ser Glu Arg Tyr Leu Gly Tyr Leu Glu
                85                  90                  95

Gln Leu Leu Arg Leu Lys Lys Tyr Asn Val Pro Gln Leu Glu Ile Val
            100                 105                 110

Pro Lys Ser Ala Glu Glu Gln Leu His Ser Met Lys Glu Gly Asn Pro
        115                 120                 125

Ala His Gln Lys Gln Pro Met Ile Ala Val Asn Gln Glu Leu Ala Tyr
    130                 135                 140

Phe Tyr Pro Gln Leu Phe Arg Gln Phe Tyr Gln Leu Asp Ala Tyr Pro
145                 150                 155                 160

Ser Gly Ala Trp Tyr Tyr Leu Pro Leu Gly Thr Gln Tyr Thr Asp Ala
                165                 170                 175

Pro Ser Phe Ser Asp Ile Pro Asn Pro Ile Gly Ser Glu Asn Ser Gly
            180                 185                 190

Lys Thr Thr Met Pro Leu Trp
        195

<210> SEQ ID NO 27
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Arg Pro Lys His Pro Ile Asn His Arg Gly Leu Ser Pro Glu Val
1               5                   10                  15
```

```
Pro Asn Glu Asn Leu Leu Arg Phe Val Ala Pro Phe Pro Glu Val
             20                  25                  30

Phe Arg Lys Glu Asn Ile Asn Glu Leu Ser Lys Asp Ile Gly Ser Glu
         35                  40                  45

Ser Thr Glu Asp Gln Ala Met Glu Asp Ala Lys Gln Met Lys Ala Gly
 50                  55                  60

Ser Ser Ser Ser Glu Glu Ile Val Pro Asn Ser Ala Glu Gln Lys
 65                  70                  75                  80

Tyr Ile Gln Lys Glu Asp Val Pro Ser Glu Arg Tyr Leu Gly Tyr Leu
                 85                  90                  95

Glu Gln Leu Leu Arg Leu Lys Lys Tyr Asn Val Pro Gln Leu Glu Ile
                100                 105                 110

Val Pro Lys Ser Ala Glu Glu Gln Leu His Ser Met Lys Glu Gly Asn
            115                 120                 125

Pro Ala His Gln Lys Gln Pro Met Ile Ala Val Asn Gln Glu Leu Ala
130                 135                 140

Tyr Phe Tyr Pro Gln Leu Phe Arg Gln Phe Tyr Gln Leu Asp Ala Tyr
145                 150                 155                 160

Pro Ser Gly Ala Trp Tyr Tyr Leu Pro Leu Gly Thr Gln Tyr Thr Asp
                165                 170                 175

Ala Pro Ser Phe Ser Asp Ile Pro Asn Pro Ile Gly Ser Glu Asn Ser
            180                 185                 190

Gly Lys Thr Thr Met Pro Leu Trp
            195                 200

<210> SEQ ID NO 28
<211> LENGTH: 214
<212> TYPE: PRT
<213> ORGANISM: Bubalus sp.

<400> SEQUENCE: 28

Met Lys Leu Leu Ile Leu Thr Cys Leu Val Ala Val Ala Leu Ala Arg
 1               5                  10                  15

Pro Lys Gln Pro Ile Lys His Gln Gly Leu Pro Gln Gly Val Leu Asn
             20                  25                  30

Glu Asn Leu Leu Arg Phe Phe Val Ala Pro Phe Pro Glu Val Phe Gly
         35                  40                  45

Lys Glu Lys Val Asn Glu Leu Ser Thr Asp Ile Gly Ser Glu Ser Thr
 50                  55                  60

Glu Asp Gln Ala Met Glu Asp Ile Lys Gln Met Glu Ala Glu Ser Ile
 65                  70                  75                  80

Ser Ser Ser Glu Glu Ile Val Pro Ile Ser Val Glu Gln Lys His Ile
                 85                  90                  95

Gln Lys Glu Asp Val Pro Ser Glu Arg Tyr Leu Gly Tyr Leu Glu Gln
                100                 105                 110

Leu Leu Arg Leu Lys Lys Tyr Asn Val Pro Gln Leu Glu Ile Val Pro
            115                 120                 125

Asn Leu Ala Glu Glu Gln Leu His Ser Met Lys Glu Gly Ile His Ala
130                 135                 140

Gln Gln Lys Glu Pro Met Ile Gly Val Asn Gln Glu Leu Ala Tyr Phe
145                 150                 155                 160

Tyr Pro Gln Leu Phe Arg Gln Phe Tyr Gln Leu Asp Ala Tyr Pro Ser
                165                 170                 175

Gly Ala Trp Tyr Tyr Val Pro Leu Gly Thr Gln Tyr Pro Asp Ala Pro
```

```
                180             185                 190
Ser Phe Ser Asp Ile Pro Asn Pro Ile Gly Ser Glu Asn Ser Glu Lys
                195                 200                 205

Thr Thr Met Pro Leu Trp
            210
```

<210> SEQ ID NO 29
<211> LENGTH: 199
<212> TYPE: PRT
<213> ORGANISM: Bubalus sp.

<400> SEQUENCE: 29

```
Arg Pro Lys Gln Pro Ile Lys His Gln Gly Leu Pro Gln Gly Val Leu
1               5                   10                  15

Asn Glu Asn Leu Leu Arg Phe Phe Val Ala Pro Phe Pro Glu Val Phe
            20                  25                  30

Gly Lys Glu Lys Val Asn Glu Leu Ser Thr Asp Ile Gly Ser Glu Ser
        35                  40                  45

Thr Glu Asp Gln Ala Met Glu Asp Ile Lys Gln Met Glu Ala Glu Ser
    50                  55                  60

Ile Ser Ser Glu Glu Ile Val Pro Ile Ser Val Glu Gln Lys His
65                  70                  75                  80

Ile Gln Lys Glu Asp Val Pro Ser Glu Arg Tyr Leu Gly Tyr Leu Glu
                85                  90                  95

Gln Leu Leu Arg Leu Lys Lys Tyr Asn Val Pro Gln Leu Glu Ile Val
            100                 105                 110

Pro Asn Leu Ala Glu Glu Leu His Ser Met Lys Glu Gly Ile His
        115                 120                 125

Ala Gln Gln Lys Glu Pro Met Ile Gly Val Asn Gln Glu Leu Ala Tyr
    130                 135                 140

Phe Tyr Pro Gln Leu Phe Arg Gln Phe Tyr Gln Leu Asp Ala Tyr Pro
145                 150                 155                 160

Ser Gly Ala Trp Tyr Tyr Val Pro Leu Gly Thr Gln Tyr Pro Asp Ala
                165                 170                 175

Pro Ser Phe Ser Asp Ile Pro Asn Pro Ile Gly Ser Glu Asn Ser Glu
            180                 185                 190

Lys Thr Thr Met Pro Leu Trp
        195
```

<210> SEQ ID NO 30
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Met Arg Pro Lys Gln Pro Ile Lys His Gln Gly Leu Pro Gln Gly Val
1               5                   10                  15

Leu Asn Glu Asn Leu Leu Arg Phe Phe Val Ala Pro Phe Pro Glu Val
            20                  25                  30

Phe Gly Lys Glu Lys Val Asn Glu Leu Ser Thr Asp Ile Gly Ser Glu
        35                  40                  45

Ser Thr Glu Asp Gln Ala Met Glu Asp Ile Lys Gln Met Glu Ala Glu
    50                  55                  60

Ser Ile Ser Ser Ser Glu Glu Ile Val Pro Ile Ser Val Glu Gln Lys
```

```
            65                  70                  75                  80
His Ile Gln Lys Glu Asp Val Pro Ser Glu Arg Tyr Leu Gly Tyr Leu
                    85                  90                  95

Glu Gln Leu Leu Arg Leu Lys Lys Tyr Asn Val Pro Gln Leu Glu Ile
                100                 105                 110

Val Pro Asn Leu Ala Glu Glu Gln Leu His Ser Met Lys Glu Gly Ile
                115                 120                 125

His Ala Gln Gln Lys Glu Pro Met Ile Gly Val Asn Gln Glu Leu Ala
        130                 135                 140

Tyr Phe Tyr Pro Gln Leu Phe Arg Gln Phe Tyr Gln Leu Asp Ala Tyr
145                 150                 155                 160

Pro Ser Gly Ala Trp Tyr Tyr Val Pro Leu Gly Thr Gln Tyr Pro Asp
                    165                 170                 175

Ala Pro Ser Phe Ser Asp Ile Pro Asn Pro Ile Gly Ser Glu Asn Ser
                180                 185                 190

Glu Lys Thr Thr Met Pro Leu Trp
                195                 200

<210> SEQ ID NO 31
<211> LENGTH: 212
<212> TYPE: PRT
<213> ORGANISM: Equus sp.

<400> SEQUENCE: 31

Met Lys Leu Leu Ile Leu Thr Cys Leu Val Ala Val Ala Leu Ala Arg
1               5                   10                  15

Pro Lys Leu Pro His Arg Gln Pro Glu Ile Ile Gln Asn Glu Gln Asp
                20                  25                  30

Ser Arg Glu Lys Val Leu Lys Glu Arg Lys Phe Pro Ser Phe Ala Leu
            35                  40                  45

Glu Tyr Ile Asn Glu Leu Asn Arg Gln Arg Glu Leu Leu Lys Glu Lys
    50                  55                  60

Gln Lys Asp Glu His Lys Glu Tyr Leu Ile Glu Asp Pro Glu Gln Gln
65                  70                  75                  80

Glu Ser Ser Ser Thr Ser Ser Glu Glu Val Val Pro Ile Asn Thr
                85                  90                  95

Glu Gln Lys Arg Ile Pro Arg Glu Asp Met Leu Tyr Gln His Thr Leu
                100                 105                 110

Glu Gln Leu Arg Arg Leu Ser Lys Tyr Asn Gln Leu Gln Leu Gln Ala
            115                 120                 125

Ile His Ala Gln Glu Gln Leu Ile Arg Met Lys Glu Asn Ser Gln Arg
        130                 135                 140

Lys Pro Met Arg Val Val Asn Gln Glu Gln Ala Tyr Phe Tyr Leu Glu
145                 150                 155                 160

Pro Phe Gln Pro Ser Tyr Gln Leu Asp Val Tyr Pro Tyr Ala Ala Trp
                    165                 170                 175

Phe His Pro Ala Gln Ile Met Gln His Val Ala Tyr Ser Pro Phe His
                180                 185                 190

Asp Thr Ala Lys Leu Ile Ala Ser Glu Asn Ser Glu Lys Thr Asp Ile
            195                 200                 205

Ile Pro Glu Trp
        210

<210> SEQ ID NO 32
<211> LENGTH: 197
```

<212> TYPE: PRT
<213> ORGANISM: Equus sp.

<400> SEQUENCE: 32

```
Arg Pro Lys Leu Pro His Arg Gln Pro Glu Ile Ile Gln Asn Glu Gln
1               5                   10                  15

Asp Ser Arg Glu Lys Val Leu Lys Glu Arg Lys Phe Pro Ser Phe Ala
            20                  25                  30

Leu Glu Tyr Ile Asn Glu Leu Asn Arg Gln Arg Glu Leu Leu Lys Glu
        35                  40                  45

Lys Gln Lys Asp Glu His Lys Glu Tyr Leu Ile Glu Asp Pro Glu Gln
    50                  55                  60

Gln Glu Ser Ser Ser Thr Ser Ser Ser Glu Glu Val Val Pro Ile Asn
65                  70                  75                  80

Thr Glu Gln Lys Arg Ile Pro Arg Glu Asp Met Leu Tyr Gln His Thr
                85                  90                  95

Leu Glu Gln Leu Arg Arg Leu Ser Lys Tyr Asn Gln Leu Gln Leu Gln
            100                 105                 110

Ala Ile His Ala Gln Glu Gln Leu Ile Arg Met Lys Glu Asn Ser Gln
        115                 120                 125

Arg Lys Pro Met Arg Val Val Asn Gln Glu Gln Ala Tyr Phe Tyr Leu
    130                 135                 140

Glu Pro Phe Gln Pro Ser Tyr Gln Leu Asp Val Tyr Pro Tyr Ala Ala
145                 150                 155                 160

Trp Phe His Pro Ala Gln Ile Met Gln His Val Ala Tyr Ser Pro Phe
                165                 170                 175

His Asp Thr Ala Lys Leu Ile Ala Ser Glu Asn Ser Glu Lys Thr Asp
            180                 185                 190

Ile Ile Pro Glu Trp
        195
```

<210> SEQ ID NO 33
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Met Arg Pro Lys Leu Pro His Arg Gln Pro Glu Ile Ile Gln Asn Glu
1               5                   10                  15

Gln Asp Ser Arg Glu Lys Val Leu Lys Glu Arg Lys Phe Pro Ser Phe
            20                  25                  30

Ala Leu Glu Tyr Ile Asn Glu Leu Asn Arg Gln Arg Glu Leu Leu Lys
        35                  40                  45

Glu Lys Gln Lys Asp Glu His Lys Glu Tyr Leu Ile Glu Asp Pro Glu
    50                  55                  60

Gln Gln Glu Ser Ser Ser Thr Ser Ser Ser Glu Glu Val Val Pro Ile
65                  70                  75                  80

Asn Thr Glu Gln Lys Arg Ile Pro Arg Glu Asp Met Leu Tyr Gln His
                85                  90                  95

Thr Leu Glu Gln Leu Arg Arg Leu Ser Lys Tyr Asn Gln Leu Gln Leu
            100                 105                 110

Gln Ala Ile His Ala Gln Glu Gln Leu Ile Arg Met Lys Glu Asn Ser
        115                 120                 125
```

Gln Arg Lys Pro Met Arg Val Val Asn Gln Glu Gln Ala Tyr Phe Tyr
            130                 135                 140

Leu Glu Pro Phe Gln Pro Ser Tyr Gln Leu Asp Val Tyr Pro Tyr Ala
145                 150                 155                 160

Ala Trp Phe His Pro Ala Gln Ile Met Gln His Val Ala Tyr Ser Pro
                165                 170                 175

Phe His Asp Thr Ala Lys Leu Ile Ala Ser Glu Asn Ser Glu Lys Thr
            180                 185                 190

Asp Ile Ile Pro Glu Trp
        195

<210> SEQ ID NO 34
<211> LENGTH: 230
<212> TYPE: PRT
<213> ORGANISM: Camelus sp.

<400> SEQUENCE: 34

Met Lys Leu Leu Ile Leu Thr Cys Leu Val Ala Val Ala Leu Ala Arg
1               5                   10                  15

Pro Lys Tyr Pro Leu Arg Tyr Pro Glu Val Phe Gln Asn Glu Pro Asp
            20                  25                  30

Ser Ile Glu Glu Val Leu Asn Lys Arg Lys Ile Leu Glu Leu Ala Val
        35                  40                  45

Val Ser Pro Ile Gln Phe Arg Gln Glu Asn Ile Asp Glu Leu Lys Asp
50                  55                  60

Thr Arg Asn Glu Pro Thr Glu Asp His Ile Met Glu Asp Thr Glu Arg
65                  70                  75                  80

Lys Glu Ser Gly Ser Ser Ser Glu Glu Val Val Ser Ser Thr Thr Thr
                85                  90                  95

Glu Gln Lys Asp Ile Leu Lys Glu Asp Met Pro Ser Gln Arg Tyr Leu
            100                 105                 110

Glu Glu Leu His Arg Leu Asn Lys Tyr Lys Leu Leu Gln Leu Glu Ala
            115                 120                 125

Ile Arg Asp Gln Lys Leu Ile Pro Arg Val Lys Leu Ser Ser His Pro
130                 135                 140

Tyr Leu Glu Gln Leu Tyr Arg Ile Asn Glu Asp Asn His Pro Gln Leu
145                 150                 155                 160

Gly Glu Pro Val Lys Val Thr Gln Glu Gln Ala Tyr Phe His Leu
            165                 170                 175

Glu Pro Phe Pro Gln Phe Phe Gln Leu Gly Ala Ser Pro Tyr Val Ala
            180                 185                 190

Trp Tyr Tyr Pro Pro Gln Val Met Gln Tyr Ile Ala His Pro Ser Ser
        195                 200                 205

Tyr Asp Thr Pro Glu Gly Ile Ala Ser Glu Asp Gly Gly Lys Thr Asp
        210                 215                 220

Val Met Pro Gln Trp Trp
225                 230

<210> SEQ ID NO 35
<211> LENGTH: 215
<212> TYPE: PRT
<213> ORGANISM: Camelus sp.

<400> SEQUENCE: 35

Arg Pro Lys Tyr Pro Leu Arg Tyr Pro Glu Val Phe Gln Asn Glu Pro
1               5                   10                  15

```
Asp Ser Ile Glu Glu Val Leu Asn Lys Arg Lys Ile Leu Glu Leu Ala
            20                  25                  30

Val Val Ser Pro Ile Gln Phe Arg Gln Glu Asn Ile Asp Glu Leu Lys
        35                  40                  45

Asp Thr Arg Asn Glu Pro Thr Glu Asp His Ile Met Glu Asp Thr Glu
    50                  55                  60

Arg Lys Glu Ser Gly Ser Ser Ser Glu Val Val Ser Ser Thr
65                  70                  75                  80

Thr Glu Gln Lys Asp Ile Leu Lys Glu Asp Met Pro Ser Gln Arg Tyr
                85                  90                  95

Leu Glu Glu Leu His Arg Leu Asn Lys Tyr Lys Leu Leu Gln Leu Glu
            100                 105                 110

Ala Ile Arg Asp Gln Lys Leu Ile Pro Arg Val Lys Leu Ser Ser His
        115                 120                 125

Pro Tyr Leu Glu Gln Leu Tyr Arg Ile Asn Glu Asp Asn His Pro Gln
    130                 135                 140

Leu Gly Glu Pro Val Lys Val Val Thr Gln Glu Gln Ala Tyr Phe His
145                 150                 155                 160

Leu Glu Pro Phe Pro Gln Phe Gln Leu Gly Ala Ser Pro Tyr Val
                165                 170                 175

Ala Trp Tyr Tyr Pro Pro Gln Val Met Gln Tyr Ile Ala His Pro Ser
            180                 185                 190

Ser Tyr Asp Thr Pro Glu Gly Ile Ala Ser Glu Asp Gly Gly Lys Thr
        195                 200                 205

Asp Val Met Pro Gln Trp Trp
    210                 215

<210> SEQ ID NO 36
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Arg Pro Lys Tyr Pro Leu Arg Tyr Pro Glu Val Phe Gln Asn Glu
1               5                   10                  15

Pro Asp Ser Ile Glu Glu Val Leu Asn Lys Arg Lys Ile Leu Glu Leu
            20                  25                  30

Ala Val Val Ser Pro Ile Gln Phe Arg Gln Glu Asn Ile Asp Glu Leu
        35                  40                  45

Lys Asp Thr Arg Asn Glu Pro Thr Glu Asp His Ile Met Glu Asp Thr
    50                  55                  60

Glu Arg Lys Glu Ser Gly Ser Ser Ser Glu Val Val Ser Ser
65                  70                  75                  80

Thr Thr Glu Gln Lys Asp Ile Leu Lys Glu Asp Met Pro Ser Gln Arg
                85                  90                  95

Tyr Leu Glu Glu Leu His Arg Leu Asn Lys Tyr Lys Leu Leu Gln Leu
            100                 105                 110

Glu Ala Ile Arg Asp Gln Lys Leu Ile Pro Arg Val Lys Leu Ser Ser
        115                 120                 125

His Pro Tyr Leu Glu Gln Leu Tyr Arg Ile Asn Glu Asp Asn His Pro
    130                 135                 140

Gln Leu Gly Glu Pro Val Lys Val Val Thr Gln Glu Gln Ala Tyr Phe
145                 150                 155                 160
```

His Leu Glu Pro Phe Pro Gln Phe Phe Gln Leu Gly Ala Ser Pro Tyr
                165                 170                 175
Val Ala Trp Tyr Tyr Pro Pro Gln Val Met Gln Tyr Ile Ala His Pro
            180                 185                 190
Ser Ser Tyr Asp Thr Pro Glu Gly Ile Ala Ser Glu Asp Gly Gly Lys
        195                 200                 205
Thr Asp Val Met Pro Gln Trp Trp
    210                 215

<210> SEQ ID NO 37
<211> LENGTH: 185
<212> TYPE: PRT
<213> ORGANISM: Homo sapiens

<400> SEQUENCE: 37

Met Arg Leu Leu Ile Leu Thr Cys Leu Val Ala Val Ala Leu Ala Arg
1               5                   10                  15
Pro Lys Leu Pro Leu Arg Tyr Pro Glu Arg Leu Gln Asn Pro Ser Glu
            20                  25                  30
Ser Ser Glu Pro Ile Pro Leu Glu Ser Arg Glu Glu Tyr Met Asn Gly
        35                  40                  45
Met Asn Arg Gln Arg Asn Ile Leu Arg Glu Lys Gln Thr Asp Glu Ile
    50                  55                  60
Lys Asp Thr Arg Asn Glu Ser Thr Gln Asn Cys Val Val Ala Glu Pro
65                  70                  75                  80
Glu Lys Met Glu Ser Ser Ile Ser Ser Ser Glu Glu Met Ser Leu
                85                  90                  95
Ser Lys Cys Ala Glu Gln Phe Cys Arg Leu Asn Glu Tyr Asn Gln Leu
            100                 105                 110
Gln Leu Gln Ala Ala His Ala Gln Glu Gln Ile Arg Arg Met Asn Glu
        115                 120                 125
Asn Ser His Val Gln Val Pro Phe Gln Gln Leu Asn Gln Leu Ala Ala
    130                 135                 140
Tyr Pro Tyr Ala Val Trp Tyr Tyr Pro Gln Ile Met Gln Tyr Val Pro
145                 150                 155                 160
Phe Pro Pro Phe Ser Asp Ile Ser Asn Pro Thr Ala His Glu Asn Tyr
                165                 170                 175
Glu Lys Asn Asn Val Met Leu Gln Trp
            180                 185

<210> SEQ ID NO 38
<211> LENGTH: 170
<212> TYPE: PRT
<213> ORGANISM: Homo sapiens

<400> SEQUENCE: 38

Arg Pro Lys Leu Pro Leu Arg Tyr Pro Glu Arg Leu Gln Asn Pro Ser
1               5                   10                  15
Glu Ser Ser Glu Pro Ile Pro Leu Glu Ser Arg Glu Glu Tyr Met Asn
            20                  25                  30
Gly Met Asn Arg Gln Arg Asn Ile Leu Arg Glu Lys Gln Thr Asp Glu
        35                  40                  45
Ile Lys Asp Thr Arg Asn Glu Ser Thr Gln Asn Cys Val Val Ala Glu
    50                  55                  60
Pro Glu Lys Met Glu Ser Ser Ile Ser Ser Ser Ser Glu Glu Met Ser
65                  70                  75                  80

```
Leu Ser Lys Cys Ala Glu Gln Phe Cys Arg Leu Asn Glu Tyr Asn Gln
                85                  90                  95

Leu Gln Leu Gln Ala Ala His Ala Gln Glu Gln Ile Arg Arg Met Asn
            100                 105                 110

Glu Asn Ser His Val Gln Val Pro Phe Gln Leu Asn Gln Leu Ala
        115                 120                 125

Ala Tyr Pro Tyr Ala Val Trp Tyr Tyr Pro Gln Ile Met Gln Tyr Val
    130                 135                 140

Pro Phe Pro Pro Phe Ser Asp Ile Ser Asn Pro Thr Ala His Glu Asn
145                 150                 155                 160

Tyr Glu Lys Asn Asn Val Met Leu Gln Trp
            165                 170

<210> SEQ ID NO 39
<211> LENGTH: 222
<212> TYPE: PRT
<213> ORGANISM: Bos taurus

<400> SEQUENCE: 39

Met Lys Phe Phe Ile Phe Thr Cys Leu Leu Ala Val Ala Leu Ala Lys
1               5                   10                  15

Asn Thr Met Glu His Val Ser Ser Ser Glu Glu Ser Ile Ile Ser Gln
            20                  25                  30

Glu Thr Tyr Lys Gln Glu Lys Asn Met Ala Ile Asn Pro Ser Lys Glu
        35                  40                  45

Asn Leu Cys Ser Thr Phe Cys Lys Glu Val Val Arg Asn Ala Asn Glu
50                  55                  60

Glu Glu Tyr Ser Ile Gly Ser Ser Ser Glu Glu Ser Ala Glu Val Ala
65                  70                  75                  80

Thr Glu Glu Val Lys Ile Thr Val Asp Asp Lys His Tyr Gln Lys Ala
                85                  90                  95

Leu Asn Glu Ile Asn Gln Phe Tyr Gln Lys Phe Pro Gln Tyr Leu Gln
            100                 105                 110

Tyr Leu Tyr Gln Gly Pro Ile Val Leu Asn Pro Trp Asp Gln Val Lys
        115                 120                 125

Arg Asn Ala Val Pro Ile Thr Pro Thr Leu Asn Arg Glu Gln Leu Ser
130                 135                 140

Thr Ser Glu Glu Asn Ser Lys Lys Thr Val Asp Met Glu Ser Thr Glu
145                 150                 155                 160

Val Phe Thr Lys Lys Thr Lys Leu Thr Glu Glu Glu Lys Asn Arg Leu
                165                 170                 175

Asn Phe Leu Lys Lys Ile Ser Gln Arg Tyr Gln Lys Phe Ala Leu Pro
            180                 185                 190

Gln Tyr Leu Lys Thr Val Tyr Gln His Gln Lys Ala Met Lys Pro Trp
        195                 200                 205

Ile Gln Pro Lys Thr Lys Val Ile Pro Tyr Val Arg Tyr Leu
210                 215                 220

<210> SEQ ID NO 40
<211> LENGTH: 207
<212> TYPE: PRT
<213> ORGANISM: Bos taurus

<400> SEQUENCE: 40

Lys Asn Thr Met Glu His Val Ser Ser Ser Glu Glu Ser Ile Ile Ser
1               5                   10                  15
```

Gln Glu Thr Tyr Lys Gln Glu Lys Asn Met Ala Ile Asn Pro Ser Lys
            20                  25                  30

Glu Asn Leu Cys Ser Thr Phe Cys Lys Glu Val Val Arg Asn Ala Asn
            35                  40                  45

Glu Glu Glu Tyr Ser Ile Gly Ser Ser Glu Glu Ser Ala Glu Val
        50                  55                  60

Ala Thr Glu Glu Val Lys Ile Thr Val Asp Asp Lys His Tyr Gln Lys
65                  70                  75                  80

Ala Leu Asn Glu Ile Asn Gln Phe Tyr Gln Lys Phe Pro Gln Tyr Leu
                85                  90                  95

Gln Tyr Leu Tyr Gln Gly Pro Ile Val Leu Asn Pro Trp Asp Gln Val
            100                 105                 110

Lys Arg Asn Ala Val Pro Ile Thr Pro Thr Leu Asn Arg Glu Gln Leu
            115                 120                 125

Ser Thr Ser Glu Glu Asn Ser Lys Lys Thr Val Asp Met Glu Ser Thr
130                 135                 140

Glu Val Phe Thr Lys Lys Thr Lys Leu Thr Glu Glu Lys Asn Arg
145                 150                 155                 160

Leu Asn Phe Leu Lys Lys Ile Ser Gln Arg Tyr Gln Lys Phe Ala Leu
                165                 170                 175

Pro Gln Tyr Leu Lys Thr Val Tyr Gln His Gln Lys Ala Met Lys Pro
            180                 185                 190

Trp Ile Gln Pro Lys Thr Lys Val Ile Pro Tyr Val Arg Tyr Leu
            195                 200                 205

<210> SEQ ID NO 41
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Lys Asn Thr Met Glu His Val Ser Ser Ser Glu Glu Ser Ile Ile
1               5                   10                  15

Ser Gln Glu Thr Tyr Lys Gln Glu Lys Asn Met Ala Ile Asn Pro Ser
            20                  25                  30

Lys Glu Asn Leu Cys Ser Thr Phe Cys Lys Glu Val Val Arg Asn Ala
            35                  40                  45

Asn Glu Glu Glu Tyr Ser Ile Gly Ser Ser Glu Glu Ser Ala Glu
        50                  55                  60

Val Ala Thr Glu Glu Val Lys Ile Thr Val Asp Asp Lys His Tyr Gln
65                  70                  75                  80

Lys Ala Leu Asn Glu Ile Asn Gln Phe Tyr Gln Lys Phe Pro Gln Tyr
                85                  90                  95

Leu Gln Tyr Leu Tyr Gln Gly Pro Ile Val Leu Asn Pro Trp Asp Gln
            100                 105                 110

Val Lys Arg Asn Ala Val Pro Ile Thr Pro Thr Leu Asn Arg Glu Gln
            115                 120                 125

Leu Ser Thr Ser Glu Glu Asn Ser Lys Lys Thr Val Asp Met Glu Ser
        130                 135                 140

Thr Glu Val Phe Thr Lys Lys Thr Lys Leu Thr Glu Glu Lys Asn
145                 150                 155                 160

Arg Leu Asn Phe Leu Lys Lys Ile Ser Gln Arg Tyr Gln Lys Phe Ala

```
                    165                 170                 175
Leu Pro Gln Tyr Leu Lys Thr Val Tyr Gln His Gln Lys Ala Met Lys
                180                 185                 190
Pro Trp Ile Gln Pro Lys Thr Lys Val Ile Pro Tyr Val Arg Tyr Leu
            195                 200                 205

<210> SEQ ID NO 42
<211> LENGTH: 223
<212> TYPE: PRT
<213> ORGANISM: Ovis sp.

<400> SEQUENCE: 42

Met Lys Phe Phe Ile Phe Thr Cys Leu Leu Ala Val Ala Leu Ala Lys
1               5                   10                  15
His Lys Met Glu His Val Ser Ser Glu Glu Pro Ile Asn Ile Ser
            20                  25                  30
Gln Glu Ile Tyr Lys Gln Glu Lys Asn Met Ala Ile His Pro Arg Lys
        35                  40                  45
Glu Lys Leu Cys Thr Thr Ser Cys Glu Glu Val Val Arg Asn Ala Asp
    50                  55                  60
Glu Glu Glu Tyr Ser Ile Arg Ser Ser Glu Glu Ser Ala Glu Val
65                  70                  75                  80
Ala Pro Glu Glu Val Lys Ile Thr Val Asp Asp Lys His Tyr Gln Lys
                85                  90                  95
Ala Leu Asn Glu Ile Asn Gln Phe Tyr Gln Lys Phe Pro Gln Tyr Leu
            100                 105                 110
Gln Tyr Leu Tyr Gln Gly Pro Ile Val Leu Asn Pro Trp Asp Gln Val
        115                 120                 125
Lys Arg Asn Ala Gly Pro Phe Thr Pro Thr Val Asn Arg Glu Gln Leu
    130                 135                 140
Ser Thr Ser Glu Glu Asn Ser Lys Lys Thr Ile Asp Met Glu Ser Thr
145                 150                 155                 160
Glu Val Phe Thr Lys Lys Thr Lys Leu Thr Glu Glu Lys Asn Arg
                165                 170                 175
Leu Asn Phe Leu Lys Lys Ile Ser Gln Tyr Tyr Gln Lys Phe Ala Trp
            180                 185                 190
Pro Gln Tyr Leu Lys Thr Val Asp Gln His Gln Lys Ala Met Lys Pro
        195                 200                 205
Trp Thr Gln Pro Lys Thr Asn Ala Ile Pro Tyr Val Arg Tyr Leu
    210                 215                 220

<210> SEQ ID NO 43
<211> LENGTH: 208
<212> TYPE: PRT
<213> ORGANISM: Ovis sp.

<400> SEQUENCE: 43

Lys His Lys Met Glu His Val Ser Ser Glu Glu Pro Ile Asn Ile
1               5                   10                  15
Ser Gln Glu Ile Tyr Lys Gln Glu Lys Asn Met Ala Ile His Pro Arg
            20                  25                  30
Lys Glu Lys Leu Cys Thr Thr Ser Cys Glu Glu Val Val Arg Asn Ala
        35                  40                  45
Asp Glu Glu Glu Tyr Ser Ile Arg Ser Ser Glu Glu Ser Ala Glu
    50                  55                  60
Val Ala Pro Glu Glu Val Lys Ile Thr Val Asp Asp Lys His Tyr Gln
```

```
            65                  70                  75                  80
Lys Ala Leu Asn Glu Ile Asn Gln Phe Tyr Gln Lys Phe Pro Gln Tyr
                    85                  90                  95

Leu Gln Tyr Leu Tyr Gln Gly Pro Ile Val Leu Asn Pro Trp Asp Gln
                    100                 105                 110

Val Lys Arg Asn Ala Gly Pro Phe Thr Pro Thr Val Asn Arg Glu Gln
                    115                 120                 125

Leu Ser Thr Ser Glu Glu Asn Ser Lys Lys Thr Ile Asp Met Glu Ser
                    130                 135                 140

Thr Glu Val Phe Thr Lys Lys Thr Lys Leu Thr Glu Glu Glu Lys Asn
145                 150                 155                 160

Arg Leu Asn Phe Leu Lys Lys Ile Ser Gln Tyr Tyr Gln Lys Phe Ala
                    165                 170                 175

Trp Pro Gln Tyr Leu Lys Thr Val Asp Gln His Gln Lys Ala Met Lys
                    180                 185                 190

Pro Trp Thr Gln Pro Lys Thr Asn Ala Ile Pro Tyr Val Arg Tyr Leu
                    195                 200                 205
```

<210> SEQ ID NO 44
<211> LENGTH: 209
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Met Lys His Lys Met Glu His Val Ser Ser Ser Glu Glu Pro Ile Asn
1               5                   10                  15

Ile Ser Gln Glu Ile Tyr Lys Gln Glu Lys Asn Met Ala Ile His Pro
                20                  25                  30

Arg Lys Glu Lys Leu Cys Thr Thr Ser Cys Glu Glu Val Val Arg Asn
            35                  40                  45

Ala Asp Glu Glu Glu Tyr Ser Ile Arg Ser Ser Glu Glu Ser Ala
        50                  55                  60

Glu Val Ala Pro Glu Glu Val Lys Ile Thr Val Asp Asp Lys His Tyr
65                  70                  75                  80

Gln Lys Ala Leu Asn Glu Ile Asn Gln Phe Tyr Gln Lys Phe Pro Gln
                85                  90                  95

Tyr Leu Gln Tyr Leu Tyr Gln Gly Pro Ile Val Leu Asn Pro Trp Asp
                100                 105                 110

Gln Val Lys Arg Asn Ala Gly Pro Phe Thr Pro Thr Val Asn Arg Glu
                115                 120                 125

Gln Leu Ser Thr Ser Glu Glu Asn Ser Lys Lys Thr Ile Asp Met Glu
                130                 135                 140

Ser Thr Glu Val Phe Thr Lys Lys Thr Lys Leu Thr Glu Glu Glu Lys
145                 150                 155                 160

Asn Arg Leu Asn Phe Leu Lys Lys Ile Ser Gln Tyr Tyr Gln Lys Phe
                165                 170                 175

Ala Trp Pro Gln Tyr Leu Lys Thr Val Asp Gln His Gln Lys Ala Met
                180                 185                 190

Lys Pro Trp Thr Gln Pro Lys Thr Asn Ala Ile Pro Tyr Val Arg Tyr
                195                 200                 205

Leu
```

<210> SEQ ID NO 45
<211> LENGTH: 223
<212> TYPE: PRT
<213> ORGANISM: Capra sp.

<400> SEQUENCE: 45

Met Lys Phe Phe Ile Phe Thr Cys Leu Leu Ala Val Ala Leu Ala Lys
1               5                   10                  15

His Lys Met Glu His Val Ser Ser Glu Glu Pro Ile Asn Ile Phe
            20                  25                  30

Gln Glu Ile Tyr Lys Gln Glu Lys Asn Met Ala Ile His Pro Arg Lys
        35                  40                  45

Glu Lys Leu Cys Thr Thr Ser Cys Glu Glu Val Val Arg Asn Ala Asn
50                  55                  60

Glu Glu Glu Tyr Ser Ile Arg Ser Ser Glu Glu Ser Ala Glu Val
65                  70                  75                  80

Ala Pro Glu Glu Ile Lys Ile Thr Val Asp Asp Lys His Tyr Gln Lys
                85                  90                  95

Ala Leu Asn Glu Ile Asn Gln Phe Tyr Gln Lys Phe Pro Gln Tyr Leu
            100                 105                 110

Gln Tyr Pro Tyr Gln Gly Pro Ile Val Leu Asn Pro Trp Asp Gln Val
        115                 120                 125

Lys Arg Asn Ala Gly Pro Phe Thr Pro Thr Val Asn Arg Glu Gln Leu
130                 135                 140

Ser Thr Ser Glu Glu Asn Ser Lys Lys Thr Ile Asp Met Glu Ser Thr
145                 150                 155                 160

Glu Val Phe Thr Lys Lys Thr Lys Leu Thr Glu Glu Glu Lys Asn Arg
                165                 170                 175

Leu Asn Phe Leu Lys Lys Ile Ser Gln Tyr Tyr Gln Lys Phe Ala Trp
            180                 185                 190

Pro Gln Tyr Leu Lys Thr Val Asp Gln His Gln Lys Ala Met Lys Pro
        195                 200                 205

Trp Thr Gln Pro Lys Thr Asn Ala Ile Pro Tyr Val Arg Tyr Leu
210                 215                 220

<210> SEQ ID NO 46
<211> LENGTH: 208
<212> TYPE: PRT
<213> ORGANISM: Capra sp.

<400> SEQUENCE: 46

Lys His Lys Met Glu His Val Ser Ser Glu Glu Pro Ile Asn Ile
1               5                   10                  15

Phe Gln Glu Ile Tyr Lys Gln Glu Lys Asn Met Ala Ile His Pro Arg
            20                  25                  30

Lys Glu Lys Leu Cys Thr Thr Ser Cys Glu Glu Val Val Arg Asn Ala
        35                  40                  45

Asn Glu Glu Glu Tyr Ser Ile Arg Ser Ser Glu Glu Ser Ala Glu
50                  55                  60

Val Ala Pro Glu Glu Ile Lys Ile Thr Val Asp Asp Lys His Tyr Gln
65                  70                  75                  80

Lys Ala Leu Asn Glu Ile Asn Gln Phe Tyr Gln Lys Phe Pro Gln Tyr
                85                  90                  95

Leu Gln Tyr Pro Tyr Gln Gly Pro Ile Val Leu Asn Pro Trp Asp Gln
            100                 105                 110

Val Lys Arg Asn Ala Gly Pro Phe Thr Pro Thr Val Asn Arg Glu Gln

```
                    115                 120                 125
Leu Ser Thr Ser Glu Glu Asn Ser Lys Lys Thr Ile Asp Met Glu Ser
    130                 135                 140

Thr Glu Val Phe Thr Lys Lys Thr Lys Leu Thr Glu Glu Lys Asn
145                 150                 155                 160

Arg Leu Asn Phe Leu Lys Lys Ile Ser Gln Tyr Tyr Gln Lys Phe Ala
                165                 170                 175

Trp Pro Gln Tyr Leu Lys Thr Val Asp Gln His Gln Lys Ala Met Lys
            180                 185                 190

Pro Trp Thr Gln Pro Lys Thr Asn Ala Ile Pro Tyr Val Arg Tyr Leu
            195                 200                 205

<210> SEQ ID NO 47
<211> LENGTH: 209
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Lys His Lys Met Glu His Val Ser Ser Glu Glu Pro Ile Asn
1               5                   10                  15

Ile Phe Gln Glu Ile Tyr Lys Gln Glu Lys Asn Met Ala Ile His Pro
                20                  25                  30

Arg Lys Glu Lys Leu Cys Thr Thr Ser Cys Glu Glu Val Val Arg Asn
            35                  40                  45

Ala Asn Glu Glu Glu Tyr Ser Ile Arg Ser Ser Glu Glu Ser Ala
    50                  55                  60

Glu Val Ala Pro Glu Glu Ile Lys Ile Thr Val Asp Asp Lys His Tyr
65                  70                  75                  80

Gln Lys Ala Leu Asn Glu Ile Asn Gln Phe Tyr Gln Lys Phe Pro Gln
                85                  90                  95

Tyr Leu Gln Tyr Pro Tyr Gln Gly Pro Ile Val Leu Asn Pro Trp Asp
            100                 105                 110

Gln Val Lys Arg Asn Ala Gly Pro Phe Thr Pro Thr Val Asn Arg Glu
            115                 120                 125

Gln Leu Ser Thr Ser Glu Glu Asn Ser Lys Lys Thr Ile Asp Met Glu
    130                 135                 140

Ser Thr Glu Val Phe Thr Lys Lys Thr Lys Leu Thr Glu Glu Glu Lys
145                 150                 155                 160

Asn Arg Leu Asn Phe Leu Lys Lys Ile Ser Gln Tyr Tyr Gln Lys Phe
                165                 170                 175

Ala Trp Pro Gln Tyr Leu Lys Thr Val Asp Gln His Gln Lys Ala Met
            180                 185                 190

Lys Pro Trp Thr Gln Pro Lys Thr Asn Ala Ile Pro Tyr Val Arg Tyr
            195                 200                 205

Leu

<210> SEQ ID NO 48
<211> LENGTH: 222
<212> TYPE: PRT
<213> ORGANISM: Bubalus sp.

<400> SEQUENCE: 48

Met Lys Phe Phe Ile Phe Thr Cys Leu Leu Ala Val Ala Leu Ala Lys
1               5                   10                  15
```

His Thr Met Glu His Val Ser Ser Glu Glu Ser Ile Ile Ser Gln
        20                  25                  30

Glu Thr Tyr Lys Gln Glu Lys Asn Met Ala Ile His Pro Ser Lys Glu
            35                  40                  45

Asn Leu Cys Ser Thr Phe Cys Lys Glu Val Ile Arg Asn Ala Asn Glu
        50                  55                  60

Glu Glu Tyr Ser Ile Gly Ser Ser Glu Glu Ser Ala Glu Val Ala
65                  70                  75                  80

Thr Glu Glu Val Lys Ile Thr Val Asp Asp Lys His Tyr Gln Lys Ala
                85                  90                  95

Leu Asn Glu Ile Asn Gln Phe Tyr Gln Lys Phe Pro Gln Tyr Leu Gln
            100                 105                 110

Tyr Leu Tyr Gln Gly Pro Ile Val Leu Asn Pro Trp Asp Gln Val Lys
            115                 120                 125

Arg Asn Ala Val Pro Ile Thr Pro Thr Leu Asn Arg Glu Gln Leu Ser
130                 135                 140

Thr Ser Glu Glu Asn Ser Lys Lys Thr Val Asp Met Glu Ser Thr Glu
145                 150                 155                 160

Val Phe Thr Lys Lys Thr Lys Leu Thr Glu Glu Asp Lys Asn Arg Leu
                165                 170                 175

Asn Phe Leu Lys Lys Ile Ser Gln His Tyr Gln Lys Phe Ala Trp Pro
            180                 185                 190

Gln Tyr Leu Lys Thr Val Tyr Gln Tyr Gln Lys Ala Met Lys Pro Trp
            195                 200                 205

Thr Gln Pro Lys Thr Asn Val Ile Pro Tyr Val Arg Tyr Leu
            210                 215                 220

<210> SEQ ID NO 49
<211> LENGTH: 207
<212> TYPE: PRT
<213> ORGANISM: Bubalus sp.

<400> SEQUENCE: 49

Lys His Thr Met Glu His Val Ser Ser Glu Glu Ser Ile Ile Ser
1               5                   10                  15

Gln Glu Thr Tyr Lys Gln Glu Lys Asn Met Ala Ile His Pro Ser Lys
            20                  25                  30

Glu Asn Leu Cys Ser Thr Phe Cys Lys Glu Val Ile Arg Asn Ala Asn
        35                  40                  45

Glu Glu Glu Tyr Ser Ile Gly Ser Ser Glu Glu Ser Ala Glu Val
        50                  55                  60

Ala Thr Glu Glu Val Lys Ile Thr Val Asp Asp Lys His Tyr Gln Lys
65                  70                  75                  80

Ala Leu Asn Glu Ile Asn Gln Phe Tyr Gln Lys Phe Pro Gln Tyr Leu
                85                  90                  95

Gln Tyr Leu Tyr Gln Gly Pro Ile Val Leu Asn Pro Trp Asp Gln Val
            100                 105                 110

Lys Arg Asn Ala Val Pro Ile Thr Pro Thr Leu Asn Arg Glu Gln Leu
            115                 120                 125

Ser Thr Ser Glu Glu Asn Ser Lys Lys Thr Val Asp Met Glu Ser Thr
        130                 135                 140

Glu Val Phe Thr Lys Lys Thr Lys Leu Thr Glu Glu Asp Lys Asn Arg
145                 150                 155                 160

Leu Asn Phe Leu Lys Lys Ile Ser Gln His Tyr Gln Lys Phe Ala Trp

-continued

```
                165                 170                 175
Pro Gln Tyr Leu Lys Thr Val Tyr Gln Tyr Gln Lys Ala Met Lys Pro
            180                 185                 190

Trp Thr Gln Pro Lys Thr Asn Val Ile Pro Tyr Val Arg Tyr Leu
        195                 200                 205

<210> SEQ ID NO 50
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Lys His Thr Met Glu His Val Ser Ser Ser Glu Glu Ser Ile Ile
1               5                   10                  15

Ser Gln Glu Thr Tyr Lys Gln Glu Lys Asn Met Ala Ile His Pro Ser
            20                  25                  30

Lys Glu Asn Leu Cys Ser Thr Phe Cys Lys Glu Val Ile Arg Asn Ala
        35                  40                  45

Asn Glu Glu Glu Tyr Ser Ile Gly Ser Ser Glu Glu Ser Ala Glu
    50                  55                  60

Val Ala Thr Glu Glu Val Lys Ile Thr Val Asp Asp Lys His Tyr Gln
65                  70                  75                  80

Lys Ala Leu Asn Glu Ile Asn Gln Phe Tyr Gln Lys Phe Pro Gln Tyr
                85                  90                  95

Leu Gln Tyr Leu Tyr Gln Gly Pro Ile Val Leu Asn Pro Trp Asp Gln
            100                 105                 110

Val Lys Arg Asn Ala Val Pro Ile Thr Pro Thr Leu Asn Arg Glu Gln
        115                 120                 125

Leu Ser Thr Ser Glu Glu Asn Ser Lys Lys Thr Val Asp Met Glu Ser
    130                 135                 140

Thr Glu Val Phe Thr Lys Lys Thr Lys Leu Thr Glu Glu Asp Lys Asn
145                 150                 155                 160

Arg Leu Asn Phe Leu Lys Lys Ile Ser Gln His Tyr Gln Lys Phe Ala
                165                 170                 175

Trp Pro Gln Tyr Leu Lys Thr Val Tyr Gln Tyr Gln Lys Ala Met Lys
            180                 185                 190

Pro Trp Thr Gln Pro Lys Thr Asn Val Ile Pro Tyr Val Arg Tyr Leu
        195                 200                 205

<210> SEQ ID NO 51
<211> LENGTH: 214
<212> TYPE: PRT
<213> ORGANISM: Equus sp.

<400> SEQUENCE: 51

Met Lys Phe Phe Ile Phe Thr Cys Leu Leu Ala Val Ala Leu Ala Lys
1               5                   10                  15

His Asn Met Glu His Arg Ser Ser Ser Glu Asp Ser Val Asn Ile Ser
            20                  25                  30

Gln Glu Lys Phe Lys Gln Glu Lys Tyr Val Val Ile Pro Thr Ser Lys
        35                  40                  45

Glu Ser Ile Cys Ser Thr Ser Cys Glu Glu Ala Thr Arg Asn Ile Asn
    50                  55                  60

Glu Met Glu Ser Ala Lys Phe Pro Thr Glu Arg Glu Glu Lys Glu Val
```

```
            65                  70                  75                  80
Glu Glu Lys His His Leu Lys Gln Leu Asn Lys Ile Asn Gln Phe Tyr
                    85                  90                  95
Glu Lys Leu Asn Phe Leu Gln Tyr Leu Gln Ala Leu Arg Gln Pro Arg
                100                 105                 110
Ile Val Leu Thr Pro Trp Asp Gln Thr Lys Thr Gly Asp Ser Pro Phe
                115                 120                 125
Ile Pro Ile Val Asn Thr Glu Gln Leu Phe Thr Ser Glu Glu Ile Pro
        130                 135                 140
Lys Lys Thr Val Asp Met Glu Ser Thr Glu Val Val Thr Glu Lys Thr
145                 150                 155                 160
Glu Leu Thr Glu Glu Glu Lys Asn Tyr Leu Lys Leu Tyr Tyr Glu
                165                 170                 175
Lys Phe Thr Leu Pro Gln Tyr Phe Lys Ile Val Arg Gln His Gln Thr
                180                 185                 190
Thr Met Asp Pro Arg Ser His Arg Lys Thr Asn Ser Tyr Gln Ile Ile
                195                 200                 205
Pro Val Leu Arg Tyr Phe
        210

<210> SEQ ID NO 52
<211> LENGTH: 199
<212> TYPE: PRT
<213> ORGANISM: Equus sp.

<400> SEQUENCE: 52

Lys His Asn Met Glu His Arg Ser Ser Ser Glu Asp Ser Val Asn Ile
1               5                   10                  15
Ser Gln Glu Lys Phe Lys Gln Glu Lys Tyr Val Val Ile Pro Thr Ser
                20                  25                  30
Lys Glu Ser Ile Cys Ser Thr Ser Cys Glu Glu Ala Thr Arg Asn Ile
                35                  40                  45
Asn Glu Met Glu Ser Ala Lys Phe Pro Thr Glu Arg Glu Glu Lys Glu
        50                  55                  60
Val Glu Glu Lys His His Leu Lys Gln Leu Asn Lys Ile Asn Gln Phe
65                  70                  75                  80
Tyr Glu Lys Leu Asn Phe Leu Gln Tyr Leu Gln Ala Leu Arg Gln Pro
                85                  90                  95
Arg Ile Val Leu Thr Pro Trp Asp Gln Thr Lys Thr Gly Asp Ser Pro
                100                 105                 110
Phe Ile Pro Ile Val Asn Thr Glu Gln Leu Phe Thr Ser Glu Glu Ile
                115                 120                 125
Pro Lys Lys Thr Val Asp Met Glu Ser Thr Glu Val Val Thr Glu Lys
        130                 135                 140
Thr Glu Leu Thr Glu Glu Glu Lys Asn Tyr Leu Lys Leu Leu Tyr Tyr
145                 150                 155                 160
Glu Lys Phe Thr Leu Pro Gln Tyr Phe Lys Ile Val Arg Gln His Gln
                165                 170                 175
Thr Thr Met Asp Pro Arg Ser His Arg Lys Thr Asn Ser Tyr Gln Ile
                180                 185                 190
Ile Pro Val Leu Arg Tyr Phe
                195

<210> SEQ ID NO 53
<211> LENGTH: 200
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

Met Lys His Asn Met Glu His Arg Ser Ser Ser Glu Asp Ser Val Asn
1               5                   10                  15
Ile Ser Gln Glu Lys Phe Lys Gln Glu Lys Tyr Val Val Ile Pro Thr
            20                  25                  30
Ser Lys Glu Ser Ile Cys Ser Thr Ser Cys Glu Glu Ala Thr Arg Asn
        35                  40                  45
Ile Asn Glu Met Glu Ser Ala Lys Phe Pro Thr Glu Arg Glu Glu Lys
    50                  55                  60
Glu Val Glu Glu Lys His His Leu Lys Gln Leu Asn Lys Ile Asn Gln
65                  70                  75                  80
Phe Tyr Glu Lys Leu Asn Phe Leu Gln Tyr Leu Gln Ala Leu Arg Gln
                85                  90                  95
Pro Arg Ile Val Leu Thr Pro Trp Asp Gln Thr Lys Thr Gly Asp Ser
            100                 105                 110
Pro Phe Ile Pro Ile Val Asn Thr Glu Gln Leu Phe Thr Ser Glu Glu
        115                 120                 125
Ile Pro Lys Lys Thr Val Asp Met Glu Ser Thr Glu Val Val Thr Glu
    130                 135                 140
Lys Thr Glu Leu Thr Glu Glu Lys Asn Tyr Leu Lys Leu Leu Tyr
145                 150                 155                 160
Tyr Glu Lys Phe Thr Leu Pro Gln Tyr Phe Lys Ile Val Arg Gln His
                165                 170                 175
Gln Thr Thr Met Asp Pro Arg Ser His Arg Lys Thr Asn Ser Tyr Gln
            180                 185                 190
Ile Ile Pro Val Leu Arg Tyr Phe
        195                 200

<210> SEQ ID NO 54
<211> LENGTH: 193
<212> TYPE: PRT
<213> ORGANISM: Camelus sp.

<400> SEQUENCE: 54

Met Lys Phe Phe Ile Phe Thr Cys Leu Leu Ala Val Val Leu Ala Lys
1               5                   10                  15
His Glu Met Asp Gln Gly Ser Ser Glu Glu Ser Ile Asn Val Ser
            20                  25                  30
Gln Gln Lys Phe Lys Gln Val Lys Lys Val Ala Ile His Pro Ser Lys
        35                  40                  45
Glu Asp Ile Cys Ser Thr Phe Cys Glu Glu Ala Val Arg Asn Ile Lys
    50                  55                  60
Glu Val Glu Ser Ala Glu Val Pro Thr Glu Asn Lys Ile Ser Gln Phe
65                  70                  75                  80
Tyr Gln Lys Trp Lys Phe Leu Gln Tyr Leu Gln Ala Leu His Gln Gly
                85                  90                  95
Gln Ile Val Met Asn Pro Trp Asp Gln Gly Lys Thr Arg Ala Tyr Pro
            100                 105                 110
Phe Ile Pro Thr Val Asn Thr Glu Gln Leu Ser Ile Ser Glu Glu Ser
        115                 120                 125

```
Thr Glu Val Pro Thr Glu Glu Ser Thr Glu Val Phe Thr Lys Lys Thr
            130                 135                 140

Glu Leu Thr Glu Glu Lys Asp His Gln Lys Phe Leu Asn Lys Ile
145                 150                 155                 160

Tyr Gln Tyr Tyr Gln Thr Phe Leu Trp Pro Glu Tyr Leu Lys Thr Val
                165                 170                 175

Tyr Gln Tyr Gln Lys Thr Met Thr Pro Trp Asn His Ile Lys Arg Tyr
            180                 185                 190

Phe

<210> SEQ ID NO 55
<211> LENGTH: 178
<212> TYPE: PRT
<213> ORGANISM: Camelus sp.

<400> SEQUENCE: 55

Lys His Glu Met Asp Gln Gly Ser Ser Glu Glu Ser Ile Asn Val
1               5                   10                  15

Ser Gln Gln Lys Phe Lys Gln Val Lys Val Ala Ile His Pro Ser
            20                  25                  30

Lys Glu Asp Ile Cys Ser Thr Phe Cys Glu Glu Ala Val Arg Asn Ile
            35                  40                  45

Lys Glu Val Glu Ser Ala Glu Val Pro Thr Glu Asn Lys Ile Ser Gln
50                  55                  60

Phe Tyr Gln Lys Trp Lys Phe Leu Gln Tyr Leu Gln Ala Leu His Gln
65                  70                  75                  80

Gly Gln Ile Val Met Asn Pro Trp Asp Gln Gly Lys Thr Arg Ala Tyr
                85                  90                  95

Pro Phe Ile Pro Thr Val Asn Thr Glu Gln Leu Ser Ile Ser Glu Glu
            100                 105                 110

Ser Thr Glu Val Pro Thr Glu Glu Ser Thr Glu Val Phe Thr Lys Lys
            115                 120                 125

Thr Glu Leu Thr Glu Glu Lys Asp His Gln Lys Phe Leu Asn Lys
            130                 135                 140

Ile Tyr Gln Tyr Tyr Gln Thr Phe Leu Trp Pro Glu Tyr Leu Lys Thr
145                 150                 155                 160

Val Tyr Gln Tyr Gln Lys Thr Met Thr Pro Trp Asn His Ile Lys Arg
                165                 170                 175

Tyr Phe

<210> SEQ ID NO 56
<211> LENGTH: 179
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Lys His Glu Met Asp Gln Gly Ser Ser Ser Glu Glu Ser Ile Asn
1               5                   10                  15

Val Ser Gln Gln Lys Phe Lys Gln Val Lys Val Ala Ile His Pro
            20                  25                  30

Ser Lys Glu Asp Ile Cys Ser Thr Phe Cys Glu Glu Ala Val Arg Asn
            35                  40                  45

Ile Lys Glu Val Glu Ser Ala Glu Val Pro Thr Glu Asn Lys Ile Ser
50                  55                  60
```

```
Gln Phe Tyr Gln Lys Trp Lys Phe Leu Gln Tyr Leu Gln Ala Leu His
 65                  70                  75                  80

Gln Gly Gln Ile Val Met Asn Pro Trp Asp Gln Gly Lys Thr Arg Ala
                 85                  90                  95

Tyr Pro Phe Ile Pro Thr Val Asn Thr Glu Gln Leu Ser Ile Ser Glu
             100                 105                 110

Glu Ser Thr Glu Val Pro Thr Glu Glu Ser Thr Glu Val Phe Thr Lys
         115                 120                 125

Lys Thr Glu Leu Thr Glu Glu Glu Lys Asp His Gln Lys Phe Leu Asn
         130                 135             140

Lys Ile Tyr Gln Tyr Tyr Gln Thr Phe Leu Trp Pro Glu Tyr Leu Lys
145                 150                 155                 160

Thr Val Tyr Gln Tyr Gln Lys Thr Met Thr Pro Trp Asn His Ile Lys
             165                 170                 175

Arg Tyr Phe
```

DAIRY-LIKE COMPOSITIONS AND RELATED METHODS

CROSS-REFERENCE

This application claims the benefit of U.S. Provisional Application No. 63/234,193, filed on Aug. 17, 2021, which application is incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 17, 2022, is named 56127-705_201_SL.txt and is 98,260 bytes in size.

BACKGROUND

The clean food space is comprised of both plant-based and cell-based foods. Cell-based food is a large umbrella term that includes culturing muscle and fat cells to replace slaughtered meat and culturing bioengineered organisms to express recombinant animal proteins to replace other animal products such as dairy and eggs. The need to find an alternate source of animal protein comes from the inefficiencies and unsustainability of current animal food production.

Cheese is the third most unsustainable animal product globally (when measuring greenhouse gas emissions per kg of product), and the consumption of dairy cheese hasn't been slowed down by plant-based alternatives introduced into the market in the last 10 years. On the contrary, mozzarella cheese consumption is growing year on year in the US and in developing markets. Current cheese alternatives do not match the functionality, nutrition and taste of dairy cheese due to their lack of casein proteins.

SUMMARY

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

In some aspects, described herein is a cheese analogue comprising a recombinant single variant of an alpha casein protein. In some embodiments, the recombinant single variant provides at least one dairy-like property selected from the group consisting of adhesiveness, stretch, texture, mouthfeel, melt, hardness, creaminess, and flexibility. In some embodiments, the recombinant single variant is not an animal-derived casein and has not been physically dissociated from a casein micelle. In some embodiments, the cheese analogue lacks any caseins other than the recombinant single variant.

In some embodiments, the recombinant single variant of the alpha casein lacks one or more post-translational modifications of a native alpha casein protein. In some embodiments, the recombinant single variant lacks post-translational modifications. In some embodiments, the recombinant single variant of the alpha casein protein lacks phosphorylation. In some embodiments, the recombinant single variant of the alpha casein protein is a recombinant alpha-s1 casein protein.

In some embodiments, at least 5% of the cheese analogue is the recombinant alpha-s1 casein protein w/w. In some embodiments, the recombinant alpha-s1 casein protein comprises an amino acid sequence of a ruminant alpha-S1 casein protein.

In some embodiments, the recombinant single variant comprises a full-length mature form of the recombinant single variant and one or more truncated forms of the recombinant single variant.

In some embodiments, from 0.1% to 20% wt/wt of the total recombinant alpha casein protein of the cheese analogue is the one or more truncated forms of the recombinant alpha-s1 casein protein.

In some embodiments, at least one of the truncated forms of the recombinant alpha-s1 casein protein lacks one or more N-terminal amino acids of a mature native alpha casein protein.

In some embodiments, the amino acid sequence of at least one of the truncated forms of the recombinant alpha-s1 casein protein is SEQ ID NOs.: 6 or 12 or an amino acid sequence with at least 98% identity to SEQ ID NOs.: 6 or 12.

In some embodiments, at least one of the N-terminal truncated forms of the recombinant alpha-s1 casein protein is an alpha-s1 casein lacking from 1 to 23 N-terminal amino acids of the native alpha-s1 casein protein or an alpha-s1 casein lacking from 1 to 59 N-terminal amino acids of the native alpha-s1 casein protein.

In some embodiments, the recombinant single variant of an alpha casein protein comprises an amino acid sequence of SEQ ID NOs: 2 or 3 or an amino acid sequence with at least 90% sequence identity to SEQ ID NOs.: 2 or 3.

In some embodiments, the full-length mature form of the recombinant alpha-s1 casein protein comprises an amino acid sequence of SEQ ID NOs.: 2 or 3 or an amino acid sequence with at least 90% identity to SEQ ID NOs.: 2 or 3.

In some embodiments, the cheese analogue lacks any animal-derived dairy proteins. In some embodiments, the recombinant single variant of an alpha casein protein is not comprised in a micellar form within the cheese analogue. In some embodiments, the recombinant single variant of an alpha casein protein comprises one or more non-native amino acids at the N-terminus. In some embodiments, the recombinant single variant of an alpha casein protein comprises a non-native methionine at the N-terminal position.

In some embodiments, the cheese analogue is a vegan cheese analogue. In some embodiments, the cheese analogue further comprises one or more of (a) a plant-derived oil; (b) a plant-derived starch: (c) a sugar; and (d) a salt. In some embodiments, the cheese analogue further comprises a flavoring selected from cheddar flavor, parmesan flavor or mozzarella flavoring. In some embodiments, the flavoring is mozzarella flavoring and the cheese analogue is a mozzarella analogue.

In some embodiments, at least one dairy-like property is improved as compared to a caseinate-derived cheese analogue, a rennet casein-derived cheese analogue or a plant-derived cheese analogue. In some embodiments, the adhesiveness of the cheese analogue is reduced as compared to a plant-derived cheese analogue.

In some embodiments, the cheese analogue lacks micelles or micellar forms.

In some aspects, described herein is a mozzarella cheese analogue. In some embodiments, the mozzarella cheese analogue may comprise an isolated recombinant single variant of a bovine alpha casein protein. The mozzarella cheese may additionally comprise a flavoring; a plant-derived oil; and moisture level between 45%-52%. In some embodiments, the isolated recombinant single variant of a bovine alpha casein protein has reduced phosphorylation as compared to an animal-derived bovine alpha casein protein. In some embodiments, the mozzarella cheese analogue lacks any additional caseins or animal-derived proteins. In some embodiments, the mozzarella analogue has a stretch property comparable or improved relative to a caseinate-derived mozzarella analogue.

In some embodiments, the mozzarella cheese analogue comprises from 5%-30% of the bovine alpha casein protein w/w. In some embodiments, the mozzarella cheese analogue comprises a full-length mature form of the recombinant alpha casein protein and one or more truncated forms of the recombinant alpha casein protein, wherein the amino acid sequence of at least one of the truncated forms of the recombinant alpha casein protein is SEQ ID NOs.: 6 or 12 or an amino acid sequence with at least 98% identity to SEQ ID NOs.: 6 or 12.

In some embodiments, the cheese analogue further comprises one or more of (a) a plant-derived starch; (b) a sugar; and (c) a salt. In some embodiments, a stretch (extensibility) of the mozzarella cheese analogue is increased and an adhesiveness of the mozzarella cheese analogue is decreased as compared to a plant-derived mozzarella cheese analogue.

INCORPORATION BY REFERENCE

All publications, patents, and patent applications mentioned in this specification are herein incorporated by reference to the same extent as if each individual publication, patent, or patent application was specifically and individually indicated to be incorporated by reference

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings.

DETAILED DESCRIPTION OF THE INVENTION

Figure 1:
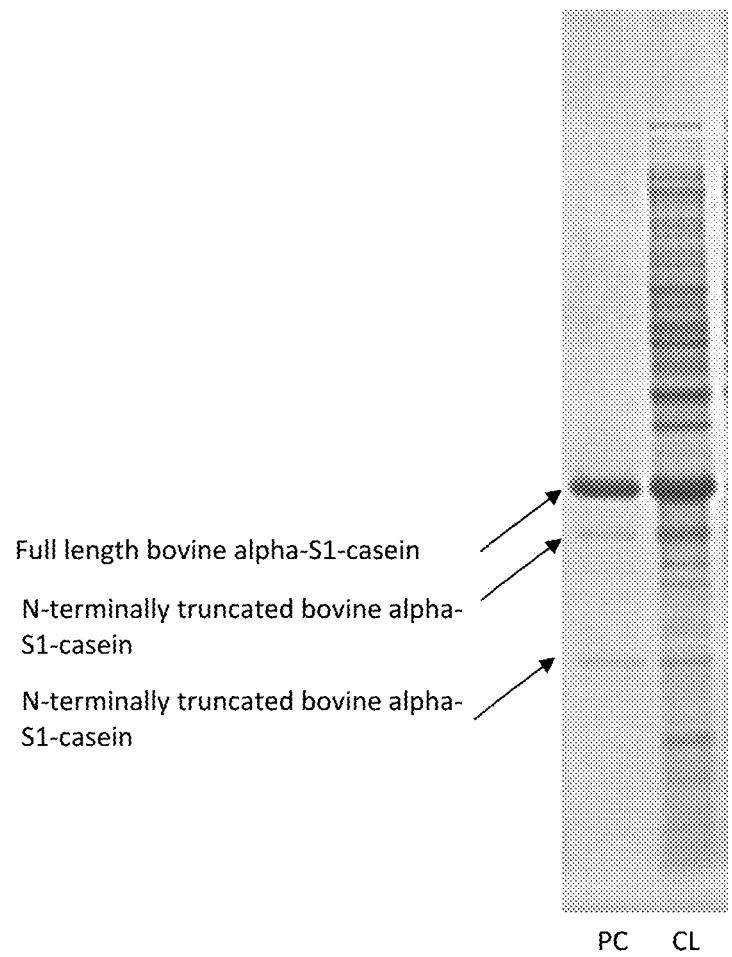
FIG. 1 illustrates recombinantly produced full-length alpha S1 casein protein and two occurring truncated forms of alpha S1 casein.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Although the dairy industry is worth $330 billion, research needs to be performed for a clean dairy solution using recombinant dairy proteins. As dairy cheese is an inefficient dairy product, in terms of resources needed per gram as well as being the hardest dairy product to accurately reproduce from just plant-based ingredients, presented herein are methods and compositions of recombinant cheese.

A component that gives dairy cheese its unique characteristics is the casein proteins. When milk or milk-derived ingredients are used in dairy products, the caseins are found in micelles. Micelles are protein colloids and typically in cow milk, the micelles are comprised of four casein proteins (alpha S1 casein, alpha S2 casein, beta casein, and kappa casein) that interact with insoluble calcium phosphate at the colloid centre. It is the micelles in milk that attract each other once chymosin is added to milk. This forms the curd, which is then used to make 99% of all cheeses. In case of yogurt, acidification of the micelle comprising liquid colloid may be performed using a starter culture of bacteria known for yogurt production. The current disclosure is based on the discovery that a recombinant non-naturally occurring single variant of alpha casein can be used to generate dairy or dairy-like products without the presence of other caseins and without the formation of a micelle. People skilled in the art have attempted to isolate different casein proteins from milk or milk micelles for producing dairy like products but the inventors of this application have discovered for the first time that a single variant alpha casein, in recombinant form, particularly in some embodiments lacking or having different post translational modifications (PTMs) from native alpha casein, can provide dairy-like features without being present in a micellar form and without the association with or presence of other caseins or other dairy proteins.

One skilled in the art would know that micelles are complex structures with multiple proteins and would therefore not expect to be able to form dairy-like products such as cheese, cheese analogues, yogurt, and other dairy products using a single casein protein. The current disclosure is based on the surprising discovery made by the inventors that a single recombinantly produced casein protein, a single variant of alpha casein, is able to form consumables without forming or being incorporated into micelles. The current disclosure also describes recombinantly made dairy products such as cheese analogues and other dairy analogue products, as well as powders using the compositions formed by the methods described herein.

The current disclosure also describes consumable compositions that incorporate truncated forms of a recombinantly made single variant of an alpha casein protein. Compositions described herein may comprise different truncated forms of casein proteins.

The consumable compositions described herein are formed from a recombinant single alpha casein variant. Recombinant casein protein may be expressed in a microbial organism, for example, bacteria such as gram-positive bacteria *Lactococcus lactis* and *Bacillus subtilis*, as well as a gram-negative model organism *E. coli*, as well as other host organisms such as yeasts, fungi, and plants. These recombinant alpha casein proteins may be combined with other components (e.g., minerals, fats, sugars, and vitamins) to make dairy-like products, for example, cheese that behaves, smells, tastes, looks and feels like animal-derived dairy cheese. Such dairy-like products may have no: i) lactose, ii) cholesterol, iii) animal-derived saturated fats, iv) milk-derived whey proteins; and/or v) milk-derived casein proteins.

In some embodiments, the methods include producing a single variant of an alpha casein protein in a bacterial host cell, such that such proteins are secreted from the cell into the surrounding media. In some embodiments, the methods include producing recombinant protein in a bacterial host cell, such that such proteins are intracellular. Recombinant protein can then be isolated, purified or partially purified and used in methods for making compositions which can be used as a dairy ingredient, or emulsified with plant-based fats and other nutrients to form milk, cheese, yogurt or other dairy-like analogue products.

In some embodiments, the methods include producing compositions using a single alpha casein from a variety of different species. The alpha casein may be from human, *Bovinae* (cattle, bison, buffalo), *Caprinae* (sheep and goat), *Equine* (horses, zebra) and *Camelus* (camels). The single alpha casein variant may be modified as compared to a native alpha casein, for instance, truncated forms of native caseins. Compositions described herein are produced without beta or kappa casein.

In some embodiments, recombinant alpha caseins can be isolated, purified or partially purified from genetically modified microorganism or their cultivation broth.

The term "about" as used herein can mean within 1 or 2 standard deviations. Alternatively, "about" can mean a range of up to 10%, up to 5%, or up to 1% of a given value. For example, about can mean up to ±10%, +9%, ±8%, ±7%, ±6%, ±5%, ±4%, ±3%, ±2%, or ±1% of a given value.

The term "dairy protein" as used herein means a protein that has an amino acid sequence derived from a protein found in milk (including variants thereof).

The term "animal-derived dairy protein" as used herein means a protein derived from milk, such as a protein obtained and/or isolated from milk of a milk-producing organism, including but not limited to cow, sheep, goat, human, bison, buffalo, camel and horse. "Animal-derived casein protein" means casein protein obtained and/or isolated from milk of a milk-producing organism.

The term "recombinant dairy protein" as used herein means a protein that is expressed in a heterologous or recombinant organism that has an amino acid sequence derived from a protein found in milk (including variants thereof). "Recombinant casein protein" means a casein produced by a recombinant organism or in a heterologous host cell.

The term "single variant of alpha casein" (also referred to as "single variant alpha casein protein") as used herein may describe a composition comprising or created from one variant of an alpha casein protein amino acid sequence. For instance, a composition comprising a single variant of alpha casein comprises only one of alpha S1 or alpha S2 casein. A composition comprising a single variant of alpha casein may be created from only one alpha casein protein amino acid sequence but may comprise truncated forms of the protein sequence in place of or in addition to the full-length version of the protein. For instance, a composition comprising a single variant of alpha casein protein may comprise a mixture of full length alpha S1 casein protein and truncated forms thereof. A composition comprising a single variant of alpha casein may comprise only the full-length alpha S1 casein protein or only a truncated form of alpha S1 casein protein, or only a mixture of truncated forms of the alpha S1 protein.

A percentage of "sequence identity" as used herein in the context of polynucleotide or polypeptide (amino acid) sequences refers to the percentage of residues in two sequences that are the same when the sequences are aligned for maximum correspondence. There are a number of different algorithms known in the art that can be used to measure polynucleotide or polypeptide sequence identity. For instance, sequences can be compared using FASTA (e.g., using its default parameters as provided in the Wisconsin Package Version 10.0, Genetics Computer Group (GCG), Madison, Wis.), Gap (e.g., using its default parameters as provided in the Wisconsin Package Version 10.0, GCG, Madison, Wis.), Bestfit, ClustalW (e.g., using default parameters of Version 1.83), or BLAST (e.g., using reciprocal BLAST, PSI-BLAST, BLASTP, BLASTN) (see, for example, Pearson. 1990. Methods Enzymol. 183:63; Altschul et al. 1990. J. Mol. Biol. 215:403).

1. Compositions Comprising Caseins

I. Casein Proteins

Traditionally, cheese begins with animal-derived milk. The process of animal-derived cheese production includes precipitating micellar forms from milk wherein the micellar forms are in most cases complex protein mixtures (comprising multiple types of casein proteins such as alpha, beta and kappa proteins). Milk is acidified, the micelles shrink and dissociate slightly, then milk is renneted and made into curd, and the curd made into cheese. Cheese analogues may be created from animal milk by first precipitating casein micelles from milk using one of the following methods: 1) a sodium salt to make sodium caseinate, 2) an acid to make acid casein, 3) enzymatic coagulation with rennet to make rennet casein. Casein precipitated in this way from milk is then further processed with fats to create the cheese analogue.

Provided herein are consumable compositions with a single variant of alpha casein, produced recombinantly, that is not in micellar form and not derived from milk or derived from milk casein. In some aspects, the consumable compositions of the disclosure are not only made of a single variant alpha casein but are able to provide dairy-like properties to food and beverage products without being in a micellar structure or being derived from a starting material having a micellar structure.

In some embodiments, compositions herein (and products made therefrom) do not include any dairy proteins other than a single variant of alpha casein protein. In some cases, compositions herein (and products made therefrom) do not include any whey proteins or any milk-derived whey proteins. In some embodiments, compositions herein (and products made therefrom) do not include any animal-derived dairy proteins. The compositions herein do not comprise any casein proteins isolated from any animal-derived products or micelles.

The compositions described herein comprise single variants of alpha casein that are made through recombinant production. In some cases, the single variant casein in a consumable composition may be a modified alpha casein protein relative to a native alpha casein protein. The modifications in the single variant of an alpha casein protein may comprise one or more amino acid insertions, deletions, or substitutions relative to a wild-type or native alpha casein protein. A single variant of an alpha casein protein may be a recombinant protein that is a truncated alpha casein protein relative to a wild-type or native alpha casein protein. The truncation may resemble a truncation found in nature (e.g., having a common number of amino acids). The truncation may be a non-naturally occurring truncation of the alpha casein protein. A single variant of an alpha casein protein may have a N-terminal truncation relative to a wild-type or native alpha casein protein. A single variant of an alpha casein protein may have a C-terminal truncation relative to a wild-type or native alpha casein protein. A single variant of an alpha casein protein may have an N-terminal truncation and a C-terminal truncation relative to a wild-type or native alpha casein protein.

In some embodiments, the single variant of an alpha casein in a consumable composition is an alpha S1 casein. In such compositions, the alpha S1 casein may comprise a modified alpha S1 casein, such as modified in a post-translational modification type (phosphorylation, glycosylation, position of such modifications or quantity of such modifications). In some cases, the alpha S1 casein may be a full-length alpha S1 casein. In some cases, the compositions comprising an alpha S1 casein protein lacks any animal-derived proteins.

In some embodiments, the single variant of an alpha casein in a consumable composition is an alpha S2 casein. In such compositions, the alpha S2 casein may comprise a modified alpha S2 casein such as modified in post-translational modification type (phosphorylation, glycosylation, position of such modifications or quantity of such modifications). In some cases, the alpha S2 casein may be a full-length alpha S2 casein. In some cases, the compositions comprising an alpha S2 casein protein lacks any animal-derived proteins.

The compositions herein comprising a single variant of an alpha casein protein, are recombinant proteins and do not comprise alpha casein proteins isolated from casein micelles or alpha casein proteins isolated from any naturally occurring micellar forms or products comprising micelles or micellar forms.

A single variant of an alpha casein protein may be from a ruminant species. A single variant of an alpha casein protein may be a bovine alpha casein protein. A single variant of an alpha casein may be a caprine alpha casein protein. A single variant of an alpha casein protein may be an ovine alpha casein protein. A single variant of an alpha casein protein may be an equine alpha casein protein. A single variant of an alpha casein protein may be a camel or camelid alpha casein protein. A single variant of an alpha casein protein may be a human alpha casein protein A single variant of an alpha casein protein may be a mature form of an alpha casein (lacking a signal sequence, such as exemplified in SEQ ID NOs: 2, 3, 14, 15, 26, 27, 29, 30, 32, 33, 35, 36, 38, 40, 41, 43, 44, 46, 47, 49, 50, 52, 53, 55 or 56) or a truncated form thereof (exemplified as SEQ ID NOs: 4-12, 16-24). A single variant of an alpha casein protein may be a bovine alpha casein protein, for instance, casein protein with at least 70%, 75%, 80%, 85%, 90%, 95%, 97%, 98% or 99% sequence identity to SEQ ID NO: 1-3, 28-30, 39-41 or 48-50 or a truncated form thereof. A single variant of an alpha casein may be an ovine alpha casein protein, for instance, casein protein with at least 70%, 75%, 80%, 85%, 90%, 95%, 97%, 98% or 99% sequence identity to SEQ ID NO: 13-15 or 42-44 or a truncated form thereof. A single variant of an alpha casein protein may be a caprine alpha casein protein, for instance, casein protein with at least 70%, 75%, 80%, 85%, 90%, 95%, 97%, 98% or 99% sequence identity to SEQ ID NO: 25-27 or 45-47 or a truncated form thereof. A single variant of an alpha casein protein may be an equine alpha casein protein, for instance, casein protein with at least 70%, 75%, 80%, 85%, 90%, 95%, 97%, 98% or 99% sequence identity to SEQ ID NO: 31-33 or 51-53 or a truncated form thereof. A single variant of an alpha casein protein may be a camel alpha casein protein, for instance, casein protein with at least 70%, 75%, 80%, 85%, 90%, 95%, 97%, 98% or 99% sequence identity to SEQ ID NO: 34-36 or 54-56 or a truncated form thereof. A single variant of an alpha casein protein may be a human alpha casein protein, for instance, casein protein with at least 70%, 75%, 80%, 85%, 90%, 95%, 97%, 98% or 99% sequence identity to SEQ ID NO: 37-38 or a truncated form thereof.

The single variant of an alpha casein protein in a consumable composition may be an alpha S1 casein protein. The alpha S1 casein protein may be a full-length alpha S1 casein protein. In some cases, the alpha S1 protein is a truncated alpha S1 protein relative to a wild-type or native alpha S1 casein protein. In some cases, the alpha S1 casein protein has a N-terminal truncation relative to a wild-type or native alpha S1 casein protein. In some cases, the alpha S1 casein protein has a C-terminal truncation relative to a wild-type or native alpha S1 casein protein. In some cases, the alpha S1 casein may have a N-terminal truncation and a C-terminal truncation relative to a wild-type or native alpha S1 casein. In some cases, the alpha S1 protein lacks between 1 and 59 N-terminal amino acids. In some cases, the alpha S1 protein lacks between 1 to 5, 1 to 10, 1 to 20, 1 to 30, 1 to 50, 1 to 59 N-terminal amino acids. In some cases, a bovine alpha S1 protein with SEQ ID NO: 2 lacks between 1 to 59 N-terminal amino acids. In some cases, a bovine alpha S1 protein with SEQ ID NO: 2 lacks 22, 23, 24 or 25 N-terminal amino acids (see examples such as SEQ ID NOs: 4-12). In some cases, an ovine alpha S1 protein with SEQ ID NO: 14 lacks between 1 to 59 N-terminal amino acids (see examples such as SEQ ID NOs: 16-24). In some cases, an ovine alpha S1 protein with SEQ ID NO: 14 lacks 22, 23, 24 or 25 N-terminal amino acids.

In some cases, the alpha S1 casein is a mixture of a full-length alpha S1 casein and one or more truncated forms of the alpha S1 casein protein, such as any one or more of the truncated forms described herein.

In some cases, a composition herein made from a single variant of an alpha casein comprises a mixture of a full-length form and one or more truncated forms of the alpha casein protein and in such compositions the total alpha casein may be comprised of up to 20% wt/wt of the one or more truncated forms of the alpha S1 casein. The truncated forms may be any truncated forms of the full-length single variant alpha S1 casein protein, examples of which are provided elsewhere herein. In some cases, a composition herein made from a single variant of an alpha casein comprises only a truncated form of the alpha S1 casein protein.

In some cases, the single variant of an alpha casein in compositions (such as cheese analogues) comprises greater than 0% truncated forms, such as 0.1%, 0.2%, 0.5%, 0.8% wt/wt of the single variant of an alpha casein is a truncated form(s) of the alpha S1 protein. In some embodiments, the single variant of an alpha S1 casein comprises at least 1% wt/wt of one or more truncated forms of the alpha S1 casein. In some cases, the single variant of an alpha S1 casein comprises at most 20% wt/wt of one or more truncated forms of the alpha S1 casein. In some cases, the single variant of an alpha S1 casein comprises 1% to 3%, 1% to 5%, 1% to 7%, 1% to 10%, 1% to 12%, 1% to 15%, 1% to 20%, 3% to 5%, 3% to 7%, 3% to 10%, 3% to 12%, 3% to 15%, 3% to 20%, 5% to 7%, 5% to 10%, 5% to 12%, 5% to 15%, 5% to 20%, 7% to 10%, 7% to 12%, 7% to 15%, 7% to 20%, 10% to 12%, 10% to 15%, 10% to 20%, 12% to 15%, 12% to 20%, or 15% to 20% wt/wt of one or more truncated forms of the alpha S1 casein. In some cases, the single variant of an alpha S1 casein comprises of about 1%, 3%, 5%, 7%, 10%, 12%, 15%, or 20% wt/wt of one or more truncated forms of the alpha S1 casein. In some cases, the single variant of an alpha S1 casein comprises of at least 1%, 3%, 5%, 7%, 10%, 12% or 15% wt/wt of one or more truncated forms of the alpha S1 casein. In some cases, the single variant of an alpha S1 casein comprises of at most 3%, 5%, 7%, 10%, 12%, 15% or 20% wt/wt of one or more truncated forms of the alpha S1 casein. In such compositions, the remaining percentage of alpha S1 casein in the single variant of an alpha casein is the full-length form of the alpha S1 casein.

Post Translational Modifications

Depending on the host organism used to express the alpha casein, the single variant of alpha casein proteins may have a glycosylation or phosphorylation pattern (post-translational modifications) different from animal-derived alpha casein proteins. In some cases, the single variant of alpha casein protein comprises no post translational modifications (PTMs). In some cases, the single variant of alpha casein protein comprises substantially reduced PTMs. As used herein, substantially reduced PTMs means at least 50% reduction of one or more types of PTMs as compared to the amount of PTMs in an animal-derived alpha casein protein. For instance, the single variant of alpha casein protein may be 50%, 55%, 60%, 65%, 70%, 75%, 80%, 85%, 90%, 92%, 95%, 97%, 99% less post-translationally modified as compared to animal-derived alpha casein. In some cases, the post-translationally modified caseins may be lacking one or more sites of post translational modifications found in animal-derived casein proteins.

In some cases, the single variant of alpha casein protein comprises one or more PTMs that differ from an animal-derived alpha casein protein, for example, a modification at an amino acid within the single variant of alpha casein protein that is not modified in the animal-derived alpha casein protein or a modification that differs in chemical structure as compared to the animal-derived alpha casein protein, such as a different phosphorylation structure.

Alternatively, the single variant of alpha casein protein may comprise PTMs comparable to animal-derived alpha casein PTMs. In some cases, the single variant of alpha casein protein comprises substantially increased PTMs. As used herein, substantially increased PTMs means at least 5% increase in one or more types of PTMs as compared to the amount of PTMs in an animal-derived alpha casein protein. For instance, the single variant of alpha casein proteins may be 5%, 10%, 20%, 30%, 40%, 50%, 60%, 70%, 80%, 90%, 95%, 97%, 99% more post-translationally modified as compared to animal-derived alpha casein.

The PTMs in the alpha casein protein may be modified chemically or enzymatically. In some cases, the single variant of alpha casein protein comprises substantially reduced or no PTMs without chemical or enzymatic treatment. Compositions may be generated using single variant of alpha casein protein with reduced or no PTMs, wherein the lack of PTMs is not due to chemical or enzymatic treatments of the protein, such as producing a single variant of alpha casein protein through recombinant production where the recombinant protein lacks PTMs.

The phosphorylation in the single variant of alpha casein protein may be modified chemically or enzymatically. In some cases, the single variant of alpha casein protein comprises substantially reduced or no phosphorylation without chemical or enzymatic treatment. For instance, single variant of alpha casein proteins may be 50%, 55%, 60%, 65%, 70%, 75%, 80%, 85%, 90%, 92%, 95%, 97%, 99% less phosphorylated as compared to animal-derived alpha casein. Compositions may be generated using single variant of alpha casein protein with reduced or no phosphorylation, wherein the lack of phosphorylation is not due to chemical or enzymatic treatments, such as where recombinant production provides single variant of alpha casein protein with reduced or no phosphorylation.

Compositions may be generated using a single variant of alpha caseins which is a mixture of alpha caseins with different PTMs. For instance, compositions may comprise single variants of alpha casein may comprise a mix of alpha caseins with no PTMs, reduced PTMs, nature comparable (or native-like) PTMs and/or increased PTMs. In some cases, compositions may comprise single variants of alpha casein proteins with native (nature comparable or animal-derived) PTMs, alpha casein proteins lacking one or more types of PTMs, and/or no PTMs. Alternatively, compositions may comprise a single variant of alpha casein proteins with uniform PTMs. The PTM structures in such cases may include reduced PTMs, PTMs lacking one or more types of PTM. For instance, the consumable composition may comprise only a single variant of alpha casein with reduced phosphorylation.

II. Consumable Compositions

A. Cheese and Cheese-Like Analogues

The compositions of single variant of alpha casein described in this application may be used to create cheese analogues. A cheese analogue may comprise ingredients in addition to a recombinantly produced single variant of an alpha casein protein. In some cases, a cheese analogue may comprise solvents such as water, fats, salts, starch, sugars, flavors, acids, pH stabilizers, carbohydrates, etc. A cheese analogue may comprise proteins other than the single variant of alpha casein. For instance, the other proteins may comprise proteins (other than caseins) found in animal-derived dairy products. Alternatively, a cheese analogue may comprise proteins that are not found in animal-derived dairy products, such examples may include but are not limited to plant proteins.

A cheese analogue described herein may comprise from 5% w/w to about 30% w/w of a recombinant single variant of an alpha casein. In some cases, a cheese analogue may comprise at least 5% w/w of a recombinant single variant of an alpha casein, such as any of the single variant of alpha caseins described herein. In some cases, a cheese analogue may comprise at most 30% w/w of a recombinant single variant of an alpha casein. In some cases, a cheese analogue may comprise from 5% to 7%, 5% to 10%, 5% to 15%, 5% to 20%, 5% to 25%, 5% to 30%, 7% to 10%, 7% to 15%, 7% to 20%, 7% to 25%, 7% to 30%, 10% to 15%, 10% to 20%, 10% to 25%, 10% to 30%, 15% to 20%, 15% to 25%, 15% to 30%, 20% to 25%, 20% to 30%, or 25% to 30% w/w of a recombinant single variant of an alpha casein. In some cases, a cheese analogue may comprise about 5%, 7%, 10%, 15%, 20%, 25%, or 30% w/w of a recombinant single variant of alpha casein.

In some cases, a cheese analogue may comprise 5% w/w to 40% w/w fats. Examples of fats which can be added to a cheese analogue include coconut, canola, high-oleic sunflower, palm oils. Other examples are provided elsewhere herein. In some cases, a cheese analogue may comprise at least 5% w/w fats. In some cases, a cheese analogue may comprise at most 40% w/w fats. In some cases, a cheese analogue may comprise from 5% w/w to 10% w/w, 5% w/w to 15% w/w, 5% w/w to 20% w/w, 5% w/w to 25% w/w, 5% w/w to 30% w/w, 5% w/w to 40% w/w, 10% w/w to 15% w/w, 10% w/w to 20% w/w, 10% w/w to 25% w/w, 10% w/w to 30% w/w, 10% w/w to 40% w/w, 15% w/w to 20% w/w, 15% w/w to 25% w/w, 15% w/w to 30% w/w, 15% w/w to 40% w/w, 20% w/w to 25% w/w, 20% w/w to 30% w/w, 20% w/w to 40% w/w, 25% w/w to 30% w/w, 25% w/w to 40% w/w, or 30% w/w to 40% w/w fats. In some cases, a cheese analogue may comprise about 5% w/w, 10% w/w, 15% w/w, 20% w/w, 25% w/w, 30% w/w, or 40% w/w fats.

In some cases, a cheese analogue may comprise 0% w/w to 50% w/w starch. Examples of starches which can be added to a cheese analogue include modified potato, corn. Other examples are provided elsewhere herein. In some cases, a cheese analogue may comprise at least 0% w/w starch. In some cases, a cheese analogue may comprise at most 50% w/w starch. In some cases, a cheese analogue may comprise from 0% w/w to 10% w/w, 0% w/w to 20% w/w, 0% w/w to 30% w/w, 0% w/w to 40% w/w, 0% w/w to 50% w/w, 10% w/w to 20% w/w, 10% w/w to 30% w/w, 10% w/w to 40% w/w, 10% w/w to 50% w/w, 20% w/w to 30% w/w, 20% w/w to 40% w/w, 20% w/w to 50% w/w, 30% w/w to 40% w/w, 30% w/w to 50% w/w, or 40% w/w to 50% w/w starch. In some cases, a cheese analogue may comprise about 0% w/w, 10% w/w, 20% w/w, 30% w/w, 40% w/w, or 50% w/w starch.

Preferentially, a cheese analogue may comprise at most 30% w/w starch. In some cases, a cheese analogue may comprise 0% w/w to 30% w/w starch. In some cases, a cheese analogue may comprise at least 0% w/w starch. In some cases, a cheese analogue may comprise 0% w/w to 5% w/w, 0% w/w to 10% w/w, 0% w/w to 15% w/w, 0% w/w to 20% w/w, 0% w/w to 25% w/w, 0% w/w to 30% w/w, 5% w/w to 10% w/w, 5% w/w to 15% w/w, 5% w/w to 20% w/w, 5% w/w to 25% w/w, 5% w/w to 30% w/w, 10% w/w to 15% w/w, 10% w/w to 20% w/w, 10% w/w to 25% w/w, 10% w/w to 30% w/w, 15% w/w to 20% w/w, 15% w/w to 25% w/w, 15% w/w to 30% w/w, 20% w/w to 25% w/w, 20% w/w to 30% w/w, or 25% w/w to 30% w/w starch. In some cases, a cheese analogue may comprise 0% w/w, 5% w/w, 10% w/w, 15% w/w, 20% w/w, 25% w/w, or 30% w/w starch.

In some cases, a cheese analogue may comprise 0% w/w to 16% w/w salts such as calcium salts, emulsifying salts, table salts, etc. Examples of such salts are also provided elsewhere herein.

In some cases, a cheese analogue may comprise calcium salts such as calcium chloride. In some cases, a cheese analogue may comprise 0.1% to 6% w/w calcium salts. In some cases, a cheese analogue may comprise at least 0.1% w/w calcium salts. In some cases, a cheese analogue may comprise at most 6% w/w calcium salts. In some cases, a cheese analogue may comprise 0.1% to 1%, 0.1% to 2%, 0.1% to 3%, 0.1% to 4%, 0.1% to 5%, 0.1% to 6%, 1% to 2%, 1% to 3%, 1% to 4%, 1% to 5%, 1% to 6%, 2% to 3%, 2% to 4%, 2% to 5%, 2% to 6%, 3% to 4%, 3% to 5%, 3% to 6%, 4% to 5%, 4% to 6%, or 5% to 6% w/w calcium salts. In some cases, a cheese analogue may comprise about 0.1%, 1%, 2%, 3%, 4%, 5%, or 6% w/w calcium salts. In some cases, a cheese analogue may comprise less than 0.1%, 1%, 2%, 3%, 4%, 5%, or 6% w/w calcium salts. In some cases, a cheese analogue may comprise more than 0.1%, 1%, 2%, 3%, 4% or 5% w/w calcium salts. In some cases, a cheese analogue may comprise calcium ions. The calcium ions may be added to a cheese analogue in the form of a calcium-based salt, for instance, calcium chloride. In some cases, a cheese analogue may comprise 0% to 0.6% w/w calcium ions. In some cases, a cheese analogue may comprise at least 0% w/w calcium ions. In some cases, a cheese analogue may comprise at most 0.6% w/w calcium ions. In some cases, a cheese analogue may comprise 0% to 0.1%, 0% to 0.2%, 0% to 0.3%, 0% to 0.4%, 0% to 0.5%, 0% to 0.6%, 0.1% to 0.2%, 0.1% to 0.3%, 0.1% to 0.4%, 0.1% to 0.5%, 0.1% to 0.6%, 0.2% to 0.3%, 0.2% to 0.4%, 0.2% to 0.5%, 0.2% to 0.6%, 0.3% to 0.4%, 0.3% to 0.5%, 0.3% to 0.6%, 0.4% to 0.5%, 0.4% to 0.6%, or 0.5% to 0.6% w/w calcium ions. In some cases, a cheese analogue may comprise about 0%, 0.1%, 0.2%, 0.3%, 0.4%, 0.5%, or 0.6% w/w calcium ions. In some cases, a cheese analogue may comprise at least 0.1%, 0.2%, 0.3%, 0.4%, 0.5%, or 0.6% w/w calcium ions. In some cases, a cheese analogue may comprise at most 0.1%, 0.2%, 0.3%, 0.4%, or 0.5% w/w calcium ions.

In some cases, a cheese analogue may comprise 0 mg to 30 mg calcium ions per gram of casein. In some cases, a cheese analogue may comprise at least 0 mg calcium ions per gram of casein. In some cases, a cheese analogue may comprise at most 30 mg calcium ions per gram of casein. In some cases, a cheese analogue may comprise 0 mg to 5 mg, 0 mg to 10 mg, 0 mg to 15 mg, 0 mg to 20 mg, 0 mg to 25 mg, 0 mg to 30 mg, 5 mg to 10 mg, 5 mg to 15 mg, 5 mg to 20 mg, 5 mg to 25 mg, 5 mg to 30 mg, 10 mg to 15 mg, 10 mg to 20 mg, 10 mg to 25 mg, 10 mg to 30 mg, 15 mg to 20 mg, 15 mg to 25 mg, 15 mg to 30 mg, 20 mg to 25 mg, 20 mg to 30 mg, or 25 mg to 30 mg calcium ions per gram of casein. In some cases, a cheese analogue may comprise 0 mg, 5 mg, 10 mg, 15 mg, 20 mg, 25 mg, or 30 mg calcium ions per gram of casein. In some cases, a cheese analogue may comprise at least 1 mg, 5 mg, 10 mg, 15 mg, 20 mg, 25 mg, or 30 mg calcium ions per gram of casein. In some cases, a cheese analogue may comprise at most 1 mg, 5 mg, 10 mg, 15 mg, 20 mg, 25 mg, or 30 mg calcium ions per gram of casein.

In some cases, a cheese analogue may comprise emulsifying salts such as disodium phosphate, trisodium citrate or other emulsifying salts. In some cases, a cheese analogue may comprise 0.1% to 6% w/w emulsifying salts. In some cases, a cheese analogue may comprise at least 0.1% w/w emulsifying salts. In some cases, a cheese analogue may comprise at most 6% w/w emulsifying salts. In some cases, a cheese analogue may comprise 0.1% to 1%, 0.1% to 2%, 0.1% to 3%, 0.1% to 4%, 0.1% to 5%, 0.1% to 6%, 1% to 2%, 1% to 3%, 1% to 4%, 1% to 5%, 1% to 6%, 2% to 3%, 2% to 4%, 2% to 5%, 2% to 6%, 3% to 4%, 3% to 5%, 3% to 6%, 4% to 5%, 4% to 6%, or 5% to 6% w/w emulsifying salts. In some cases, a cheese analogue may comprise about 0.1%, 1%, 2%, 3%, 4%, 5%, or 6% w/w emulsifying salts. In some cases, a cheese analogue may comprise less than 0.1%, 1%, 2%, 3%, 4%, 5%, or 6% w/w emulsifying salts. In some cases, a cheese analogue may comprise more than 0.1%, 1%, 2%, 3%, 4% or 5% w/w emulsifying salts.

In some cases, a cheese analogue may comprise table salts such as sodium chloride salts. In some cases, a cheese analogue may comprise 0.1% to 4% w/w sodium chloride. In some cases, a cheese analogue may comprise at least 0.1% w/w sodium chloride. In some cases, a cheese analogue may comprise at most 4% w/w sodium chloride. In some cases, a cheese analogue may comprise 0.1% to 1%, 0.1% to 2%, 0.1% to 3%, 0.1% to 4%, 1% to 2%, 1% to 3%, 1% to 4%, 2% to 3%, 2% to 4%, or 3% to 4% w/w sodium chloride. In some cases, a cheese analogue may comprise about 0.1%, 1%, 2%, 3%, or 4% w/w sodium chloride. In some cases, a cheese analogue may comprise less than 0.1%, 1%, 2%, 3%, or 4% w/w sodium chloride. In some cases, a cheese analogue may comprise more than 0.1%, 1%, 2% or 3% w/w sodium chloride.

In some examples, a single variant of alpha casein recombinantly produced (5-30% w/w of the cheese analogue) (exemplary optimal range 10-20% w/w) may be combined with water (30-65% w/w) (exemplary optimal range 45-55% w/w), fats (5-40% w/w) (exemplary optimal range 20-25% w/w), sodium chloride (salt) (0-4% w/w) (exemplary optimal range 0-1.5% w/w), calcium chloride (0-6% w/w) (exemplary optimal range 0-1.5% w/w), emulsifying salts (disodium phosphate, trisodium citrate) (0-6% w/w) (exemplary optimal range 0-3% w/w), starch (0-50% w/w) (exemplary optimal range 0-8% w/w), natural vegan flavors (0-5% w/w) (exemplary optimal range 0.5-1% w/w), and acid (0-5% w/w) (exemplary optimal range 0-1% w/w). Optional ingredients such as plant-based or other animal-free protein (0-30%) (exemplary optimal range 0-8% w/w), hydrocolloids (0-5%) (exemplary optimal range 0-2%), sugars such as mono-, di- and oligosaccharides (0-5% w/w) (exemplary optimal range 0-2% w/w), emulsifying agents such as mono- and diglycerides (0-2% w/w) (exemplary optimal range 0-0.5% w/w), natural flavor maskers, color additives (0-5% w/w), preservatives (0-1% w/w), anti-caking agents (0-2% w/w) and micronutrients such as vitamins (0-1%) can be incorporated into a cheese analogue as well.

In some embodiments, the following ingredients are pre-mixed: a recombinantly produced single variant of an alpha casein, fat(s), water, starch, salt(s) such as sodium chloride. In some embodiments, pH adjustment is performed at this stage to bring the composition to neutral pH, 6.8-7.2, using a pH adjuster such as sodium hydroxide (lye). Optional ingredients such as plant-based or other animal-free protein, sugars, hydrocolloids and emulsifying agents can be added at this step or at a later stage. Pre-mixing can occur at ambient or elevated temperatures (15-50° C.). In some cases, fats are pre-melted [30-70° C.] (exemplary optimal range 40-50° C.) and held at their melting temperature prior to incorporation. The calcium chloride and emulsifying salts may be added at the pre-mixing stage or at a later stage. Alternatively, the calcium chloride and emulsifying salts may be added consecutively, in any order: calcium chloride may be added before or after emulsifying salts. For instance, calcium chloride and emulsifying salts may be added in 2 stages over the course of 4 minutes to 1 hour (exemplary optimal range 10 to 20 minutes), with 2 minute to 30 minute (exemplary optimal range 5 to 10 min) incubation intervals at ambient or elevated temperature. Alternatively, a cheese analogue may be produced without calcium chloride or emulsifying salts. Calcium chloride can also be added at the end of the cheese analogue making process, before or after the acid addition.

The mixtures may be heated over a temperature ramp from pre-mixing temperature (ambient or elevated) to 50-95° C. (exemplary optimal range 75-90° C.), over a ramp period of 1 to 30 minutes (exemplary optimal range 1 to 5 mins), while being mixed mechanically. Heated mixtures may then be held for 0 to 20 minutes (exemplary optimal range 2-5 mins) at the final ramp temperature as ingredients are mechanically incorporated to form an emulsion. Mechanical incorporation (mixing) can be achieved using a variety of mixers, such as a vertical cutter mixer or a twin-screw mixer.

The acidity of the mixtures may be regulated by incorporating an acid, such as lactic or citric acid and continuing to mix briefly, to a final pH of about 5-6.5 (exemplary optimal range 5.7-6.2). Acidity may also be regulated by using glucono-delta-lactone earlier in the mixing process. The resulting mixtures may then be set into moulds, other shaping containers, or vacuum seal packaging. The resulting product may be chilled to 4° C. immediately after portioning into moulds to create the cheese analogue. Such cheese analogues can then be used as food products, toppings and incorporated into other food products.

In some embodiments, the amount of salts or minerals in a cheese may be altered to generate favorable qualities. For instance, in one example, an amount of calcium may be altered to improve melt, texture, stretch, etc. In one example, the amount of calcium in a cheese analogue may be reduced to improve the melt of the cheese analogue. In another example, the amount of calcium may be increased in a cheese analogue to improve the texture or stretch of the cheese analogue.

The texture of a cheese analogue made with a single variant of alpha casein, such as by methods described herein, may be comparable to the texture of a similar type of cheese made using animal-derived dairy proteins, such as cheese made from animal milk. Texture of a cheese analogue made using the compositions described herein having a single variant of alpha casein may be comparable to the texture of a cheese or cheese analogue made using micelles, such as cheese made from milk, or cheese analogue made from caseinate or rennet casein. Texture of a cheese analogue made using the compositions described herein having a single variant of alpha casein may be improved/more desirable when compared to the texture of a cheese or cheese analogue made using micelles, such as cheese made from milk, or cheese analogue made from caseinate or rennet casein or a plant-derived cheese analogue. Texture of a cheese analogue may be tested using a trained panel of human subjects or using a machine such as a texture analyzer.

The taste of a cheese analogue made with a single variant of alpha casein, such as by methods described herein may be comparable to the taste of a similar type of cheese made using animal-derived dairy proteins, such as cheese made from animal milk. Taste of a cheese analogue made using the compositions described herein having a single variant of alpha casein may be comparable to the taste of a cheese or cheese analogue made using micelles, such as cheese made from milk, or cheese analogue made from caseinate or rennet casein. Taste of a cheese analogue made using the compositions described herein having a single variant of alpha casein may be improved when compared to the taste of a cheese or cheese analogue made using a plant-derived cheese analogue. Taste of a cheese may be tested using a trained panel of human subjects.

Cheese analogue compositions described herein having a single variant of alpha casein may have a browning ability which is comparable to a similar type of cheese made using animal-derived dairy proteins, such as cheese made from animal milk. Cheese analogue compositions described herein having a single variant of alpha casein may have a browning ability which is comparable to a similar type of cheese or cheese analogue made using micelles, such as cheese made from milk, or cheese analogue made from caseinate or rennet casein. Cheese analogue compositions described herein having a single variant of alpha casein may have a browning ability which is improved when compared to a similar type of cheese or cheese analogue made using a plant-derived cheese analogue. Browning ability of a cheese analogue may be tested using an oven and computer imaging.

Cheese analogue compositions described herein having a single variant of alpha casein may have a melting ability which is comparable to a similar type of cheese made using animal-derived dairy proteins, such as cheese made from animal milk. Cheese analogue compositions described herein having a single variant of alpha casein may have a melting ability which is comparable to a similar type of cheese or cheese analogue made using micelles, such as cheese made from milk, or cheese analogue made from caseinate or rennet casein. Cheese analogue compositions described herein having a single variant of alpha casein may have a melting ability which is improved when compared to a similar type of cheese or cheese analogue made using a plant-derived cheese analogue. Melting ability of a cheese analogue may be tested using a melting station and/or oven and computer imaging.

The stretching ability of a cheese analogue made with a single variant of alpha casein, such as by methods described herein, may be comparable to the stretching ability of a similar type of cheese made using animal-derived dairy proteins, such as cheese made from animal milk. Stretching ability of a cheese made using the compositions described herein having a single variant of alpha casein may be comparable to the stretching ability of a cheese or cheese analogue made using micelles, such as cheese made from milk, or cheese analogue made from caseinate or rennet casein. Stretching ability of a cheese made using the compositions described herein having a single variant of alpha casein may be improved/more desirable when compared to the stretching ability of a cheese or cheese analogue made using micelles, such as cheese made from milk, or cheese analogue made from caseinate or rennet casein or a plant-derived cheese analogue. Stretching ability of a cheese may be tested using a trained panel of human subjects or using a machine such as a texture analyzer.

The hardness of a cheese analogue made with a single variant of alpha casein such as by methods described herein may be comparable to the hardness of a similar type of cheese made using animal-derived dairy proteins, such as cheese made from animal milk. Hardness of a cheese analogue made using the compositions described herein having a single variant of alpha casein may be comparable to the hardness of a cheese or cheese analogue made using micelles, such as cheese made from milk, or cheese analogue made from caseinate or rennet casein. Hardness of a cheese analogue made using the compositions described herein having a single variant of alpha casein may be improved when compared to the hardness of a cheese or cheese analogue made using a plant-derived cheese analogue. Hardness of a cheese analogue may be tested using a trained panel of human subjects or using a machine such as a texture analyzer.

The adhesiveness of a cheese analogue made with a single variant of alpha casein such as by methods described herein may be comparable to the adhesiveness of a similar type of cheese made using animal-derived dairy proteins, such as cheese made from animal milk. Adhesiveness of a cheese analogue made using the compositions described herein having a single variant of alpha casein may be comparable to the adhesiveness of a cheese or cheese analogue made using micelles, such as cheese made from milk, or cheese analogue made from caseinate or rennet casein. Adhesiveness of a cheese analogue made by methods described herein having a single variant of alpha casein may be reduced when compared to adhesiveness of a cheese or cheese analogue made using micelles, such as cheese made from milk, or cheese analogue made from caseinate or rennet casein. Adhesiveness of a cheese analogue made by methods described herein having a single variant of alpha casein may be reduced when compared to adhesiveness of a plant-derived cheese analogue. Adhesiveness of a cheese analogue may be tested using a trained panel of human subjects or using a machine such as a texture analyzer.

The creaminess of a cheese analogue made with a single variant of alpha casein such as by methods described herein may be comparable to the creaminess of a similar type of cheese made using animal-derived dairy proteins, such as cheese made from animal milk. Creaminess of a cheese analogue made using the compositions described herein having a single variant of alpha casein may be comparable to the creaminess of a cheese or cheese analogue made using micelles, such as cheese made from milk, or cheese analogue made from caseinate or rennet casein. Creaminess of a cheese analogue made using the compositions described herein having a single variant of alpha casein may be improved when compared to the creaminess of a cheese or cheese analogue made using a plant-derived cheese analogue. Creaminess of a cheese analogue may be tested using a trained panel of human subjects or using a machine such as a texture analyzer.

The mouthfeel of a cheese analogue made with a single variant of alpha casein such as by methods described herein may be comparable to the mouthfeel of a similar type of cheese made using animal-derived dairy proteins, such as cheese made from animal milk. Mouthfeel of a cheese analogue made using the compositions described herein having a single variant of alpha casein may be comparable to the mouthfeel of a cheese or cheese analogue made using micelles, such as cheese made from milk, or cheese analogue made from caseinate or rennet casein. Mouthfeel of a cheese analogue made using the compositions described herein having a single variant of alpha casein may be improved when compared to the mouthfeel of a cheese or cheese analogue made using a plant-derived cheese analogue. Mouthfeel of a cheese analogue may be tested using a trained panel of human subjects or using a machine such as a texture analyzer.

The cheese analogue or similar compositions described herein may be low-moisture cheese analogues. For instance, the low moisture cheese analogue may comprise from 45-52% w/w moisture. The low moisture cheese analogue may comprise less than 52% w/w moisture.

B. Other Consumable Compositions

In some embodiments, analogues of dairy or dairy-like products may be produced using compositions comprising a single variant of an alpha casein protein described herein. Dairy or dairy-like analogue products which can be made using the compositions described herein may include analogues of milk, cream, milkshakes, creamers, ice cream, condensed milk, yogurt or cheese. Cheese analogues or cheese-like products which do not come from real curd or were not made via coagulation of a liquid colloid may also be made using the compositions comprising a single variant of an alpha casein protein, comprising the full-length single variant of alpha casein and optionally truncated forms thereof described herein.

The compositions described herein may be used to generate consumable analogue compositions such as milk or milk-like compositions. For instance, a single variant of an alpha casein may be used to form a milk-like analogue product without the formation of a micelle or a micelle-like composition. Milk-like analogue products made using the compositions described herein may provide similar or equivalent features (such as texture, creaminess and taste) as compared to an animal milk, or a milk-like analogue product made using micelles, such as one made from caseinate or rennet casein. Milk-like analogue products made using the compositions described herein may provide improvement in one or more features (such as texture, creaminess and taste) as compared to a plant-derived milk analogue.

The single variant alpha casein compositions described herein may be used to generate consumable compositions such as yogurt analogues or yogurt-like compositions. For instance, single variant alpha casein compositions may be used to form a yogurt analogue product. Yogurt analogue products may be formed without the formation of a micelle or a micelle-like composition. Yogurt analogue products made using the compositions described herein may provide similar or equivalent features (such as texture, creaminess and taste) to an animal-derived dairy yogurt or a dairy yogurt analogue made using micelles such as one made from caseinate or rennet casein. Yogurt analogue products made using the compositions described herein may provide an improvement in one or more features (such as texture, creaminess and taste) when compared to a plant-derived yogurt analogue.

The single variant alpha casein compositions described herein may be used to generate consumable compositions such as dairy cream analogues or cream-like compositions. For instance, single variant alpha casein compositions may be used to form a dairy cream analogue product. Dairy cream analogue products may be formed without the formation of a micelle or a micelle-like composition. Cream analogue products made using the compositions described herein may provide similar or equivalent features (such as texture, creaminess and taste) to an animal-derived dairy cream, or a dairy cream analogue made using micelles such as one made from caseinate or rennet casein. Cream analogue products made using the compositions described herein may provide an improvement in one or more features (such as texture, creaminess and taste) when compared to a plant-derived cream analogue.

The compositions described herein may be used to generate consumable compositions such as ice cream analogue compositions. For instance, single variant alpha casein compositions may be used to form an ice cream analogue product. Ice cream analogue products may be formed without the formation of a micelle or a micelle-like composition. Ice cream analogue products made using the compositions described herein may provide similar or equivalent to an animal-derived dairy ice cream analogue or an ice cream analogue made using micelles, such as one made from caseinate or rennet casein. Ice cream analogue products made using the compositions described herein may provide an improvement in one or more features (such as texture, creaminess and taste) when compared to a plant-derived ice cream analogue.

The compositions described herein may be used to generate various consumable compositions, including but not limited to beverages (such as nutritional drinks, dairy-related drinks, etc.), salad dressings, baking ingredients, cooking ingredients, etc. For instance, the single variant alpha casein compositions described herein may be used to generate a yogurt beverage, a ranch dressing, etc. As an additional example, the single variant alpha casein compositions described herein may be used to generate ingredients used for baking and cooking.

C. Other components

The compositions described herein may be used as ingredients in generating consumable compositions such as food products. The food products may include cheese-analogues, yogurt analogue products, and other food products described elsewhere herein. Such consumable compositions may comprise one or more ingredients in addition to the single variant alpha casein protein. The ingredients may include but are not limited to solvents, salts, sugar, fats, flavorings, colorants, etc.

The consumable compositions comprising a single variant alpha casein protein may comprise salts such as calcium, phosphorous, citrate, potassium, sodium and/or chloride salts. The calcium salt may be selected from calcium chloride, calcium carbonate, calcium citrate, calcium glubionate, calcium lactate, calcium gluconate, calcium acetate, equivalents thereof and/or combinations thereof. The phosphate salt may be selected from orthophosphates such as monosodium (dihydrogen) phosphate, disodium phosphate, trisodium phosphate, monopotassium (dihydrogen) phosphate, dipotassium phosphate, tripotassium phosphate; pyrophosphates such as disodium or dipotassium pyrophosphate, trisodium or tripotassium pyrophosphate, tetrasodium or tetrapotassium pyrophosphate; polyphosphates such as pent sodium or potassium tripolyphosphate, sodium or potassium tetrapolyphosphate, sodium or potassium hexametaphosphate. The citrate salt may be selected from calcium citrate, potassium citrate, sodium citrate, trisodium citrate, tripotassium citrate or equivalents thereof. The consumable composition may comprise a combination of salts. In some embodiments, the consumable composition comprises calcium, phosphate and citrate salts. In some embodiments, the consumable composition comprises calcium and phosphate salts. In some embodiments, the consumable composition comprises calcium and citrate salts. In some embodiments, the consumable composition comprises phosphate and citrate salts.

In some embodiments, fat is added to the consumable composition. In some cases, fats may be essentially free of animal-derived fats. Fats used herein may include plant-based fats such as canola oil, sunflower oil, coconut oil, palm oil, or combinations thereof. Fats used herein may include microbially-made recombinant animal or plant fats. Fats used herein may include mammalian cell-cultured recombinant animal or plant fats.

Consumable composition as described herein may further comprise sugars. Sugars used herein may include plant-based monosaccharides, disaccharides and/or oligosaccharides. Examples of sugars include sucrose, glucose, fructose, galactose, lactose, maltose, mannose, allulose, tagatose, xylose, and arabinose.

The consumable food compositions made from a single variant alpha casein protein described herein and the methods of making such compositions may including adding or mixing with one or more ingredients. For example, food additives may be added in or mixed with the compositions. Food additives can add volume and/or mass to a composition. A food additive may improve functional performance and/or physical characteristics. For example, a food additive may prevent gelation or increased viscosity due to the lipid portion of the lipoproteins in the freeze-thaw cycle. An anticaking agent (cellulose, potato starch, corn starch, starch blends) may be added to make a free-flowing composition. Carbohydrates can be added to increase resistance to heat damage, e.g., less protein denaturation during drying and improve stability and flowability of dried compositions. Food additives include, but are not limited to, starch (e.g., potato, modified potato, corn, rice), food coloring, pH adjuster (e.g. glucono-delta-lactone, sodium hydroxide), natural flavouring (e.g., mozzarella, parmesan, butter, cream, colby, provolone, asiago, etc.), artificial flavoring, flavor enhancer, flavour maskers, batch marker, food acid (e.g., lactic acid, citric acid), filler, anticaking agent (e.g., sodium silicoaluminate), antigreening agent (e.g., citric acid), food stabilizer, foam stabilizer or binding agent, antioxidant, acidity regulatory, bulking agent, color retention agent, whipping agent (e.g., ester-type whipping agent, triethyl citrate, sodium lauryl sulfate), emulsifier (e.g., lecithin, monoglycerides, diglycerides), humectant, thickener, pharmaceutical excipient, solid diluent, nutrient, sweetener, glazing agent, preservative (e.g., sorbic acid, nisin), vitamins (e.g. vitamin B, vitamin D, vitamin A), dietary elements, carbohydrates, polyol, gums, starches, flour, oil, and bran. In some cases, flavoring may comprise a mozzarella flavoring, cheddar flavoring, parmesan flavoring or other similar cheese flavorings.

Food coloring includes, but is not limited to, FD&C Yellow #5, FD&C Yellow #6, FD&C Red #40, FD&C Red #3, FD&C Blue No. 1, FD&C Blue No. 2, FD&C Green No. 3, carotenoids (e.g., saffron, β-carotene), annatto, betanin, butterfly pea, caramel coloring, chlorophyllin, elderberry juice, lycopene, carmine, pandan, paprika, turmeric, curcuminoids, quinoline yellow, carmoisine, Ponceau 4R, Patent Blue V, and Green S.

Ingredients for pH adjustment include, but are not limited to, Tris buffer, potassium phosphate, sodium hydroxide, potassium hydroxide, citric acid, sodium citrate, sodium bicarbonate, and hydrochloric acid.

D. End-User Products

Consumable compositions of a single variant alpha casein protein described herein may be used as ingredients to make a final product for an end-user. For instance, a cheese product or a cheese analogue described herein may be used by end-user to make a final product such as pizza, Italian food toppings, Mexican food toppings, frozen meals, toppings for savory baked goods, soups, macaroni cheese, cheese sticks, etc.

Recombinant Expression

One or more proteins used in the formation of cheese compositions may be produced recombinantly. In some cases, a single variant alpha casein protein (e.g., a single variant of alpha S1 or a single variant of alpha S2) is produced recombinantly. The single variant alpha casein protein, e.g., a single variant alpha S1 casein protein or a single variant alpha S2 casein protein can have an amino acid sequence from any species. For example, a recombinant alpha casein protein may have an amino acid sequence of cow, sheep, goat, buffalo, horse, human, deer or camel alpha casein. The nucleotide sequence encoding the alpha casein protein may be codon-optimized for increased efficiency of production. Exemplary alpha casein protein sequences are provided in Table 1 below for use in recombinant production of a single variant alpha casein protein. A recombinant single variant alpha casein protein can be a non-naturally occurring variant of an alpha casein. Such variant can comprise one or more amino acid insertions, deletions, or substitutions relative to a native alpha casein sequence.

Such a variant can have at least 70%, 75%, 80%, 85%, 90%, 95%, 96%, 97%, 98%, or 99% sequence identity to SEQ ID NOs: 1-56. In some cases, a variant may be a truncated form of the alpha S1 casein protein such as one with at least 70%, 75%, 80%, 85%, 90%, 95%, 96%, 97%, 98%, or 99% sequence identity to SEQ ID NO.: 4-12, 16-24.

A recombinant single variant alpha casein protein, such as a single variant alpha S1 casein protein, is recombinantly expressed in a host cell. As used herein, a "host" or "host cell" denotes any protein production host selected or genetically modified to produce a desired product. Exemplary hosts include bacteria, yeast, fungi, plants, insects and mammalian cells. In some cases, a bacterial host cell such as *Lactococcus lactis, Bacillus subtilis* or *Escherichia coli* may be used to produce alpha casein proteins and/or its truncated forms. Other host cells include bacterial host such as, but not limited to, Lactococci sp., *Bacillus amyloliquefaciens, Bacillus licheniformis* and *Bacillus megaterium, Brevibacillus choshinensis, Mycobacterium smegmatis, Rhodococcus erythropolis* and *Corynebacterium glutamicum*, Lactobacilli sp., *Lactobacillus fermentum, Lactobacillus casei, Lactobacillus acidophilus, Lactobacillus plantarum* and *Synechocystis* sp. 6803.

In some embodiments, a full-length single variant alpha casein protein and/or truncated forms thereof are produced recombinantly in a host cell. For example, full-length and truncated single variant alpha S1 casein proteins may be produced in the same host cell and such production can originate from the same open reading frame (i.e., the same expression cassette) and truncated forms generated for example, by post-translational proteolytic cleavage or produced from separate open reading frames, such as with an expression cassette encoding the full-length alpha casein variant and one or more expression cassettes encoding the truncated open reading frames for the truncated forms of the alpha casein variant. Alternatively, full-length and truncated single variant alpha S1 casein proteins may be produced in different host cells. Expression of a target protein can be provided by an expression vector, a plasmid, a nucleic acid integrated into the host genome or other means. For example, a vector for expression can include: (a) a promoter element, (b) a signal peptide, (c) a heterologous casein sequence, and (d) a terminator element.

Expression vectors that can be used for expression of casein include those containing an expression cassette with elements (a), (b), (c) and (d). In some embodiments, the signal peptide (b) and/or terminator element (d) need not be included in the vector. In some cases, a signal peptide may be part of the native signal sequence of the casein protein, for instance, the protein may comprise a native signal sequence as bolded in SEQ ID NOs: 1, 13, 25, 28, 31, 34, 37, 39, 42, 45, 48, 51 or 54. In some cases, the vector may comprise a mature protein sequence, as exemplified in SEQ ID NOs: 2, 3, 4-12, 14, 15, 16-24, 26, 27, 29, 30, 32, 33, 35, 36, 38, 40, 41, 43, 44, 46, 47, 49, 50, 52, 53, 55 or 56 with a heterologous signal sequence. In some cases, the protein may comprise no signal sequence but instead an initiator methionine, as exemplified in SEQ ID NOs: 3, 5, 7, 9, 11, 12, 15, 17, 19, 21, 23, 24, 27, 30, 33, 36, 41, 44, 47, 50, 53 or 56. In general, the expression cassette is designed to mediate the transcription of the transgene when integrated into the genome of a cognate host microorganism or when present on a plasmid or other replicating vector maintained in a host cell.

To aid in the amplification of the vector prior to transformation into the host microorganism, a replication origin (e) may be contained in the vector. To aid in the selection of microorganism stably transformed with the expression vector, the vector may also include a selection marker (f). The expression vector may also contain a restriction enzyme site (g) that allows for linearization of the expression vector prior to transformation into the host microorganism to facilitate the expression vectors stable integration into the host genome. In some embodiments the expression vector may contain any subset of the elements (b), (e), (f), and (g), including none of elements (b), (e), (f), and (g). Other expression elements and vector elements known to one of skill in the art can be used in combination or substituted for the elements described herein.

Gram-positive bacteria (such as *Lactococcus lactis* and *Bacillus subtilis*) may be used to secrete target proteins into the media, and gram-negative bacteria (such as *Escherichia coli*) may be used to secrete target proteins into periplasm or into the media. In some embodiments, the bacterially-expressed proteins expressed may not have any post-translational modifications (PTMs), which means they are not glycosylated and/or may not be phosphorylated. Both gram positive and gram negative bacteria may be used to produce proteins intracellularly. In such examples, the cells may be lysed to recover the protein.

Single variant alpha casein proteins may be expressed and produced in *L. lactis* both in a nisin-inducible expression system (regulated by PnisA promoter), lactate-inducible expression system (regulated by P170 promoter) or other similar inducible systems, as well as a constitutively expressed system (regulated by P secA promoter), wherein both are in a food-grade selection strain, such as NZ3900 using vector pNZ8149 (lacF gene supplementation/rescue principle). The secretion of functional proteins may be enabled by the signal peptide of Usp45 (SP(usp45)), the major Sec-dependent protein secreted by *L. lactis*. For example, alpha S1 casein and truncates thereof may be co-expressed or individually expressed in *L. lactis* using a synthetic operon.

*B. subtilis* has multiple intracellular and extracellular proteases, which may interfere with protein expression. In some embodiments, *B. subtilis* strains are modified to reduce the type and amount of intracellular and/or extracellular proteases, for example strains which have deletions for 7 (KO7) and 8 (WB800N) proteases, respectively, may be used.

In order to drive the recombinant protein secretion, the signal peptide of amyQ, alpha-amylase of *Clostridium thermocellum* may be used or another bacterial signal peptide known in the art. Additionally, native casein signal peptide sequences may be expressed heterologously in *B. subtilis*. Each casein protein has its own signal peptide sequence and may be used in the system. The signal proteins may be cross-combined with the casein proteins. The pHT01 vector may be used as a transformation and expression shuttle for inducible protein expression in *B. subtilis*. The vector is based on the strong $\sigma^A$-dependent promoter preceding the groES-groELoperon of *B. subtilis*, which has been converted into an efficiently controllable (IPTG-inducible) promoter by addition of the lac operator. pHT01 is an *E. coli-B. subtilis* shuttle vector that provides ampicillin resistance to *E. coli* and chloramphenicol resistance to *B. subtilis*.

Single variant alpha casein proteins may be produced in *E. coli* using safe laboratory strains such as *E. coli* BL21 (exemplary strains BL21 (DE3) or BL21 AI) or their derivatives, or a wild-type like K12 strains (exemplary strains MG1655 or W3110) or their derivatives. Inducible (such as IPTG-inducible, lactose-inducible, arabinose-inducible, rhamnose-inducible), auto-inducible (such as phosphate depletion based) and constitutive promoters may be used to drive the casein expression. Single variant alpha casein proteins may be produced intracellularly, or may be secreted into the periplasm and/or supernatant. In order to drive the recombinant protein secretion, bacterial signal peptides of Sec-dependent secretion pathway (such as OmpA, OmpC, OmpT, pelB, LamB), SRP secretion pathway (such as TolA, DsbA, DsbC, TorT) and TAT secretion pathway (such as TorA, SufI) can be used.

TABLE 1

Sequences

| SEQ ID No. | Name | Sequence |
|---|---|---|
| 1 | Bovine Aipha-S1 Casein | MKLLILTCLVAVALARPKHPIKHQGLPQEVLNENLLRFFVAPFPEVFG KEKVNELSKDIGSESTEDQAMEDIKQMEAESISSSEEIVPNSVEQKHIQ KEDVPSERYLGYLEQLLRLKKYKVPQLEIVPNSAEERLHSMKEGIHAQ QKEPMIGVNQELAYFYPELFRQFYQLDAYPSGAWYYVPLGTQYTDA PSFSDIPNPIGSENSEKTTMPLW |
| 2 | Bovine Alpha-S1 Casein Mature protein | RPKHPIKHQGLPQEVLNENLLRFFVAPFPEVFGKEKVNELSKDIGSEST EDQAMEDIKQMEAESISSSEEIVPNSVEQKHIQKEDVPSERYLGYLEQ LLRLKKYKVPQLEIVPNSAEERLHSMKEGIHAQQKEPMIGVNQELAYF YPELFRQFYQLDAYPSGAWYYVPLGTQYTDAPSFSDIPNPIGSENSEK TTMPLW |
| 3 | Bovine Alpha-S1 Casein Mature protein with Methionine | MRPKHPIKHQGLPQEVLNENLLRFFVAPFPEVFGKEKVNELSKDIGSE STEDQAMEDIKQMEAESISSSEEIVPNSVEQKHIQKEDVPSERYLGYL EQLLRLKKYKVPQLEIVPNSAEERLHSMKEGIHAQQKEPMIGVNQEL AYFYPELFRQFYQLDAYPSGAWYYVPLGTQYTDAPSFSDIPNPIGSEN SEKTTMPLW |

TABLE 1-continued

Sequences

| SEQ ID No. | Name | Sequence |
|---|---|---|
| 4 | Bovine alpha S1 casein (*B. Taurus*) aa 23-199 | FFVAPFPEVFGKEKVNELSKDIGSESTEDQAMEDIKQMEAESISSSEEI VPNSVEQKHIQKEDVPSERYLGYLEQLLRLKKYKVPQLEIVPNSAEERL HSMKEGIHAQQKEPMIGVNQELAYFYPELFRQFYQLDAYPSGAWYY VPLGTQYTDAPSFSDIPNPIGSENSGKTTMPLW |
| 5 | Bovine alpha S1 casein (*B. Taurus*) aa 23-199 with Methionine | MFFVAPFPEVFGKEKVNELSKDIGSESTEDQAMEDIKQMEAESISSSE EIVPNSVEQKHIQKEDVPSERYLGYLEQLLRLKKYKVPQLEIVPNS AEERLHSMKEGIHAQQKEPMIGVNQELAYFYPELFRQFYQLDAYPSGAW YYVPLGTQYTDAPSFSDIPNPIGSENSGKTTMPLW |
| 6 | Bovine alpha S1 casein (*B. Taurus*) aa 24-199 | FVAPFPEVFGKEKVNELSKDIGSESTEDQAMEDIKQMEAESISSSEEIV PNSVEQKHIQKEDVPSERYLGYLEQLLRLKKYKVPQLEIVPNSAEERLH SMKEGIHAQQKEPMIGVNQELAYFYPELFRQFYQLDAYPSGAWYYV PLGTQYTDAPSFSDIPNPIGSENSGKTTMPLW |
| 7 | Bovine alpha S1 casein (*B. Taurus*) aa 24-199 with Methionine | MFVAPFPEVFGKEKVNELSKDIGSESTEDQAMEDIKQMEAESISSSEE IVPNSVEQKHIQKEDVPSERYLGYLEQLLRLKKYKVPQLEIVPNSAEERL HSMKEGIHAQQKEPMIGVNQELAYFYPELFRQFYQLDAYPSGAWYY VPLGTQYTDAPSFSDIPNPIGSENSGKTTMPLW |
| 8 | Bovine alpha S1 casein (*B. Taurus*) aa 25-199 | VAPFPEVFGKEKVNELSKDIGSESTEDQAMEDIKQMEAESISSSEEIVP NSVEQKHIQKEDVPSERYLGYLEQLLRLKKYKVPQLEIVPNSAEERLHS MKEGIHAQQKEPMIGVNQELAYFYPELFRQFYQLDAYPSGAWYYVP LGTQYTDAPSFSDIPNPIGSENSGKTTMPLW |
| 9 | Bovine alpha S1 casein (*B. Taurus*) aa 25-199 with Methionine | MVAPFPEVFGKEKVNELSKDIGSESTEDQAMEDIKQMEAESISSSEEI VPNSVEQKHIQKEDVPSERYLGYLEQLLRLKKYKVPQLEIVPNSAEERL HSMKEGIHAQQKEPMIGVNQELAYFYPELFRQFYQLDAYPSGAWYY VPLGTQYTDAPSFSDIPNPIGSENSGKTTMPLW |
| 10 | Bovine alpha S1 casein (*B. Taurus*) aa 26-199 | APFPEVFGKEKVNELSKDIGSESTEDQAMEDIKQMEAESISSSEEIVPN SVEQKHSQKEDVPSERYLGYLEQLLRLKKYKVPQLEIVPNSAEERLHSM KEGIHAQQKEPMIGVNQELAYFYPELFRQFYQLDAYPSGAWYYVPLG TQYTDAPSFSDIPNPIGSENSGKTTMPLW |
| 11 | Bovine alpha S1 casein (*B. Taurus*) aa 26-199 with Methionine | MAPFPEVFGKEKVNELSKDIGSESTEDQAMEDIKQMEAESISSSEEIV PNSVEQKHIQKEDVPSERYLGYLEQLLRLKKYKVPQLEIVPNSAEERLH SMKEGIHAQQKEPMIGVNQELAYFYPELFRQFYQLDAYPSGAWYYV PLGTQYTDAPSFSDIPNPIGSENSGKTTMPLW |
| 12 | Bovine alpha S1 casein (*B. Taurus*) aa 60-199 | MEAESISSSEEIVPNSVEQKHIQKEDVPSERYLGYLEQLLRLKKYKVPQL EIVPNSAEERLHSMKEGSHAQQKEPMIGVNQELAYFYPELFRQFYQL DAYPSGAWYYVPLGTQYTDAPSFSDIPNPSGSENSGKTTMPLW |
| 13 | Ovine Alpha S1 casein | MKLLILTCLVAVALARPKHPIKHQGLSSEVLNENLLRFVVAPFPEVFRK ENINELSKDIGSESIEDQAMEDAKQMKAGSSSSSEEIVPNSAEQKYIQ KEDVPSERYLGYLEQLLRLKKYNVPQLEIVPKSAEEQLHSMKEGNPAH QKQPMIAVNQELAYFYPQLFRQFYQLDAYPSGAWYYLPLGTQYTDA PSFSDIPNPIGSENSGKITMPLW |
| 14 | Ovine Alpha S1 casein Mature protein | RPKHPIKHQGLSSEVLNENLLRFVVAPFPEVFRKENINELSKDIGSESIE DQAMEDAKQMKAGSSSSSEEIVPNSAEQKYIQKEDVPSERYLGYLEQ LLRLKKYNVPQLESVPKSAEEQLHSMKEGNPAHQKQPMIAVNQELAY FYPQLFRQFYQLDAYPSGAWYYLPLGTQYTDAPSFSDIPNPIGSENSG KITMPLW |
| 15 | Ovine Alpha S1 casein Mature protein with Methionine | MRPKHPIKHQGLSSEVLNENLLRFVVAPFPEVFRKENINELSKDIGSES IEDQAMEDAKQMKAGSSSSSEEIVPNSAEQKYIQKEDVPSERYLGYLE QLLRLKKYNVPQLEIVPKSAEEQLHSMKEGNPAHQKQPMIAVNQEL AYFYPQLFRQFYQLDAYPSGAWYYLPLGTQYTDAPSFSDIPNPIGSEN SGKITMPLW |
| 16 | Ovine alpha S1 casein aa 23-199 | FVVAPFPEVFRKENINELSKDSGSESIEDQAMEDAKQMKAGSSSSSEEI VPNSAEQKYIQKEDVPSERYLGYLEQLLRLKKYNVPQLEIVPKSAEEQL HSMKEGNPAHQKQPMIAVNQELAYFYPQLFRQFYQLDAYPSGAWY YLPLGTQYTDAPSFSDIPNPIGSENSGKITMPLW |
| 17 | Ovine alpha S1 casein aa 23-199 with Methionine | MFWAPFPEVFRKENINELSKDIGSESIEDQAMEDAKQMKAGSSSSS EEIVPNSAEQKYIQKEDVPSERYLGYLEQLLRLKKYNVPQLEIVPKSAEE QLHSMKEGNPAHQKQPMIAVNQELAYFYPQLFRQFYQLDAYPSGA WYYLPLGTQYTDAPSFSDIPNPIGSENSGKITMPLW |

TABLE 1-continued

Sequences

| SEQ ID No. | Name | Sequence |
|---|---|---|
| 18 | Ovine alpha S1 casein aa 24-199 | VAPFPEVFRKENINELSKDIGSESIEDQAMEDAKQMKAGSSSSEEI VPNSAEQKYIQKEDVPSERYLGYLEQLLRLKKYNVPQLEIVPKSAEEQL HSMKEGNPAHQKQPMIAVNQELAYFYPQLFRQFYQLDAYPSGAWY YLPLGTQYTDAPSFSDIPNPIGSENSGKITMPLW |
| 19 | Ovine alpha S1 casein aa 24-199 with Methionine | MVVAPFPEVFRKENINELSKDIGSESIEDQAMEDAKQMKAGSSSSE EIVPNSAEQKYIQKEDVPSERYLGYLEQLLRLKKYNVPQLEIVPKSAEE QLHSMKEGNPAHQKQPMIAVNQELAYFYPQLFRQFYQLDAYPSGA WYYLPLGTQYTDAPSFSDIPNPIGSENSGKITMPLW |
| 20 | Ovine alpha S1 casein aa 25-199 | VAPFPEVFRKENINELSKDIGSESIEDQAMEDAKQMKAGSSSSEEIV PNSAEQKYIQKEDVPSERYLGYLEQLLRLKKYNVPQLEIVPKSAEEQLH SMKEGNPAHQKQPMIAVNQELAYFYPQLFRQFYQLDAYPSGAWYY LPLGTQYTDAPSFSDIPNPIGSENSGKITMPLW |
| 21 | Ovine alpha S1 casein aa 25-199 with Methionine | MVAPFPEVFRKENINELSKDIGSESIEDQAMEDAKQMKAGSSSSEEL VPNSAEQKYIQKEDVPSERYLGYLEQLLRLKKYNVPQLEIVPKSAEEQL HSMKEGNPAHQKQPMIAVNQELAYFYPQLFRQFYQLDAYPSGAWY YLPLGTQYTDAPSFSDIPNPIGSENSGKITMPLW |
| 22 | Ovine alpha S1 casein aa 26-199 | APFPEVFRKENINELSKDIGSESIEDQAMEDAKQMKAGSSSSEEIVP NSAEQKYIQKEDVPSERYLGYLEQLLRLKKYNVPQLEIVPKSAEEQLHS MKEGNPAHQKQPMIAVNQELAYFYPQLFRQFYQLDAYPSGAWYYL PLGTQYTDAPSFSDIPNPIGSENSGKITMPLW |
| 23 | Ovine alpha S1 casein aa 26-199 with Methionine | MAPFPEVFRKENINELSKDIGSESIEDQAMEDAKQMKAGSSSSEEIV PNSAEQKYIQKEDVPSERYLGYLEQLLRLKKYNVPQLEIVPKSAEEQLH SMKEGNPAHQKQPMIAVNQELAYFYPQLFRQFYQLDAYPSGAWYY LPLGTQYTDAPSFSDIPNPIGSENSGKITMPLW |
| 24 | Ovine alpha S1 casein aa 60-199 | MKAGSSSSEEIVPNSAEQKYIQKEDVPSERYLGYLEQLLRLKKYNVPQ LEIVPKSAEEQLHSMKEGNPAHQKQPMIAVNQELAYFYPQLFRQFY QLDAYPSGAWYYLPLGTQYTDAPSFSDIPNPIGSENSGKITMPLW |
| 25 | Caprine Alpha S1 casein | MKLLILTCLVAVALARPKHPINHRGLSPEVPNENLLRFVVAPFPEVFR KENINELSKDIGSESTEDQAMEDAKQMKAGSSSSEEIVPNSAEQKYI QKEDVPSERYLGYLEQLLRLKKYNVPQLEIVPKSAEEQLHSMKEGNPA HQKQPMSAVNQELAYFYPQLFRQFYQLDAYPSGAWYYLPLGTQYTD APSFSDIPNPIGSENSGKTTMPLW |
| 26 | Caprine Alpha S1 casein Mature Protein | RPKHPSNHRGLSPEVPNENLLRFVVAPFPEVFRKENINELSKDIGSEST EDQAMEDAKQMKAGSSSSEEIVPNSAEQKYIQKEDVPSERYLGYLE QLLRLKKYNVPQLEIVPKSAEEQLHSMKEGNPAHQKQPMIAVNQEL AYFYPQLFRQFYQLDAYPSGAWYYLPLGTQYTDAPSFSDIPNPIGSEN SGKTTMPLW |
| 27 | Caprine Alpha S1 casein Mature Protein with Methionine | MRPKHPINHRGLSPEVPNENLLRFVVAPFPEVFRKENINELSKDIGSES TEDQAMEDAKQMKAGSSSSEEIVPNSAEQKYIQKEDVPSERYLGYL EQLLRLKKYNVPQLEIVPKSAEEQLHSMKEGNPAHQKQPMIAVNQE LAYFYPQLFRQFYQLDAYPSGAWYYLPLGTQYTDAPSFSDIPNPIGSE NSGKTTMPLW |
| 28 | Buffalo Alpha S1 Casein | MKLLILTCLVAVALARPKQPIKHQGLPQGVLNENLLRFFVAPFPEVFG KEKVNELSTDIGSESTEDQAMEDIKQMEAESISSSEEIVPISVEQKHIQ KEDVPSERYLGYLEQLLRLKKYNVPQLEIVPNLAEEQLHSMKEGIHAQ QKEPMIGVNQELAYFYPQLFRQFYQLDAYPSGAWYYVPLGTQYPDA PSFSDIPNPIGSENSEKTTMPLW |
| 29 | Buffalo Alpha S1 Casein Mature Protein | RPKQPIKHQGLPQGVLNENLLRFFVAPFPEVFGKEKVNELSTDIGSEST EDQAMEDIKQMEAESISSSEEIVPISVEQKHIQKEDVPSERYLGYLEQL LRLKKYNVPQLEIVPNLAEEQLHSMKEGIHAQQKEPMIGVNQELAYF YPQLFRQFYQLDAYPSGAWYYVPLGTQYPDAPSFSDIPNPIGSENSEK TTMPLW |
| 30 | Buffalo Alpha S1 Casein Mature Protein with Methionine | MRPKQPIKHQGLPQGVLNENLLRFFVAPFPEVFGKEKVNELSTDIGSE STEDQAMEDIKQMEAESISSSEEIVPISVEQKHIQKEDVPSERYLGYLE QLLRLKKYNVPQLEIVPNLAEEQLHSMKEGIHAQQKEPMIGVNQELA YFYPQLFRQFYQLDAYPSGAWYYVPLGTQYPDAPSFSDIPNPIGSENS EKTTMPLW |
| 31 | Equine Alpha S1 Casein | MKLLILTCLVAVALARPKLPHRQPEIIQNEQDSREKVLKERKFPSFALE YINELNRQRELLKEKQKDEHKEYLIEDPEQQESSTSSSEEVVPINTEQK RIPREDMLYQHTLEQLRRLSKYNQLQLQAIHAQEQLIRMKENSQRKP MRVVNQEQAYFYLEPFQPSYQLDVYPYAAWFHPAQIMQHVAYSPF HDTAKLIASENSEKTDIIPEW |

TABLE 1-continued

Sequences

| SEQ ID No. | Name | Sequence |
|---|---|---|
| 32 | Equine Alpha S1 Casein Mature Protein | RPKLPHRQPEIIQNEQDSREKVLKERKFPSFALEYINELNRQRELLKEK QKDEHKEYLIEDPEQQESSSTSSSEEVVPINTEQKRIPREDMLYQHTLE QLRRLSKYNQLQLQAIHAQEQLIRMKENSQRKPMRVVNQEQAYFYL EPFQPSYQLDVYPYAAWFHPAQIMQHVAYSPFHDTAKUASENSEKT DIIPEW |
| 33 | Equine Alpha S1 Casein Mature Protein with Methionine | MRPKLPHRQPEIIQNEQDSREKVLKERKFPSFALEYINELNRQRELLKE KQKDEHKEYLIEDPEQQESSSTSSSEEVVPINTEQKRIPREDMLYQHTL EQLRRLSKYNQLQLQAIHAQEQLIRMKENSQRKPMRVVNQEQAYFY LEPFQPSYQLDVYPYAAWFHPAQSMQHVAYSPFHDTAKLSASENSEK TDIIPEW |
| 34 | Camel Alpha S1 casein | MKLLILTCLVAVALARPKYPLRYPEVFQNEPDSIEEVLNKRKILELAVVS PIQFRQENIDELKDTRNEPTEDHIMEDTERKESGSSSSEEVVSSTTEQK DILKEDMPSQRYLEELHRLNKYKLLQLEAIRDQKLIPRVKLSSHPYLEQL YRINEDNHPQLGEPVKVVTQEQAYFHLEPFPQFFQLGASPYVAWYYP PQVMQYIAHPSSYDTPEGIASEDGGKTDVMPQWW |
| 35 | Camel Alpha S1 casein Mature Protein | RPKYPLRYPEVFQNEPDSSEEVLNKRKILELAVVSPSQFRQENIDELKDT RNEPTEDHIMEDTERKESGSSSSEEVVSSTTEQKDILKEDMPSQRYLE ELHRLNKYKLLQLEAIRDQKLIPRVKLSSHPYLEQLYRINEDNHPQLGE PVKVVTQEQAYFHLEPFPQFFQLGASPYVAWYYPPQVMQYIAHPSS YDTPEGIASEDGGKTDVMPQWW |
| 36 | Camel Alpha S1 casein Mature Protein with Methionine | MRPKYPLRYPEVFQNEPDSIEEVLNKRKILELAVVSPIQFRQENIDELK DTRNEPTEDHIMEDTERKESGSSSSEEVVSSTTEQKDILKEDMPSQRY LEELHRLNKYKLLQLEAIRDQKLIPRVKLSSHPYLEQLYRINEDNHPQLG EPVKVVTQEQAYFHLEPFPQFFQLGASPYVAWYYPPQVMQYIAHPS SYDTPEGIASEDGGKTDVMPQWW |
| 37 | Human Alpha S1 Casein | MRLLILTCLVAVALARPKLPLRYPERLQNPSESSEPIPLESREEYMNG MNRQRNILREKQTDEIKDTRNESTQNCVVAEPEKMESSISSSSEEMSL SKCAEQFCRLNEYNQLQLQAAHAQEQIRRMNENSHVQVPFQQLNQ LAAYPYAVWYYPQIMQYVPFPPPFSDISNPTAHENYEKNNVMLQW |
| 38 | Human Alpha S1 Casein Mature Protein | RPKLPLRYPERLQNPSESSEPIPLESREEYMNGMNRQRNILREKQTDE IKDTRNESTQNCVVAEPEKMESSISSSSEEMSLSKCAEQFCRLNEYNQ LQLQAAHAQEQIRRMNENSHVQVPFQQLNQLAAYPYAVWYYPQI MQYVPFPPPFSDISNPTAHENYEKNNVMLQW |
| 39 | Bovine Alpha-S2 Casein | MKFFIFTCLLAVALAKNTMEHVSSSEESIISQETYKQEKNMAINPSKE NLCSTFCKEVVRNANEEEYSIGSSSEESAEVATEEVKITVDDKHYQKAL NEINQFYQKFPQYLQYLYQGPIVLNPWDQVKRNAVPITPTLNREQLS TSEENSKKTVDMESTEVFTKKTKLTEEEKNRLNFLKKISQRYQKFALPQ YLKTVYQHQKAMKPWIQPKTKVIPYVRYL |
| 40 | Bovine Alpha-S2 Casein Mature protein | KNTMEHVSSSEESIISQETYKQEKNMAINPSKENLCSTFCKEVVRNAN EEEYSIGSSSEESAEVATEEVKITVDDKHYQKALNEINQFYQKFPQYLQ YLYQGPIVLNPWDQVKRNAVPITPTLNREQLSTSEENSKKTVDMEST EVFTKKTKLTEEEKNRLNFLKKISQRYQKFALPQYLKTVYQHQKAMKP WIQPKTKVIPYVRYL |
| 41 | Bovine Alpha-S2 Casein Mature protein with Methionine | MKNTMEHVSSSEESIISQETYKQEKNMAINPSKENLCSTFCKEVVRN ANEEEYSIGSSSEESAEVATEEVKITVDDKHYQKALNEINQFYQKFPQY LQYLYQGPIVLNPWDQVKRNAVPITPTLNREQLSTSEENSKKTVDME STEVFTKKTKLTEEEKNRLNFLKKISQRYQKFALPQYLKTVYQHQKAM KPWIQPKTKVIPYVRYL |
| 42 | Ovine Alpha S2 casein | MKFFIFTCLLAVALAKHKMEHVSSSEEPINISQEIYKQEKNMAIHPRK EKLCTTSCEEVVRNADEEEYSIRSSSEESAEVAPEEVKITVDDKHYQKA LNEINQFYQKFPQYLQYLYQGPIVLNPWDQVKRNAGPFTPTVNREQ LSTSEENSKKTIDMESTEVFTKKTKLTEEEKNRLNFLKKISQYYQKFAW PQYLKTVDQHQKAMKPWTQPKTNAIPYVRYL |
| 43 | Ovine Alpha S2 casein Mature protein | KHKMEHVSSSEEPINISQEIYKQEKNMAIHPRKEKLCTTSCEEVVRNA DEEEYSIRSSSEESAEVAPEEVKITVDDKHYQKALNEINQFYQKFPQYL QYLYQGPIVLNPWDQVKRNAGPFTPTVNREQLSTSEENSKKTIDMES TEVFTKKTKLTEEEKNRLNFLKKISQYYQKFAWPQYLKTVDQHQKAM KPWTQPKTNAIPYVRYL |
| 44 | Ovine Alpha S2 casein Mature protein with Methionine | MKHKMEHVSSSEEPINISQEIYKQEKNMAIHPRKEKLCTTSCEEVVRN ADEEEYSIRSSSEESAEVAPEEVKITVDDKHYQKALNEINQFYQKFPQY LQYLYQGPIVLNPWDQVKRNAGPFTPTVNREQLSTSEENSKKTIDME STEVFTKKTKLTEEEKNRLNFLKKSSQYYQKFAWPQYLKTVDQHQKA MKPWTQPKTNAIPYVRYL |

TABLE 1-continued

Sequences

| SEQ ID No. | Name | Sequence |
|---|---|---|
| 45 | Caprine Alpha S2 casein | MKFFSFTCLLAVALAKHKMEHVSSSEEPINIFQEIYKQEKNMAIHPRK EKLCTTSCEEVVRNANEEEYSIRSSSEESAEVAPEESKITVDDKHYQKAL NEINQFYQKFPQYLQYPYQGPIVLNPWDQVKRNAGPFTPTVNREQL STSEENSKKTIDMESTEVFTKKTKLTEEEKNRLNFLKKISQYYQKFAWP QYLKTVDQHQKAMKPWTQPKTNAIPYVRYL |
| 46 | Caprine Alpha S2 casein Mature Protein | KHKMEHVSSSEEPINIFQEIYKQEKNMAIHPRKEKLCTTSCEEVVRNA NEEEYSIRSSSEESAEVAPEEIKITVDDKHYQKALNEINQFYQKFPQYL QYPYQGPIVLNPWDQVKRNAGPFTPTVNREQLSTSEENSKKTIDMES TEVFTKKTKLTEEEKNRLNFLKKISQYYQKFAWPQYLKTVDQHQKAM KPWTQPKTNAIPYVRYI |
| 47 | Caprine Alpha S2 casein Mature Protein with Methionine | MKHKMEHVSSSEEPINIFQEIYKQEKNMAIHPRKEKLCTTSCEEVVRN ANEEEYSIRSSSEESAEVAPEEIKITVDDKHYQKALNEINQFYQKFPQYL QYPYQGPIVLNPWDQVKRNAGPFTPTVNREQLSTSEENSKKTIDMES TEVFTKKTKLTEEEKNRLNFLKKISQYYQKFAWPQYLKTVDQHQKAM KPWTQPKTNAIPYVRYL |
| 48 | Buffalo Alpha S2 Casein | MKFFIFTCLLAVALAKHTMEHVSSSEESHSQETYKQEKNMAIHPSKE NLCSTFCKEVIRNANEEEYSIGSSSEESAEVATEEVKITVDDKHYQKAL NEINQFYQKFPQYLQYLYQGPIVLNPWDQVKRNAVPITPTLNREQLS TSEENSKKTVDMESTEVFTKKTKLTEEDKNRLNFLKKISQHYQKFAWP QYLKTVYQYQKAMKPWTQPKTNVIPYVRYL |
| 49 | Buffalo Alpha S2 Casein Mature Protein | KHTMEHVSSSEESIISQETYKQEKNMAIHPSKENLCSTFCKEVIRNANE EEYSIGSSSEESAEVATEEVKITVDDKHYQKALNEINQFYQKFPQYLQY LYQGPIVLNPWDQVKRNAVPITPTLNREQLSTSEENSKKTVDMESTE VFTKKTKLTEEDKNRLNFLKKISQHYQKFAWPQYLKTVYQYQKAMKP WTQPKTNVIPYVRYL |
| 50 | Buffalo Alpha S2 Casein Mature Protein with Methionine | MKHTMEHVSSSEESIISQETYKQEKNMAIHPSKENLCSTFCKEVIRNA NEEEYSIGSSSEESAEVATEEVKITVDDKHYQKALNEINQFYQKFPQYL QYLYQGPIVLNPWDQVKRNAVPITPTLNREQLSTSEENSKKTVDMES TEVFTKKTKLTEEDKNRLNFLKKISQHYQKFAWPQYLKTVYQYQKAM KPWTQPKTNVIPYVRYL |
| 51 | Equine Aipha S2 Casein | MKFFIFTCLLAVALAKHNMEHRSSSEDSVNISQEKFKQEKYVVIPTSK ESICSTSCEEATRNINEMESAKFPTEREEKEVEEKHHLKQLNKINQFYE KLNFLQYLQALRQPRIVLTPWDQTKTGDSPFIPIVNTEQLFTSEEIPKK TVDMESTEVVTEKTELTEEEKNYLKLLYYEKFTLPQYFKIVRQHQTTM DPRSHRKTNSYQIIPVLRYF |
| 52 | Equine Alpha S2 Casein Mature Protein | KHNMEHRSSSEDSVNISQEKFKQEKYVVIPTSKESICSTSCEEATRNIN EMESAKFPTEREEKEVEEKHHLKQLNKINQFYEKLNFLQYLQALRQPR IVLTPWDQTKTGDSPFIPIVNTEQLFTSEEIPKKTVDMESTEVVTEKTE LTEEEKNYLKLLYYEKFTLPQYFKIVRQHQTTMDPRSHRKTNSYQIIPV LRYF |
| 53 | Equine Alpha S2 Casein Mature Protein with Methionine | MKHNMEHRSSSEDSVNISQEKFKQEKYVVIPTSKESICSTSCEEATRNI NEMESAKFPTEREEKEVEEKHHLKQLNKINQFYEKLNFLQYLQALRQP RIVLTPWDQTKTGDSPFIPIVNTEQLFTSEEIPKKTVDMESTEVVTEKT ELTEEEKNYLKLLYYEKFTLPQYFKIVRQHQTTMDPRSHRKTNSYQIIP VLRYF |
| 54 | Camel Alpha S2 casein | MKFFIFTCLLAVVLAKHEMDQGSSSEESINVSQQKFKQVKKVAIHPSK EDICSTFCEEAVRNIKEVESAEVPTENKISQFYQKWKFLQYLQALHQG QIVMNPWDQGKTRAYPFIPTVNTEQLSISEESTEVPTEESTEVFTKKTE LTEEEKDHQKFLNKIYQYYQTFLWPEYLKTVYQYQKTMTPWNHIKRY F |
| 55 | Camel Alpha S2 casein Mature Protein | KHEMDQGSSSEESINVSQQKFKQVKKVAIHPSKEDICSTFCEEAVRNI KEVESAEVPTENKISQFYQKWKFLQYLQALHQGQIVMNPWDQGKT RAYPFIPTVNTEQLSISEESTEVPTEESTEVFTKKTELTEEEKDHQKFLN KIYQYYQTFLWPEYLKTVYQYQKTMTPWNHIKRYF |
| 56 | Camel Alpha S2 casein Mature Protein with Methionine | MKHEMDQGSSSEESINVSQQKFKQVKKVAIHPSKEDICSTFCEEAVR NIKEVESAEVPTENKISQFYQKWKFLQYLQALHQGQIVMNPWDQGK TRAYPFIPTVNTEQLSISEESTEVPTEESTEVFTKKTELTEEEKDHQKFL NKIYQYYQTFLWPEYLKTVYQYQKTMTPWNHIKRYF |

Embodiments

[Embodiment 1]: A consumable composition comprising a recombinant single variant of an alpha casein protein, wherein the single variant provides at least one dairy-like property selected from the group consisting of adhesiveness, stretch, texture, mouthfeel, melt, browning hardness, creaminess, taste, smell, and flexibility, wherein the single variant is not an animal-derived casein and has not been physically dissociated from a casein micelle and wherein the composition lacks any additional caseins.

[Embodiment 2]: The consumable composition of embodiment 1, wherein the single variant of the alpha casein protein is not derived from caseinate.

[Embodiment 3]: The consumable composition of embodiment 1 or embodiment 2, wherein the single variant of the alpha casein protein is an alpha-s1 casein protein.

[Embodiment 4]: The consumable composition of embodiment 1 or embodiment 2, wherein the single variant of the alpha casein protein is an alpha-s2 casein protein.

[Embodiment 5]: The consumable composition of any of embodiments 1-3, wherein the composition is free from any animal-produced proteins.

[Embodiment 6]: The consumable composition of embodiment 4, wherein the composition lacks any other animal-derived dairy proteins.

[Embodiment 7]: The consumable composition of any of embodiments 1-5, wherein at least one dairy-like property is improved as compared to a milk-derived cheese analogue.

[Embodiment 8]: The consumable composition of any of embodiments 1-5, wherein at least one dairy-like property is improved as compared to a caseinate-derived cheese analogue or improved as compared to a rennet casein-derived cheese analogue.

[Embodiment 9]: The consumable composition of any of embodiments 1-5, wherein at least one dairy-like property is improved as a compared to a plant-derived cheese analogue.

[Embodiment 10]: The consumable composition of any of embodiments 1-9, wherein the single variant of the alpha casein protein comprises at least one non-native post-translational modification.

[Embodiment 11]: The consumable composition of embodiment 10, wherein the single variant of the alpha casein protein further comprises at least one native post-translational modification.

[Embodiment 12]: The consumable composition of any of embodiments 1-11, wherein the single variant of the alpha casein protein lacks one or more post-translational modifications of a native alpha casein protein.

[Embodiment 13]: The consumable composition of embodiment 12, wherein the single variant of the alpha casein protein further comprises at least one non-native post-translational modification.

[Embodiment 14]: The consumable composition of embodiment 13, wherein the single variant of the alpha casein protein is not post-translational modified.

[Embodiment 15]: The consumable composition of any of embodiments 1-14, wherein the composition comprises a full-length alpha casein protein.

[Embodiment 16]: The consumable composition of any of embodiments 1-14, wherein the single variant of the alpha casein protein comprises any one of SEQ ID Nos. 2, 3, 14, 15, 26, 27, 29, 30, 32, 33, 35, 36, 38, 40, 41, 43, 44, 46, 47, 49, 50, 52, 53, 55 or 56.

[Embodiment 17]: The consumable composition of embodiment 16, wherein composition further comprises one or more truncated alpha casein proteins.

[Embodiment 18]: The consumable composition of embodiment 17, wherein the truncated alpha casein protein lacks 1 or more N-terminal amino acids of a mature native alpha casein protein.

[Embodiment 19]: The consumable composition of embodiment 18, wherein the truncated alpha casein protein is selected from the group consisting of an alpha casein lacking between 1-23 N-terminal amino acids of the native alpha casein protein or an alpha casein lacking between 1-59 N-terminal amino acids of the native alpha casein protein or a combination thereof.

[Embodiment 20]: The consumable composition of embodiment 19, wherein the truncated alpha casein protein comprises any one of SEQ ID NOs.: 4-12, 16-24.

[Embodiment 21]: The consumable composition of any of embodiments 17-20, wherein the truncated alpha casein protein lacks 1 or more C-terminal amino acids of a native alpha casein protein.

[Embodiment 22]: The consumable composition of embodiment 17, wherein between 0% and 20% wt/wt of the total recombinant alpha casein protein of the composition is the one or more truncated forms of the alpha casein protein.

[Embodiment 23]: The consumable composition of embodiment 22, wherein the one or more truncated forms of the alpha casein protein comprise between 1% and 20% wt/wt of the total recombinant alpha casein protein of the composition.

[Embodiment 24]: The consumable composition of any of embodiments 1-23, wherein the recombinant alpha casein protein comprises an amino acid sequence of a bovine, caprine or ovine alpha casein protein or any one of SEQ ID NOs.: 2, 3, 14, 15, 26, 27, 29, 30, 32, 33, 35, 36, 38, 40, 41, 43, 44, 46, 47, 49, 50, 52, 53, 55 or 56 or a sequence with at least 70%, 80%, 85% or 90% identity to any one of SEQ ID NOs.: 2, 3, 14, 15, 26, 27, 29, 30, 32, 33, 35, 36, 38, 40, 41, 43, 44, 46, 47, 49, 50, 52, 53, 55 or 56.

[Embodiment 25]: The consumable composition of any of embodiments 1-24, wherein the single variant of an alpha casein protein comprises one or more non-native amino acids at the N-terminus.

[Embodiment 26]: The consumable composition of embodiment 25, wherein the single variant of an alpha casein protein comprises a non-native methionine at the N-terminal position.

[Embodiment 27]: The consumable composition of any of embodiments 1-26, wherein the single variant of an alpha casein protein is not derived from casein micelles.

[Embodiment 28]: A dairy product analogue comprising any of the consumable compositions of embodiments 1-27, wherein the analogue is selected from the group consisting of a cheese analogue, a yogurt analogue, a cream analogue, and an ice cream analogue.

[Embodiment 29]: The dairy product analogue of embodiment 28, further comprising a fat or oil from a non-animal source.

[Embodiment 30]: The dairy product analogue of embodiment 28 or embodiment 29, wherein the dairy product analogue lacks any animal-derived dairy proteins.

[Embodiment 31]: The dairy product analogue of any of embodiments 28-30, wherein the dairy product analogue lacks any other casein proteins.

[Embodiment 32]: The dairy product analogue of any of embodiments 28-31, wherein the single variant of an alpha casein protein is not comprised in a micellar form within the dairy product analogue.

[Embodiment 33]: The dairy product analogue of any of embodiments 28-32, wherein the dairy product analogue is a cheese analogue.

[Embodiment 34]: The dairy product analogue of embodiment 33, wherein the cheese analogue is a mozzarella analogue, a cheddar analogue or a parmesan analogue.

[Embodiment 35]: The dairy product analogue of embodiment 33, wherein the cheese analogue is a mozzarella analogue and wherein the single variant of an alpha casein protein is an alpha S1 casein.

[Embodiment 36]: The dairy product analogue of embodiment 35, wherein the alpha S1 casein is a bovine alpha S1 casein, and wherein the alpha S1 casein in the composition comprises between 0-20% of one or more truncated forms of alpha casein.

[Embodiment 37]: The dairy product analogue of embodiment 35, wherein the alpha S1 casein in the composition comprises between 1-20% of one or more truncated forms of alpha S1 casein.

[Embodiment 38]: The dairy product analogue of embodiment 36, or embodiment 37, comprising a N-terminal truncated form of alpha S1 casein.

[Embodiment 39]: The dairy product analogue of embodiment 38, wherein the N-terminal truncated form is selected from any one of SEQ ID NOs: 4-12, 16-24 or a combination thereof.

[Embodiment 40]: The dairy product analogue according to any of embodiments 28-39, further comprising one or more of (a) a plant-derived oil; (b) a plant-derived starch; (c) a sugar; and (d) a salt.

EXAMPLES

The following illustrative examples are representative of embodiments of the compositions and methods described herein and are not meant to be limiting in any way.

Example 1: Expression of Casein Proteins in *Lactococcus lactis* Via Nisin-Inducible System (NICE)

Constructs Design, Cloning and Transformation

Bovine alpha S1 casein (variant C) protein coding sequence (without the native signal peptide) was codon-optimized for expression in *Lactococcus lactis* and a synthetic operon was constructed for co-expression and secretion of the two proteins under a nisin-inducible promoter. Signal peptide sequence from natively secreting lactococcal protein Usp45 was used to drive protein secretion. A synthetic operon was then cloned into an *E. coli* custom vector via restriction digest compatible sites and confirmed via Sanger sequencing, from which it was subcloned into nisin-inducible pNZ8149 vector via restriction digestion and ligation.

The vector was transformed into compatible *L. lactis* strain NZ3900 via electroporation and completely defined media (CDM) supplemented with lactose was used for selection. Positive clones were confirmed via colony PCR and 3 positive clones were taken forward for the protein expression induction and analysis.

Protein Expression and Analysis

Individual colonies were grown at 30° C. in liquid culture and protein production was induced with nisin for 2.5 hours (control samples left uninduced). Cells were then harvested by centrifugation and TCA-precipitated supernatants and lysed cell pellets were analysed by Coomassie gel staining (SDS-PAGE) and chemiluminescence (Western Blot against alpha S1 casein, LSBio primary antibodies).

Example 2: Expression in *L. lactis* Via pH-Inducible System

Similar to the constructions above, alpha casein protein constructions were created replacing the nisin promoter with the P170 promoter, a pH/lactate inducible promoter for *L. lactis*. Each of these constructs contained a secretion signal peptide.

Alpha S1 casein and its truncated forms were detected in *L. lactis* upon secretion on western blot. Unprocessed protein product accumulated intracellularly but secretion was detected for the mature protein and its truncated forms.

Example 3: Expression in *B. subtilis*

Constructs Design, Cloning and Transformation

Bovine alpha S1 casein (variant C) protein coding sequence (without the native signal peptide) His-tagged C-terminally was codon-optimized for expression in *Bacillus subtilis*. Constructs were created with and without the codon-optimized signal peptide of amyQ, alpha-amylase *Bacillus amyloliquefaciens* which has been reported for the efficient secretion of recombinant proteins. Constructs were cloned through *E. coli* via Gibson cloning into transformation and expression IPTG-inducible vector pHT01 and confirmed via Sanger sequencing. pHT01 is an *E. coli/B. subtilis* shuttle vector that provides ampicillin resistance to *E. coli* and chloramphenicol resistance to *B. subtilis*. Positive clones were further transformed into chemically competent *B. subtilis* WB800N. Positive clones were confirmed via colony PCR and 3 positive clones were taken forward for the protein expression induction and analysis.

Protein Expression and Analysis

Individual colonies were grown at 37° C. in liquid culture and protein production was induced with IPTG for 1 hour, 2 hours and 6 hours (control samples were left uninduced). Cells were then harvested by centrifugation, and TCA-precipitated supernatants and lysed cell pellets were analysed by Coomassie gel staining (SDS-PAGE) and chemiluminescence (Western Blot against His tag and alpha S1 casein).

Western blotting showed expression of the alpha S1 casein in *B. subtilis*.

Example 4: Expression in *E. coli*

Constructs Design, Cloning and Transformation

Bovine alpha S1 casein (variant C) protein coding sequence (without the native signal peptide) codon-optimized for *Escherichia coli* was cloned into IPTG-inducible commercially available pET vectors. Cloning was performed via Gibson reaction of DNA fragments and vector in such a way that only the protein coding sequence was left within the open reading frame. Gibson reactions were transformed into competent cells and confirmed by Sanger sequencing. Vectors were then transformed into chemically competent *E. coli* BL21(DE3) cells or their derivatives, or a wild-type like K12 strain or their derivatives, and several single colonies were screened for expression.

Protein Expression, Analysis And Purification

Individual colonies were grown at 37 C in liquid culture, and protein production was induced with IPTG for 4 hours. Cells were then harvested by centrifugation, and lysed cell pellets were analysed by Coomassie gel staining (SDS- PAGE) and chemiluminescence (Western Blot against alpha S1 casein). Proteins were purified using phase separation. Purified product was analysed on a Coomassie stained gel similarly to explained above. Alpha S1 casein was expressed intracellularly in *E. coli*, successfully detected on Coomassie stained protein gel and purified. An exemplary production of alpha casein is illustrated in FIG. 1 where the alpha S1 casein and 2 variants: N-terminally truncated F24-199 bovine alpha S1 casein and N-terminally truncated M60-199 bovine alpha S1 casein were also found.

Example 5: Mozzarella Cheese Analogue from Recombinant Single Variant Alpha Casein Protein and its Properties Recombinant unphosphorylated alpha S1 casein (and truncated forms of the alpha S1 casein, as shown in FIG. 1), was used to make non-micellar mozzarella cheese analogue termed NC mozzarella cheese. Casein, prewarmed coconut oil, trisodium citrate, disodium phosphate, salt and glucose were added in a beaker at concentrations specified in Table 2. To this, a mix of water, $CaCl_2$, and modified potato starch were added at concentration specified in Table 2. The beaker was moved to a water bath preset at 85° C. temperature and the contents were mixed using a mixing propeller at a speed of 300 rpm for 9 mins. Lactic acid was added and mixed for an additional 1 min. The resulting mixture turned to a homogeneous non-micellar mass, transferred to standard molds, and allowed to sit in the fridge for 16-24 hrs. After incubation, the NC mozzarella cheese analogue was weighed to get yield estimation.

TABLE 2

Ingredient Composition and Concentration for Recombinant Single Casein Variant Cheese Analogue (NC1 mozzarella cheese analogue)

| Ingredients | Concentration (%, wt/wt) |
| --- | --- |
| Casein | 18.5 |
| Coconut oil | 25.26 |
| Trisodium Citrate | 0.7 |
| Disodium phosphate | 1.29 |
| Sodium chloride | 1.49 |
| Glucose | 0.4 |
| Water | 48.32 |
| CaCl2 | 1 |
| Modified potato starch | 2.54 |
| Lactic acid crystals | 0.5 |

The NC1 mozzarella cheese analogue samples were analyzed for qualitative and quantitative parameters such as pH, stretch, and texture profile. These parameters were compared to commercially available low-moisture mozzarella cheese, commercially available imitation mozzarella cheese and a commercially available plant-based vegan mozzarella-style cheese. The low-moisture mozzarella cheese is made from milk, where the caseins are micellar and come in their natural high complexity of variants (alpha-S1, alpha-S2, beta, kappa; phosphorylated and glycosylated). The imitation mozzarella cheese is made from milk casein blend with plant-based fats, where micellar caseins from milk are renneted and dried into a milk protein concentrate. The plant-based vegan mozzarella-style cheese has no casein proteins.

A pizza fork stretch test was performed to quantitate cheese extensibility by inserting a fork into the center of freshly baked pizza and lifted until all the cheese strands broke. For this, 6 g of cheese was shredded on a 4" inch tortilla topped with 4 g of tomato sauce. Samples were baked at 600° F. for 90 seconds. A ruler was used to measure the stretch and the test was performed immediately after removing the pizza from the oven.

The texture profile was analyzed on TA-XT plus texture analyzer with TA-55 puncture probe. 1.5-1.9 g of cheese sample was cut in 1.5 cm 1×1.5 cm w×1 cm h dimension. The tests were performed on samples stored at 4° C. and at ambient temperatures at least for 30 mins.

The NC1 mozzarella cheese analogue, made from recombinant unphosphorylated alpha S1 casein and its truncated forms as the only protein ingredient in the cheese, showed animal-derived dairy-like melt, dairy-like stretch and dairy-like texture properties in the tests performed. The pH of set cheese was 5.9.

Figure 2:
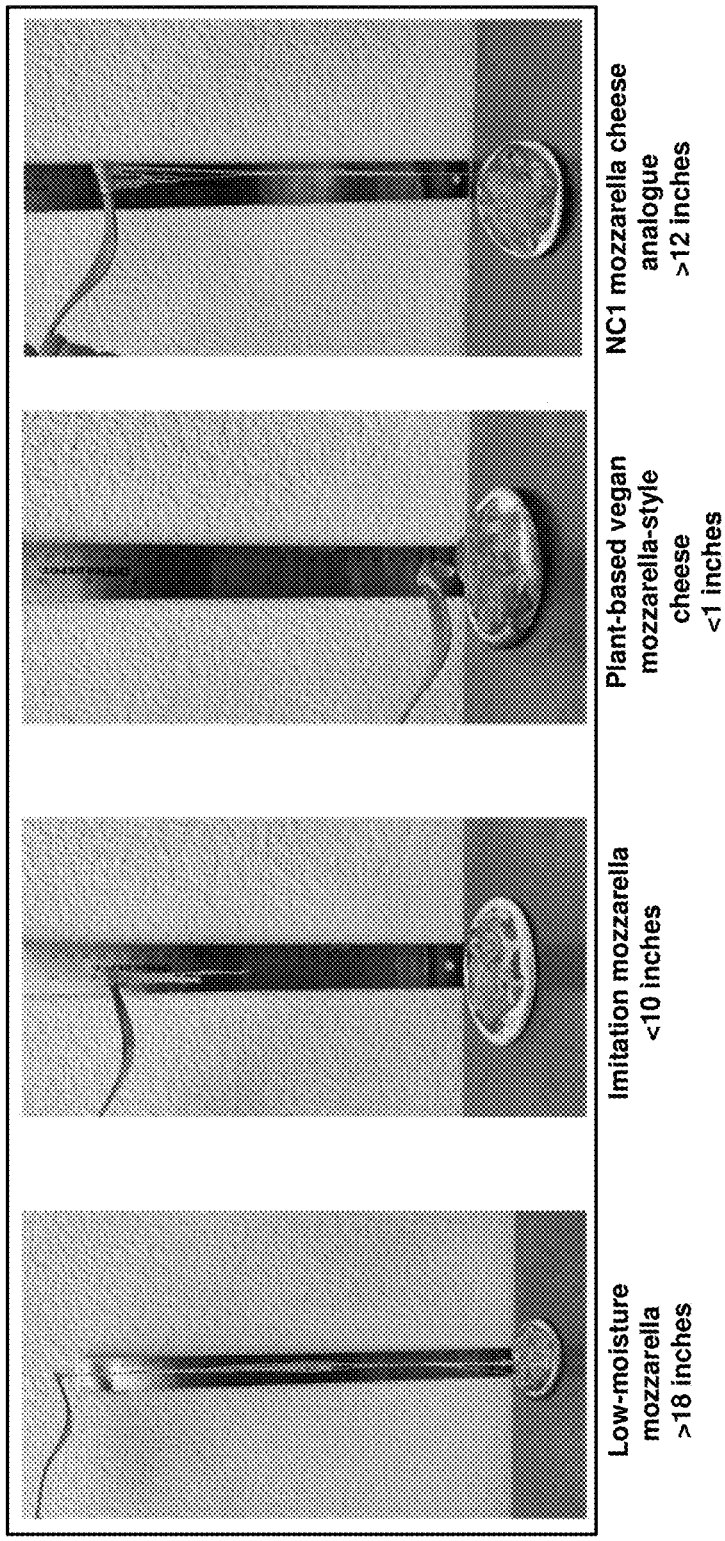
FIG. 2 illustrates a comparison of stretching ability (extensibility) between the analogue cheese made using the methods described herein and a few commercially available cheeses and cheese analogues.

The pizza fork stretch test showed that NC1 mozzarella cheese analogue stretched >12 inches (Table 3, FIG. 2). In comparison, the low-moisture mozzarella stretched >18 inches but the imitation mozzarella stretched only <10 inches. The plant-based vegan mozzarella-style cheese didn't show stretch, it stretched <1 inch.

Figure 3:
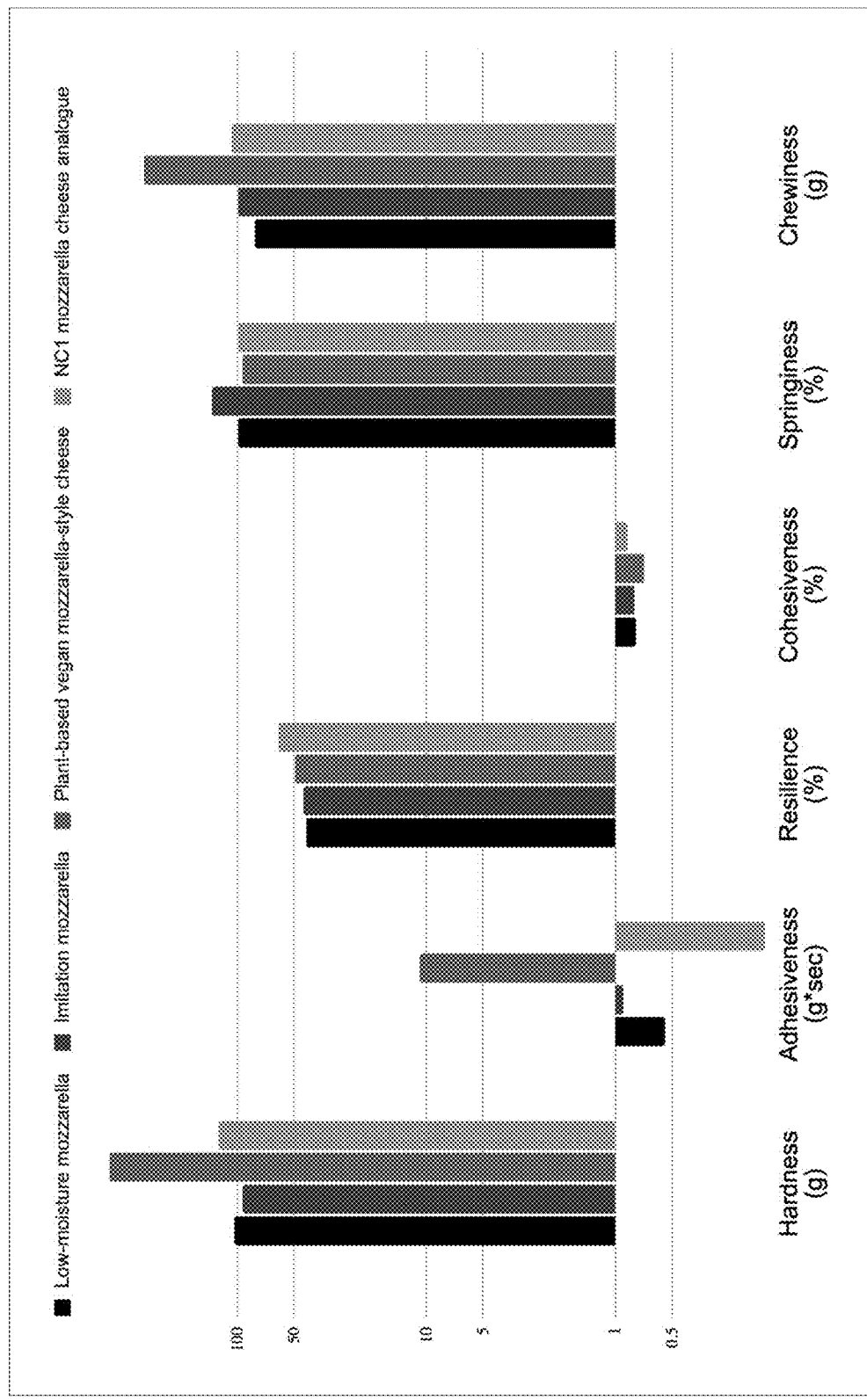
FIG. 3 illustrates a comparison of texture (on logarithmic scale) between the analogue cheese made using the methods described herein and a few commercially available cheeses and cheese analogues.

The texture profile analysis showed hardness, adhesiveness, resilience, cohesion, springiness and chewiness as shown in Table 3 (Table 3, FIG. 3). NC1 mozzarella cheese analogue showed nearly the same cohesion and springiness when compared to real dairy low-moisture mozzarella (<10% deviation), and very similar hardness and chewiness profile (<30% deviation). It was consistently slightly harder, more resilient, more cohesive and chewier compared to both low-moisture mozzarella as well as the imitation mozzarella cheese. In comparison, the plant-based vegan mozzarella-style cheese deviates from dairy behavior, where it is extremely hard (~4.6× harder), chewy (~3.9× chewier) and adhesive (~19.6× more adhesive).

Interestingly, when compared to real dairy low-moisture mozzarella, NC1 mozzarella cheese analogue shows a different trend than imitation mozzarella for adhesiveness and springiness. While imitation mozzarella is more adhesive and springier than real dairy mozzarella, NC1 mozzarella cheese analogue is less adhesive and less springy than real dairy mozzarella. Reduced adhesiveness is a favourable cheese property as it represents the force required to remove the cheese from the probe (i.e. remove it sticking to teeth).

TABLE 3

Cheese Properties

| | Melt value (fold change) | Stretch (inches) | Hardness g | Adhesiveness g * sec | Resilience % | Cohesiveness % | Springiness % | Chewiness g |
| --- | --- | --- | --- | --- | --- | --- | --- | --- |
| Cheese types Low-moisture mozzarella | 2.4x | >18 | 1103.88 | 0.55 | 43.37 | 0.78 | 99.14 | 80.12 |

TABLE 3-continued

Cheese Properties

| | Melt value (fold change) | Stretch (inches) | Hardness g | Adhesiveness g * sec | Resilience % | Cohesiveness % | Springiness % | Chewiness g |
|---|---|---|---|---|---|---|---|---|
| Imitation mozzarella | 2.0x | <10 | 94.32 | 0.91 | 44.37 | 0.79 | 136.16 | 99.09 |
| Plant-based vegan mozzarella-1 style cheese | 0.8x | <1 | 477.01 | 10.78 | 49.09 | 0.7 | 93.41 | 313.17 |
| NC1 mozzarella cheese analogue | 1.5x | >12 | 1126.16 | 0.16 | 60.25 | 0.86 | 98.85 | 106.72 |

Example 6: Properties of Mozzarella Cheese Analogue from Recombinant Single Variant Alpha Casein Protein with an Altered Formulation Lacking Calcium Chloride Recombinant unphosphorylated alpha S1 casein (and truncated forms of the alpha S1 casein, as shown in FIG. 1), was used to make non-micellar mozzarella cheese analogue termed New Culture (NC2) mozzarella cheese. Casein, prewarmed coconut oil, trisodium citrate, disodium phosphate, sodium chloride and glucose were added in a beaker at concentrations specified in Table 4. To this, a mix of water, and modified potato starch were added at concentration specified in Table 4. The beaker was moved to a water bath preset at 85° C. temperature and the contents were mixed using a mixing propeller at a speed of 300 rpm for 9 mins. Lactic acid was added and mixed for an additional 1 min. The resulting mixture turned to a homogeneous non-micellar mass, transferred to standard molds, and allowed to sit in the fridge for 3 days. After fridge storage, the NC mozzarella cheese analogue was weighed to get yield estimation.

TABLE 4

Ingredient Composition and Concentration for Recombinant Single Casein Variant Cheese Analogue (NC2 mozzarella cheese analogue).

| Ingredient | Concentration (%, wt/wt) |
|---|---|
| Casein | 18.5 |
| Coconut oil | 24.2 |
| Trisodium citrate | 1 |
| Disodium phosphate | 2 |
| Sodium chloride | 1.49 |
| Water | 49.37 |
| Modified potato starch | 2.54 |
| Glucose | 0.4 |
| Lactic acid crystals | 0.5 |

The NC2 mozzarella cheese analogue samples were analyzed for qualitative and quantitative parameters such as pH, moisture, melt, stretch, and texture profile. These parameters were compared to a commercially available low-moisture mozzarella cheese, a commercially available imitation mozzarella cheese and a commercially available plant-based vegan mozzarella-style cheese (see Example 5 for further descriptions on these cheeses).

The cheese melt was quantified by a modified Schreiber melt test that used a custom-built imaging station mounted on a black magnetic hotbed. 0.5 g of cheese was melted at 95° C. for 15 mins on a magnetic hotbed. A time lapse of melting was recorded to measure increase in the melt area by measuring the pixels. The melt value was calculated by dividing the melted area by the unmelted area prior to melting. A melt value greater than 1 indicates melting.

An extensibility test was performed on a Texture Analyzer to quantitate cheese extensibility by inserting a 6-pronged hook into a 6 g sample of hand-cut cheese shreds that had been melted for 10 min at 90° C. and lifted until all the cheese strands broke. Distance to failure (breakage of all strands) representing extent of cheese stretch and work to extend representing tensile strength needed to stretch the cheese were quantified. The tests were performed on samples taken out of the fridge and then kept at ambient temperatures for at least 30 mins.

TABLE 5

Melt and stretch (extensibility) of cheese

| Cheese Type | Melt Value (Fold Change) | Extensibility- Work to Extend (g*sec) | Extensibility- Distance to Failure (mm) |
|---|---|---|---|
| Low-moisture mozzarella | 2.5 X | 105.10 | 224.12 |
| Imitation mozzarella | 2.0 X | 148.91 | 189.36 |
| Plant-based vegan mozzarella-style cheese | 0.8 X | 100.21 | 20.48 |
| NC2 mozzarella cheese analogue | 2.1 X | 128.41 | 227.66 |

NC2 mozzarella cheese analogue made from recombinant unphosphorylated alpha S1 casein with a formulation lacking calcium showed a dairy-like melt, dairy-like stretch and dairy-like extensibility properties. The moisture and pH of set NC2 mozzarella cheese analogue were 45.7% and 5.7 respectively.

Figure 4:
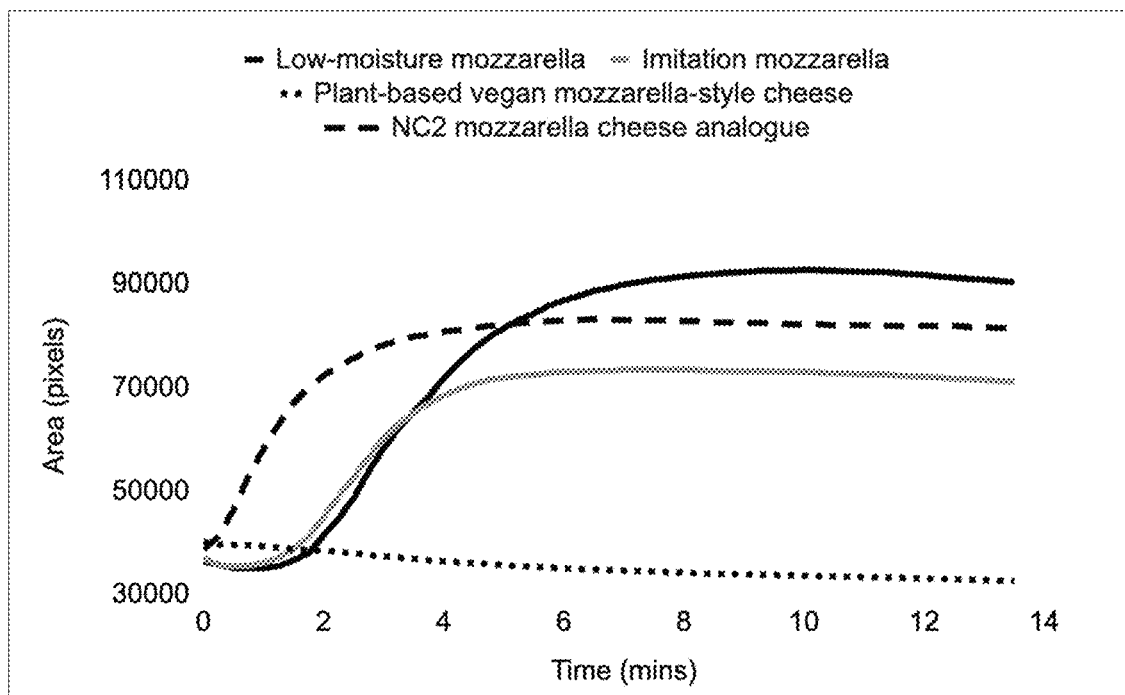
FIG. 4 illustrates a comparison of melt profile between the analogue cheese made using the methods described herein and a few commercially available cheeses and cheese analogues.

Surprisingly, the NC2 mozzarella cheese analogue made using the compositions described herein showed a better melt than the formulation in Example 5 and 7 and reached a melt value of 2.1x (Table 5, FIG. 4). In comparison, low-moisture mozzarella and imitation mozzarella reached melt values of 2.5x and 2.0x respectively. Plant-based vegan mozzarella-style cheese reached a melt value of 0.8x suggesting a lack of melt (and even shrinkage).

The NC2 mozzarella cheese analogue melted at a slower rate than low-moisture mozzarella, reaching its peak melt somewhat later during the modified Schreiber melt test. Imitation mozzarella and low-moisture mozzarella needed ~4-6 minutes for maximal melt, whereas NC2 mozzarella cheese analogue melted fully in ~6.5 minutes (FIG. 4).

Figure 5:
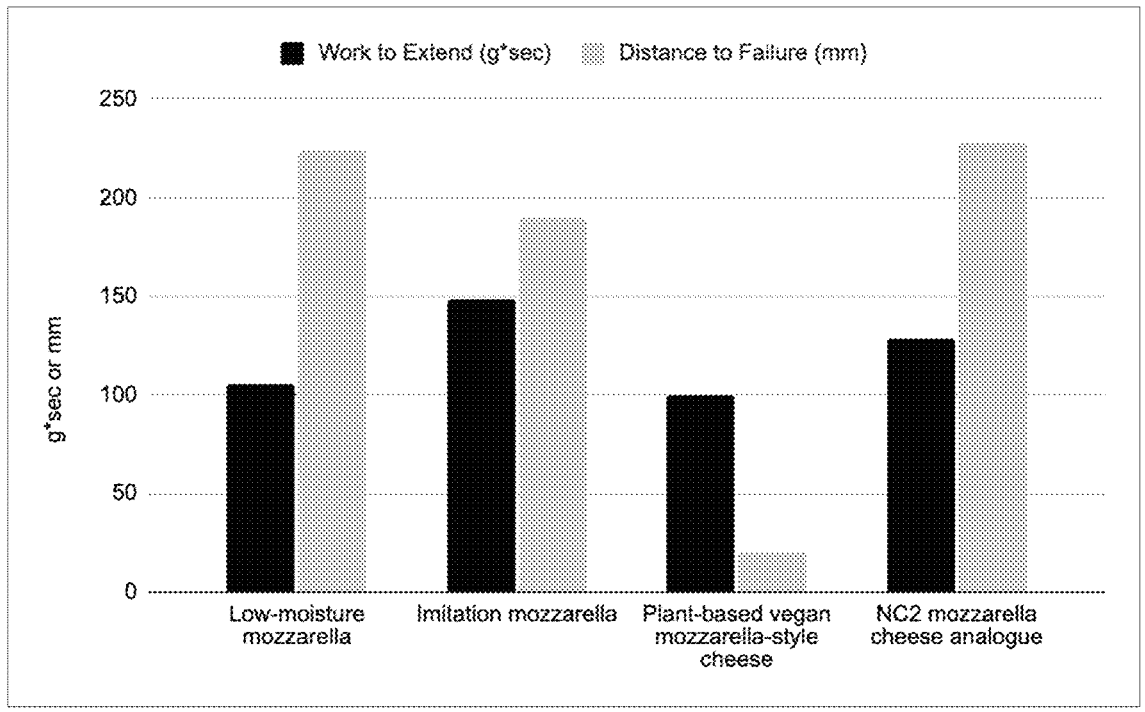
FIG. 5 illustrates a comparison of stretching ability (extensibility) between the analogue cheese made using the methods described herein and a few commercially available cheeses and cheese analogues.

NC2 mozzarella cheese analogue showed near identical extensibility to low-moisture mozzarella and imitation mozzarella while plant-based vegan mozzarella-style cheese failed to stretch entirely (Table 5, FIG. 5). The tensile strength (indicated by work to extend values, Table 5) needed to stretch NC2 mozzarella cheese analogue was in between the range needed to stretch the low-moisture mozzarella and imitation mozzarella. The NC2 cheese analogue stretched comparably to low-moisture mozzarella and significantly better than imitation mozzarella as indicated by the distance to failure values in Table 5. The NC2 mozzarella cheese analogue stretched to a length of ~228 mm. In comparison, low-moisture mozzarella imitation mozzarella stretched to length of ~224 mm and ~189 mm respectively (Table 5).

Example 7: Properties of Mozzarella Cheese Analogue from Recombinant Single Variant Alpha Casein Protein with a Different Fat Composition Recombinant unphosphorylated alpha S1 casein (and truncated forms of the alpha S1 casein, as shown in FIG. 1), was used to make non-micellar mozzarella cheese analogue termed New Culture (NC3) mozzarella cheese. Casein, water, palm stearin, canola oil, trisodium citrate, disodium phosphate, modified potato starch, and sodium chloride was added in a beaker at concentrations specified in Table 6. To this $CaCl_2$ was added at the concentration specified in Table 6. The beaker was moved to a water bath preset at 85° C. and the contents were mixed using a mixing propeller at a speed of 300 rpm for 9 minutes. Natural flavors and lactic acid were added, and the ingredients were mixed for an additional 1 minute. The resulting mixture turned to a homogeneous non-micellar mass, transferred to standard molds, and allowed to sit in the fridge for 7 days. After incubation, the NC3 mozzarella cheese analogue was weighed to get yield estimation.

TABLE 6

Ingredient Composition and Concentration for Recombinant Single Casein Variant Cheese Analogue (NC3 mozzarella cheese analogue).

| Ingredients | Concentration (%, wt/wt) |
| --- | --- |
| Casein | 18.5 |
| Palm Stearin | 17 |
| Canola Oil | 7 |
| Trisodium citrate | 0.7 |
| Disodium phosphate | 1.3 |
| Sodium chloride | 1.5 |
| Water | 49.7 |
| CaCl2 | 0.5 |
| Modified potato starch | 2.5 |
| Natural flavors | 1.1 |
| Lactic acid, 88% solution | 0.2 |

The NC3 mozzarella cheese analogue samples were analyzed for qualitative and quantitative parameters such as pH, moisture, melt, stretch, and texture profile as set forth in Example 6. These parameters were compared to low-moisture mozzarella cheese, imitation mozzarella cheese and a plant-based vegan mozzarella-style cheese (see Example 5 for further descriptions).

The cheese melt was quantified by a modified Schreiber melt test as described in Example 6. An extensibility test was performed on a TA.XTPlus Texture Analyzer to quantitate cheese extensibility as described in Example 6. The tests were performed on samples stored at 4° C.

TABLE 7

Melt and stretch (extensibility) of cheese

| Cheese Type | Melt Value (Fold Change) | Extensibility-Work to Extend (g*sec) | Extensibility-Distance to Failure (mm) |
| --- | --- | --- | --- |
| Low-moisture mozzarella | 2.5 X | 373.38 | 227.56 |
| Imitation mozzarella | 2.0 X | 155.85 | 224.96 |
| Plant-based vegan mozzarella-style cheese | 0.8 X | 8.25 | 22.3 |
| NC3 mozzarella cheese analogue | 1.6 X | 319.18 | 229.96 |

The texture profile was analyzed on TA-XT plus texture analyzer with TA-55 puncture probe. 1.5-1.9 g of cheese sample was cut in 1.5 cm l×1.5 cm w×1 cm h dimension. The tests were performed on samples stored at 4° C.

TABLE 8

Cheese Properties

| Cheese types | Hardness g | Adhesiveness g * sec | Resilience % | Cohesiveness % | Springiness % | Chewiness g |
| --- | --- | --- | --- | --- | --- | --- |
| Low-moisture mozzarella | 345.7 | 5.84 | 52.38 | 0.80 | 95.60 | 263.53 |
| Imitation mozzarella | 205.6 | 6.85 | 53.72 | 0.80 | 99.06 | 163.85 |
| Plant-based vegan mozzarella-style cheese | 636.7 | 4.14 | 54.71 | 0.66 | 101.37 | 431.50 |
| NC3 mozzarella cheese analogue | 729.9 | 0.26 | 55.12 | 0.29 | 214.19 | 184.14 |

NC3 mozzarella cheese analogue made from recombinant unphosphorylated alpha S1 casein with a different fat composition showed dairy-like melt, dairy-like stretch and dairy-like extensibility properties. The moisture and pH of set NC3 mozzarella cheese analogue were 44.8% and 5.7 respectively.

Figure 6:
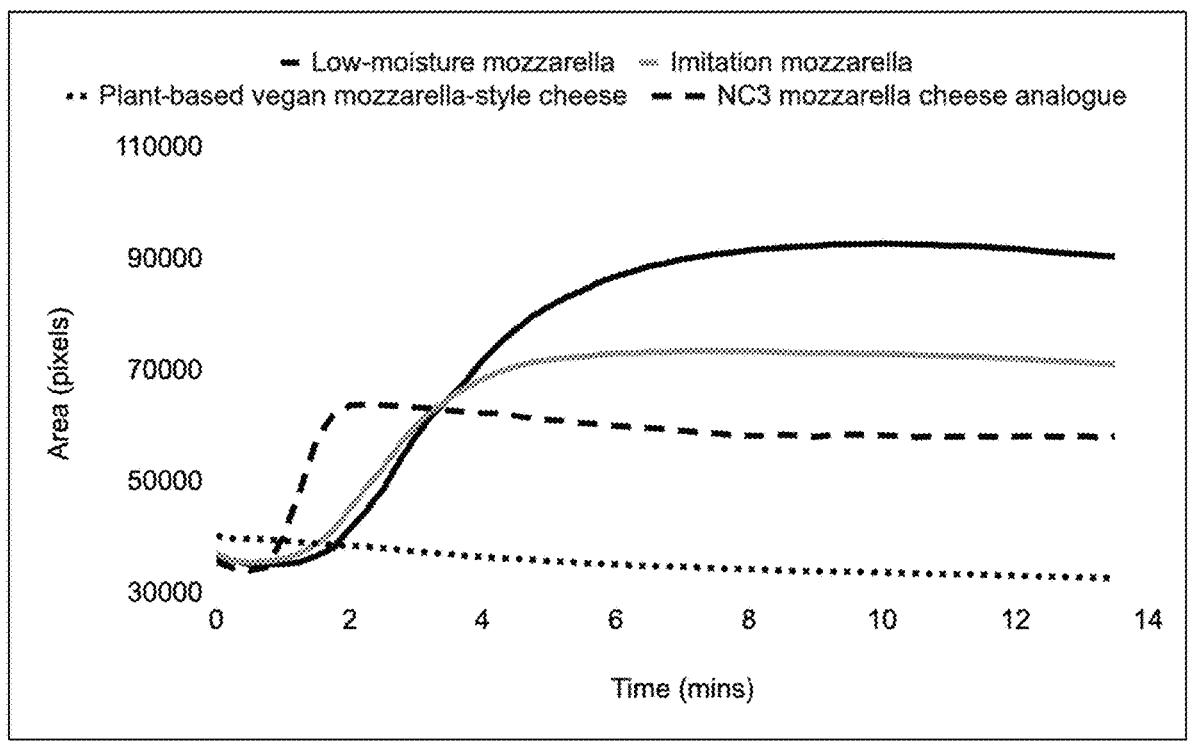
FIG. 6 illustrates a comparison of melt between the analogue cheese made using the methods described herein and a few commercially available cheeses and cheese analogues.

The NC3 mozzarella cheese analogue made using the compositions described herein reached a melt value of 1.6× (Table 7, FIG. 6). In comparison, low-moisture mozzarella and imitation mozzarella reached melt values of 2.5× and 2× respectively. The plant-based vegan mozzarella-style cheese reached a melt value of 0.8× suggesting a lack of melt (and even shrinkage).

Surprisingly, NC3 mozzarella cheese analogue melts at a quicker rate than low-moisture mozzarella, reaching its peak melt sooner during the modified Schreiber melt test. Imitation mozzarella and low-moisture mozzarella needed ~4-6 minutes for maximal melt, whereas NC3 mozzarella cheese analogue melted fully in ~2 minutes (FIG. 6).

This is likely due to the substitution of the coconut oil with a combination of palm stearin and canola oil.

Figure 7:
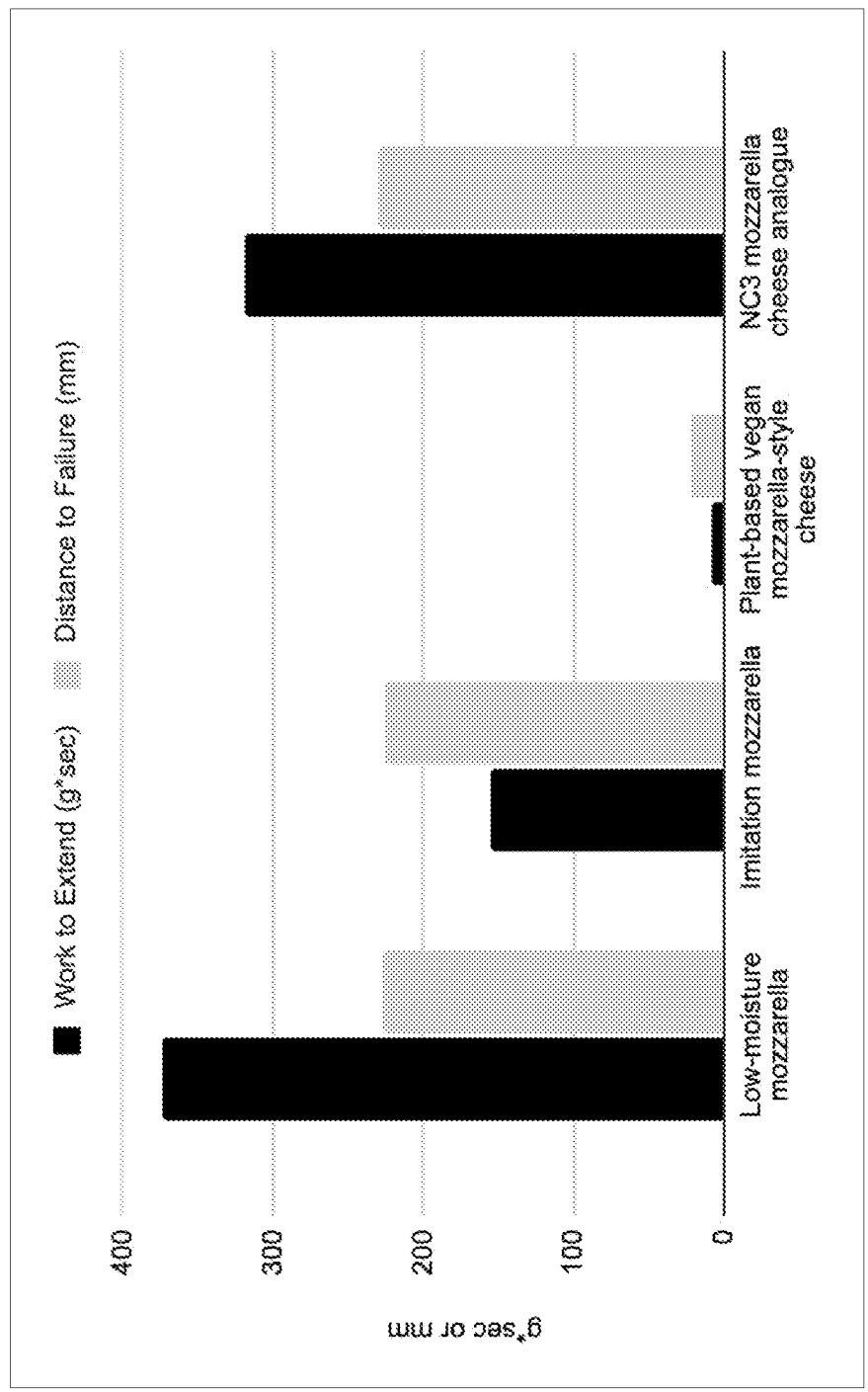
FIG. 7 illustrates a comparison of stretching ability (extensibility) between the analogue cheese 07-made using the methods described herein and a few commercially available cheeses and cheese analogues.

NC3 mozzarella cheese analogue showed near identical extensibility to low-moisture mozzarella and imitation mozzarella while plant-based vegan mozzarella-style cheese failed to stretch entirely (Table 7, FIG. 7). The tensile strength (indicated by work to extend values, Table 7) needed to stretch NC1 mozzarella cheese analogue was similar to that needed to stretch the low-moisture mozzarella whereas imitation mozzarella needed significantly lower tensile strength. The NC3 cheese analogue stretched to the same extent as low-moisture mozzarella and imitation mozzarella as indicated by the distance to failure values in Table 7. The NC3 mozzarella cheese analogue stretched to a length of ~230 mm. In comparison, low-moisture mozzarella imitation mozzarella stretched to length of ~228 mm and ~225 mm respectively (Table 7).

Figure 8:
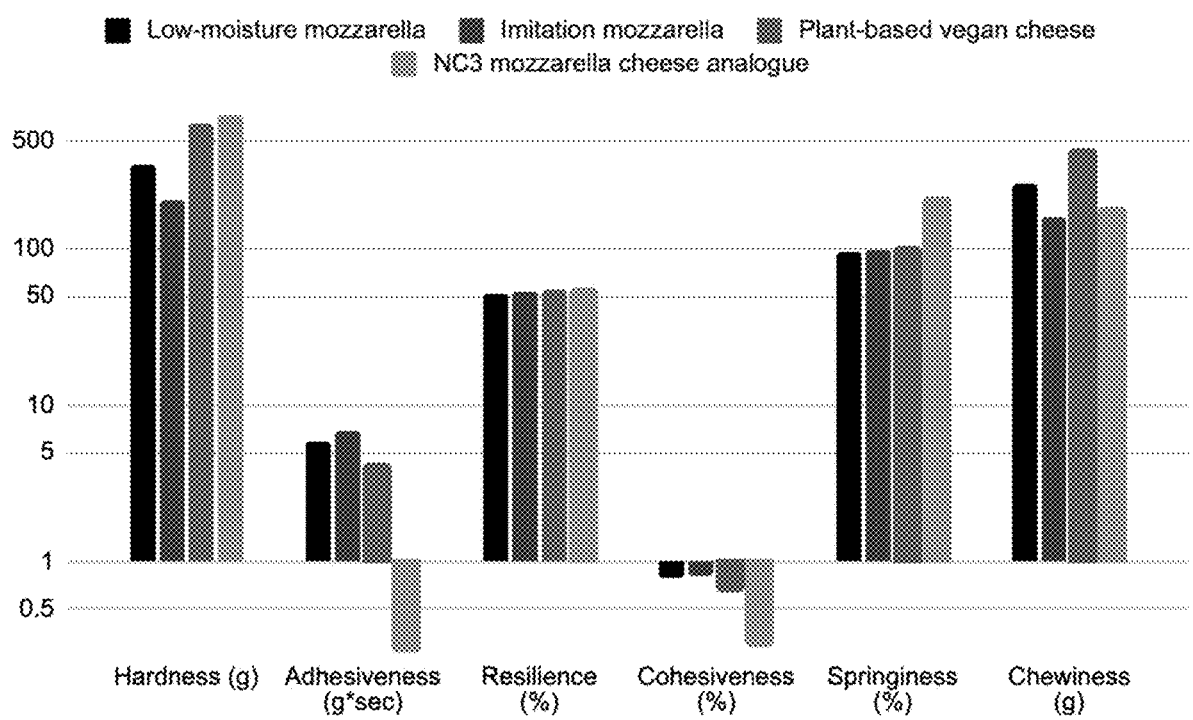
FIG. 8 illustrates a comparison of texture (on logarithmic scale) between the analogue cheese made using the methods described herein and a few commercially available cheeses and cheese analogues.

The texture profile analysis showed hardness, adhesiveness, resilience, cohesion, springiness and chewiness (as shown in Table 8, FIG. 8). The NC3 mozzarella cheese analogue showed nearly the same chewiness (<10% deviation) when compared to imitation mozzarella. In comparison, plant-based vegan mozzarella-style cheese has higher chewiness (>1.5×) compared to low-moisture mozzarella and imitation mozzarella. The NC3 mozzarella cheese shows similar resilience (<10% deviation), higher hardness, springiness, and lower adhesiveness and cohesiveness compared to other commercial cheeses.

Interestingly, when compared to animal-derived dairy low-moisture mozzarella, NC3 mozzarella cheese analogue shows a different trend than imitation mozzarella for adhesiveness. While imitation mozzarella is more adhesive than real dairy mozzarella, NC3 mozzarella cheese analogue is less adhesive. Reduced adhesiveness is a favorable cheese property as it represents the force required to remove the cheese from the probe, which corresponds to stickiness in consumer's mouth (i.e. sticking to teeth when chewing).

Example 8: Properties of Mozzarella Cheese Analogue from Recombinant Single Variant Alpha Casein Protein with an Altered Formulation and Altered Processing Parameters Recombinant unphosphorylated alpha S1 casein (and truncated forms of the alpha S1 casein, as shown in FIG. 1), was used to make non-micellar mozzarella cheese analogue termed New Culture (NC4) mozzarella cheese. Casein, water, palm stearin, canola oil, modified potato starch sodium chloride, and $CaCl_2$ were added in a beaker at concentrations specified in Table 9. To this, trisodium citrate and dipotassium phosphate were added at the concentration specified in Table 9. The beaker was moved to a water bath preset at 85° C. and the contents were mixed using a mixing propeller at a speed of 500 rpm for 4 minutes, followed by 1 minute at 300 rpm, at which point natural flavors were also added. Lactic acid was added and the ingredients were mixed for an additional 1 minute at 300 rpm. The resulting mixture turned to a homogeneous non-micellar mass, transferred to standard molds, and allowed to sit in the fridge for 7 days. After incubation, the NC4 mozzarella cheese analogue was weighed to get yield estimation.

TABLE 9

Ingredient Composition and Concentration for Recombinant Single Casein Variant Cheese Analogue (NC4 mozzarella cheese).

| Ingredients | Concentration (%, wt/wt) |
| --- | --- |
| Casein | 18.5 |
| Palm Stearin | 17 |
| Canola Oil | 7 |
| Trisodium citrate | 0.7 |
| Disodium phosphate | 1.3 |
| Sodium chloride | 1.5 |
| Water | 49.7 |
| CaCl2 | 0.5 |
| Modified potato starch | 2.5 |
| Natural flavors | 1.1 |
| Lactic acid, 88% solution | 0.2 |

The NC4 mozzarella cheese analogue samples were analyzed for qualitative and quantitative parameters such as pH, moisture, melt, stretch, and texture profile. These parameters were compared to low-moisture mozzarella cheese, imitation mozzarella cheese and plant-based vegan mozzarella-style cheese (see Example 5 for further descriptions).

The cheese melt was quantified by a modified Schreiber melt test as described in Example 6. An extensibility test was performed on a TA.XTPlus Texture Analyzer to quantitate cheese extensibility as described in Example 6. The tests were performed on samples stored at 4° C.

TABLE 10

Melt and stretch (extensibility) of cheese

| Cheese Type | Melt Value (Fold Change) | Extensibility-Work to Extend (g*sec) | Extensibility-Distance to Failure (mm) |
| --- | --- | --- | --- |
| Low-moisture mozzarella | 2.5 X | 373.37 | 227.56 |
| Imitation mozzarella | 2.0 X | 155.85 | 224.96 |
| Plant-based vegan mozzarella-style cheese | 0.8 X | 8.24 | 22.30 |
| NC4 mozzarella cheese analogue | 1.5 X | 268.80 | 241.46 |

NC4 mozzarella cheese analogue made from recombinant unphosphorylated alpha S1 casein and its truncated forms as the only protein ingredient in the cheese, using a different formulation and different processing parameters compared to examples 5, 6, and 7, also showed dairy-like melt, dairy-like stretch and dairy-like extensibility properties. The moisture and pH of set NC4 mozzarella cheese analogue were 48.1% and 5.7 respectively.

Figure 9:
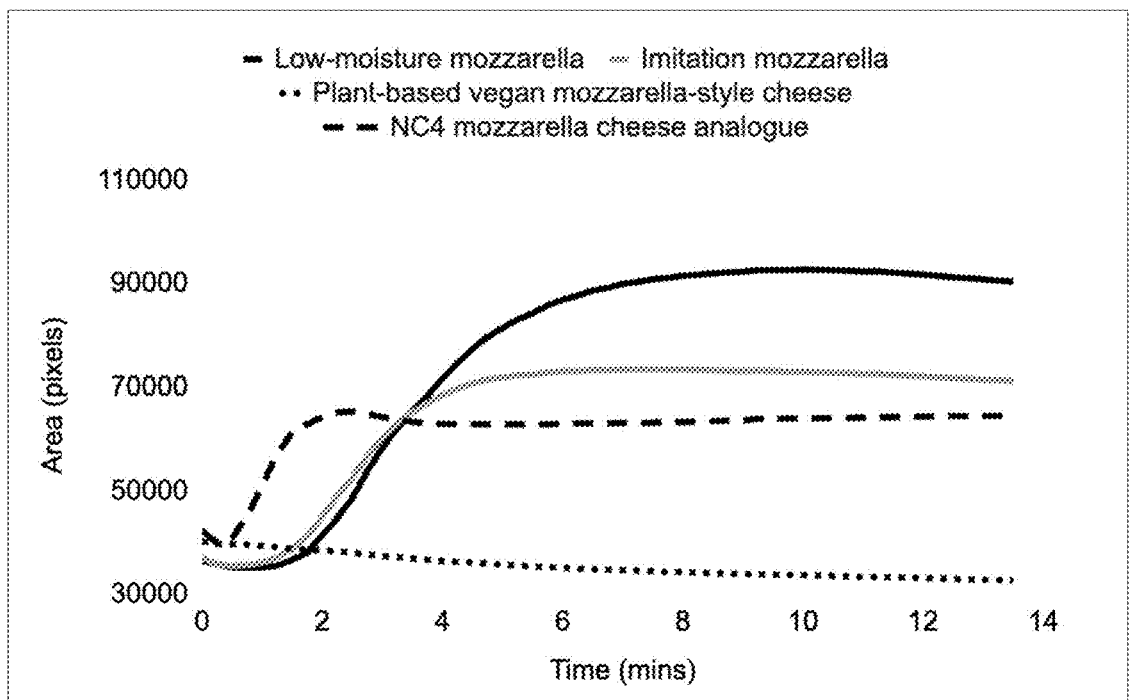
FIG. 9 illustrates a comparison of melt profile between the analogue cheese made using the methods described herein and a few commercially available cheeses and cheese analogues.

The NC4 mozzarella cheese analogue using the compositions described herein reached a melt value of 1.5× (Table 10, FIG. 9). In comparison, low-moisture mozzarella and imitation mozzarella reached melt values of 2.5× and 2× respectively. The plant-based vegan mozzarella-style cheese reached a melt value of 0.8× suggesting a lack of melt (and even shrinkage).

More notably, NC4 mozzarella cheese analogue melted at a quicker rate than low-moisture mozzarella, reaching its peak melt sooner during the modified Schreiber melt test. Imitation mozzarella and low-moisture mozzarella needed ~4-6 minutes for maximal melt, whereas NC4 mozzarella cheese analogue melted fully in ~2 minutes (FIG. 9).

Figure 10:
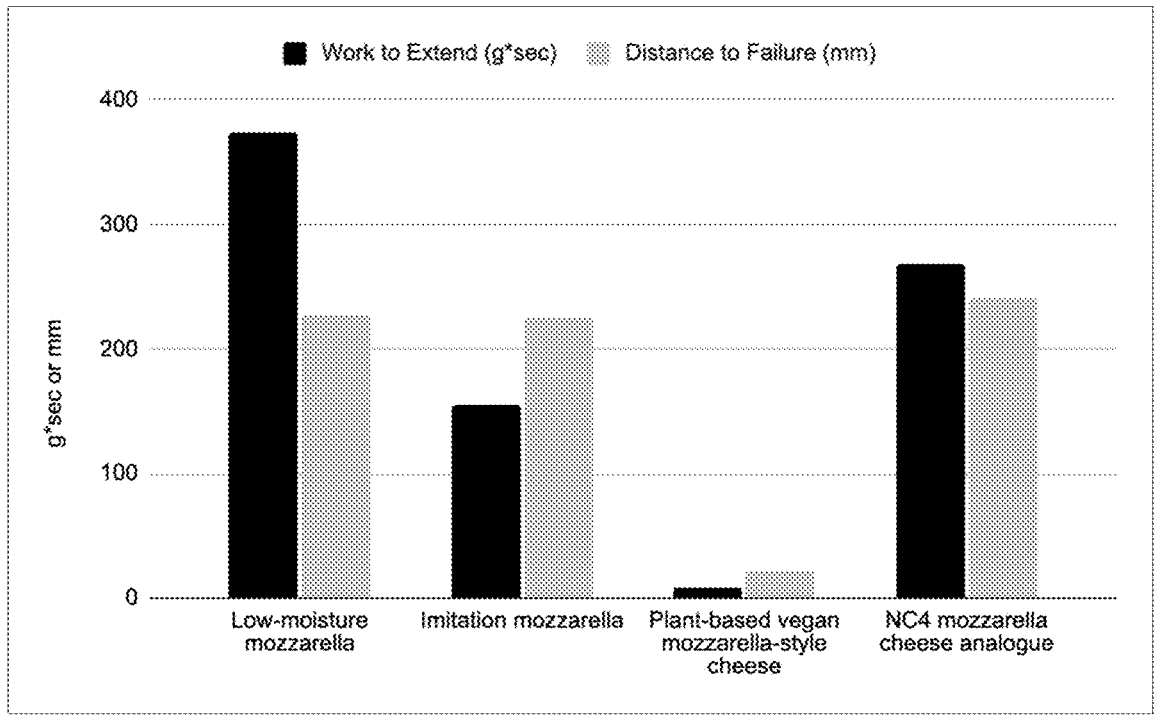
FIG. 10 illustrates a comparison of stretching ability (extensibility) between the analogue cheese made using the methods described herein and a few commercially available cheeses and cheese analogues.

NC4 mozzarella cheese analogue showed similar extensibility to low-moisture mozzarella and imitation mozzarella while plant-based vegan mozzarella-style cheese failed to stretch entirely (Table 10, FIG. 10). The tensile strength (indicated by work to extend values, Table 10) needed to stretch NC4 mozzarella cheese analogue was in the range of tensile strength of low-moisture mozzarella and imitation mozzarella. The NC4 cheese analogue stretched better than low-moisture mozzarella and imitation mozzarella as indicated by the distance to failure values in Table 10. The NC4 mozzarella cheese analogue stretched to a length of ~241 mm. In comparison, low-moisture mozzarella and imitation mozzarella stretched to length of ~228 mm and ~225 mm respectively (Table 10, FIG. 10).

What is claimed is:

1. A cheese analogue comprising a recombinant single variant of an alpha casein protein, wherein the recombinant single variant provides at least one dairy-like property selected from the group consisting of adhesiveness, stretch, texture, mouthfeel, melt, hardness, creaminess, and flexibility, wherein the recombinant single variant is not an animal-derived casein and has not been physically dissociated from a casein micelle, and wherein the cheese analogue lacks any caseins or other dairy proteins other than the recombinant single variant.

2. The cheese analogue of claim 1, wherein the recombinant single variant of the alpha casein protein lacks one or more post-translational modifications of a native alpha casein protein.

3. The cheese analogue of claim 1, wherein the recombinant single variant of the alpha casein protein lacks post-translational modifications.

4. The cheese analogue of claim 1, wherein the recombinant single variant of the alpha casein protein lacks phosphorylation.

5. The cheese analogue of claim 1, wherein the recombinant single variant of the alpha casein protein is a recombinant alpha-s1 casein protein.

6. The cheese analogue of claim 5, wherein at least 5% of the cheese analogue is the recombinant alpha-s1 casein protein wt/wt.

7. The cheese analogue of claim 5, wherein the recombinant alpha-s1 casein protein comprises an amino acid sequence of a ruminant alpha-s1 casein protein.

8. The cheese analogue of claim 1, wherein the recombinant single variant of an alpha casein protein comprises an amino acid sequence of SEQ ID NOs: 2 or 3 or an amino acid sequence with at least 90% sequence identity to SEQ ID NOs.: 2 or 3.

9. The cheese analogue of claim 1, wherein the recombinant single variant of an alpha casein protein is not comprised in a micellar form within the cheese analogue.

10. The cheese analogue of claim 1, wherein the recombinant single variant of an alpha casein protein has a N-terminus and comprises one or more non-native amino acids at the N-terminus.

11. The cheese analogue of claim 10, wherein the recombinant single variant of an alpha casein protein has a N-terminal position and comprises a non-native methionine at the N-terminal position.

12. The cheese analogue of claim 1, wherein the cheese analogue is a vegan cheese analogue.

13. The cheese analogue of claim 1, further comprising one or more of (a) a plant-derived oil; (b) a plant-derived starch; (c) a sugar; and (d) a salt.

14. The cheese analogue of claim 1, further comprising a flavoring selected from cheddar flavor, parmesan flavor or mozzarella flavoring.

15. The cheese analogue of claim 1, wherein the cheese analogue is a mozzarella analogue.

16. The cheese analogue of claim 15, wherein the adhesiveness of the cheese analogue is reduced as compared to a plant-derived cheese analogue.

17. The cheese analogue of claim 1, wherein the cheese analogue lacks micelles or micellar forms.

* * * * *